US011327075B2

(12) United States Patent
Kamei et al.

(10) Patent No.: US 11,327,075 B2
(45) Date of Patent: May 10, 2022

(54) HYDROGEL PLATFORM FOR AQUEOUS TWO-PHASE CONCENTRATION OF A TARGET TO ENHANCE ITS DETECTION

(71) Applicant: The Regents of the University of California, Oakland, CA (US)

(72) Inventors: Daniel Takashi Kamei, Monterey Park, CA (US); Benjamin Ming Wu, San Marino, CA (US); David Yuan Pereira, Los Angeles, CA (US); Chloe Michelle Wu, San Marino, CA (US); Matthew Foosing Yee, Saratoga, CA (US); Joshua Anthony Keefe, Sunnyvale, CA (US); Christina Caroline Pearce, Orinda, CA (US); Amir Adam Dailamy, Calabasas, CA (US); Vincent K. Wong, San Gabriel, CA (US); Nguyen Khoi Le, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 296 days.

(21) Appl. No.: 16/326,687

(22) PCT Filed: Aug. 21, 2017

(86) PCT No.: PCT/US2017/047849

§ 371 (c)(1),
(2) Date: Feb. 19, 2019

(87) PCT Pub. No.: WO2018/039139

PCT Pub. Date: Mar. 1, 2018

(65) Prior Publication Data

US 2019/0187140 A1 Jun. 20, 2019

Related U.S. Application Data

(60) Provisional application No. 62/483,221, filed on Apr. 7, 2017, provisional application No. 62/378,087, filed on Aug. 22, 2016.

(51) Int. Cl.
*G01N 33/559* (2006.01)
*G01N 33/558* (2006.01)
(Continued)

(52) U.S. Cl.
CPC ..... *G01N 33/559* (2013.01); *G01N 33/48792* (2013.01); *G01N 33/545* (2013.01);
(Continued)

(58) Field of Classification Search
CPC ............... G01N 33/559; G01N 33/558; G01N 33/54353; G01N 33/48792;
(Continued)

(56) References Cited

U.S. PATENT DOCUMENTS 5,141,850 A 8/1992 Cole et al.
6,194,221 B1 2/2001 Rehg et al.
(Continued)

FOREIGN PATENT DOCUMENTS

CN 106662582 A 5/2017
EP 1064553 A1 1/2001
(Continued)

OTHER PUBLICATIONS

PCT International Search Report and Written Opinion dated Jun. 3, 2015 issued in PCT/US2015/019297.
(Continued)

*Primary Examiner* — Jennifer Wecker
*Assistant Examiner* — Michael Paul Shimek
(74) *Attorney, Agent, or Firm* — Tom Hunter; Weaver Austin Villeneuve & Sampson LLP

(57) ABSTRACT

It was discovered that hydrogel scaffolds can be used to induce phase separation as aqueous two-phase systems (ATPSs) pass through and/or rehydrate the scaffolds, allowing for concentration of target analyte(s) (e.g., biomolecule(s)) into a particular phase of the ATPS or into
(Continued)

a leading front. Accordingly, in various embodiments methods and devices are provided that utilize aqueous two-phase systems and hydrogel scaffolds to improve the sensitivity of assays (e.g., of point-of-care assays) without sacrificing cost or ease of use.

22 Claims, 18 Drawing Sheets

(51) Int. Cl.
*G01N 33/543* (2006.01)
*G16H 30/40* (2018.01)
*G01N 33/487* (2006.01)
*G01N 33/545* (2006.01)
*G01N 33/569* (2006.01)
*C08J 3/075* (2006.01)
*G01N 1/28* (2006.01)

(52) U.S. Cl.
CPC ... *G01N 33/5436* (2013.01); *G01N 33/54353* (2013.01); *G01N 33/558* (2013.01); *G01N 33/56983* (2013.01); *G16H 30/40* (2018.01); *C08J 3/075* (2013.01); *C08J 2333/14* (2013.01); *G01N 1/28* (2013.01); *G01N 2333/183* (2013.01)

(58) Field of Classification Search
CPC ............. G01N 33/5436; G01N 33/545; G01N 33/56983; G01N 1/28; G01N 2333/183; G16H 30/40; C08J 3/075; C08J 2333/14
See application file for complete search history.

(56) References Cited

U.S. PATENT DOCUMENTS 6,855,561 B2 2/2005 Jerome et al.
6,924,153 B1 8/2005 Boehringer et al.
6,979,576 B1 12/2005 Cheng et al.
7,179,657 B2 2/2007 Jerome et al.
7,226,793 B2 6/2007 Jerome et al.
7,459,314 B2 12/2008 Guo et al.
7,537,937 B2 5/2009 Jerome et al.
7,553,675 B2 6/2009 Jerome et al.
7,666,614 B2 2/2010 Cheng et al.
7,794,656 B2 9/2010 Liang et al.
7,867,780 B2 1/2011 Jones et al.
7,932,099 B2 4/2011 Egan et al.
8,003,765 B2 8/2011 Pentyala et al.
8,030,091 B2 10/2011 Jerome et al.
8,193,002 B2 6/2012 Guo et al.
8,377,710 B2 2/2013 Whitesides et al.
8,445,293 B2 5/2013 Babu et al.
8,603,832 B2 12/2013 Whitesides et al.
8,628,729 B2 1/2014 Carrilho et al.
8,828,739 B2 9/2014 Guo et al.
9,193,988 B2 11/2015 Whitesides et al.
9,207,236 B2 12/2015 Cary
9,250,236 B2 2/2016 Babu et al.
9,347,955 B2 5/2016 Pieribone
9,823,247 B2 11/2017 Kamei et al.
10,006,911 B2 6/2018 Kamei et al.
10,359,423 B2 7/2019 Kamei et al.
10,578,616 B2 3/2020 Kamei et al.
2003/0215358 A1 11/2003 Schulman et al.
2004/0002168 A1 1/2004 Remington et al.
2004/0203079 A1 10/2004 Pentyala et al.
2004/0214171 A1 10/2004 Yamashita et al.
2005/0239216 A1 10/2005 Feistel
2006/0019406 A1 1/2006 Wei et al.
2006/0025579 A1 2/2006 Riedl et al.
2007/0003992 A1 1/2007 Pentyala et al.
2007/0140911 A1* 6/2007 Carney .............. A61B 10/0045 422/400
2007/0196864 A1 8/2007 Pentyala et al.
2007/0292902 A1 12/2007 Cheng et al.
2008/0138842 A1 6/2008 Boehringer et al.
2008/0227113 A1 9/2008 Pentyala et al.
2008/0227220 A1 9/2008 Franse et al.
2008/0254440 A1 10/2008 Uchida et al.
2009/0110601 A1 4/2009 Levi et al.
2009/0191648 A1 7/2009 Bohannon
2010/0227323 A1 9/2010 Baeumner et al.
2011/0003310 A1 1/2011 Ennis et al.
2011/0072885 A1 3/2011 Inana et al.
2011/0151479 A1 6/2011 Stevens et al.
2011/0312074 A1 12/2011 Azimi et al.
2012/0107956 A1 5/2012 Boehringer et al.
2012/0238008 A1 9/2012 Henry et al.
2013/0065784 A1 3/2013 Takayama et al.
2013/0102063 A1 4/2013 Levi et al.
2013/0266956 A1 10/2013 Tia et al.
2014/0004539 A1 1/2014 Simon et al.
2014/0038222 A1* 2/2014 Alt ...................... G01N 21/648 435/29
2014/0228549 A1 8/2014 Schembecker et al.
2015/0017656 A1 1/2015 Wang
2015/0099656 A1* 4/2015 Manuguerra ........ G01N 33/564 506/9
2015/0198592 A1 7/2015 Wang
2015/0253320 A1 9/2015 Kamei et al.
2015/0323534 A1 11/2015 Egan et al.
2016/0266119 A1 9/2016 Sambursky et al.
2016/0282343 A1 9/2016 Jeyendran et al.
2016/0313307 A1 10/2016 Titmus et al.
2017/0323441 A1 11/2017 Shah et al.
2018/0100854 A1 4/2018 Kamei et al.
2018/0259521 A1 9/2018 Kamei et al.
2019/0033308 A1 1/2019 Kamei et al.
2019/0250156 A1 8/2019 Kamei et al.
2019/0391143 A1 12/2019 Kamei et al.
2020/0033336 A1 1/2020 Kamei et al.
2020/0150116 A1 5/2020 Kamei et al.
2020/0284791 A1 9/2020 Kamei et al.

FOREIGN PATENT DOCUMENTS

EP 1340085 A1 9/2003
EP 1436592 A1 7/2004
EP 1733233 A2 12/2006
EP 1771734 A1 4/2007
EP 0941468 B1 7/2007
EP 2076775 A2 7/2009
EP 2126569 A2 12/2009
EP 2245135 A2 11/2010
EP 2426498 A1 3/2012
JP H03-130663 A 6/1991
JP 2003-250575 A 9/2003
JP 2007-500363 A 1/2007
JP 2008-537119 A 9/2008
JP 2011-075366 A 4/2011
JP 2013-531259 A 8/2013
JP 2013-181870 A 9/2013
WO WO 98/018964 5/1998
WO WO 2004/081528 A2 9/2004
WO WO 2005/074609 A2 8/2005
WO WO 2005/098439 A2 10/2005
WO WO 2005/042579 A1 12/2005
WO WO 2007/092302 A2 8/2007
WO WO 2008/043040 A2 4/2008
WO WO 2011/116256 A2 9/2011
WO WO 2011/159537 A2 12/2011
WO WO 2012/010666 A1 1/2012
WO WO 2013/105090 A1 7/2013
WO WO 2015/134938 A1 9/2015
WO WO-2015134938 A1 * 9/2015 ........... G01N 33/558
WO WO 2017/041030 A1 3/2017
WO WO 2017/214315 A1 12/2017
WO WO 2018/039139 A1 3/2018

(56) References Cited

FOREIGN PATENT DOCUMENTS

WO WO 2018/183211 A1 10/2018
WO WO 2018/222765 A1 12/2018

OTHER PUBLICATIONS

PCT International Preliminary Report on Patentability dated Sep. 13, 2016 issued in PCT/US2015/019297.
PCT International Search Report and Written Opinion dated Dec. 22, 2016 issued in PCT/US2016/050257.
PCT International Preliminary Report on Patentability dated Mar. 15, 2018 issued in PCT/US2016/050257.
PCT International Search Report and Written Opinion dated Sep. 20, 2017 issued in PCT/US2017/036418.
PCT International Preliminary Report on Patentability dated Dec. 20, 2018 issued in PCT/US2017/036418.
PCT International Search Report and Written Opinion dated Dec. 1, 2017 issued in PCT/US2017/047849.
PCT International Preliminary Report on Patentability dated Feb. 26, 2019 issued in PCT/US2017/047849.
PCT International Search Report and Written Opinion dated Aug. 3, 2018 issued in PCT/US2018/035204.
PCT International Preliminary Report on Patentability dated Dec. 3, 2019 issued in PCT/US2018/035204.
PCT International Search Report and Written Opinion dated Jun. 15, 2018 issued in PCT/US2018/024392.
PCT International Preliminary Report on Patentability dated Oct. 1, 2019 issued in PCT/US2018/024392.
AU Examination report No. 1 dated Oct. 8, 2019 issued in AU 2015226930.
CN First Office Action dated Jan. 22, 2018 issued in CN 201580023439.9.
CN Second Office Action dated Nov. 29, 2018 issued in CN 201580023439.9.
EP Extended Search Report dated Oct. 26, 2017 issued in EP 15758881.5.
JP Office Action dated Feb. 8, 2019 issued in JP 2016-573716.
JP 2nd Office Action dated Feb. 3, 2020 issued in JP 2016-573716.
MY Office Action dated Dec. 2, 2019 issued in MY PI2016001615.
SG Office Action [Search Report and Written Opinion] dated Jan. 24, 2018 issued in SG 11201607582R.
SG Examination Report dated May 14, 2019 issued in SG 11201607582R.
CN First Office Action dated Mar. 27, 2020 issued in CN 201680059385.6.
EP Partial Supplementary Search Report dated Feb. 4, 2019 issued in EP 16843134.4.
EP Extended Supplementary Search Report dated Jun. 14, 2019 issued in EP 16843134.4.
EP Extended Supplementary Search Report dated Dec. 6, 2019 issued in EP 17810966.6.
U.S. Office Action dated Jan. 6, 2017 issued in U.S. Appl. No. 14/641,022.
U.S. Notice of Allowance dated Jul. 20, 2017 issued in U.S. Appl. No. 14/641,022.
U.S. Notice of Allowance dated Aug. 8, 2017 issued in U.S. Appl. No. 14/641,022.
U.S. Notice of Allowance dated Feb. 28, 2018 issued in U.S. Appl. No. 15/787,638.
U.S. Office Action dated Nov. 2, 2018 issued in U.S. Appl. No. 15/990,398.
U.S. Notice of Allowance dated Apr. 3, 2019 issued in U.S. Appl. No. 15/990,398.
U.S. Office Action [Restriction Requirement] dated May 14, 2019 issued in U.S. Appl. No. 15/756,542.
U.S. Office Action dated Sep. 26, 2019 issued in U.S. Appl. No. 15/756,542.
Ahmed (2015) "Hydrogel: Preparation, characterization, and applications: A review" *J. Adv. Res.*, 6:105-121.
Arrer et al. (2002) "β-Trace Protein as a Marker for Cerebrospinal Fluid Rhinorrhea" *Clin. Chem.* 48(6): 939-941.
Bachmann et al. (2002) "Predictive values of beta-trace protein (prostaglandin D synthase) by use of laser-nephelometry assay for the identification of cerebrospinal fluid." *Neurosurgery*, 50(3): 571-577.
Carter and Cary (2007) "Lateral flow microarrays: a novel platform for rapid nucleic acid detection based on miniaturized lateral flow chromatography," *Nucleic Acids Research* 35(10): e74 (11 pages).
Center for Disease Control and Prevention. Diagnostic Tests for Zika Virus. "Updated Guidance for US Laboratories Testing for Zika Virus Infection Jul. 24, 2017"; Availabe at: https://www.cdc.gov/zika/transmission/index.html, 16 pages.
Chiu et al. (2014) "Biomarker concentration and detection directly on paper," abstract, *MicroTAS Annual Meeting, San Antonio, Texas*, 3 pages.
Chiu et al. (2014) "Dextran-coated gold nanoprobes for the concentration and detection of protein biomarkers," *Annals of Biomedical Engineering* 42(11): 2322-2332.
Chiu et al. (2014) "Manipulating gold nanoparticles to achieve effective and rapid detection of protein biomarkers for resource-poor settings," slides from presentation, not published/distributed. *The Annual UC System wide Bioengineering Symposium, Irvine, California*, 24 slides.
Chiu et al. (2014) "Polymer-coated gold nanoprobes for the concentration and detection of protein biomarkers for resource-poor settings," *The Biomedical Engineering Society Annual Meeting, San Antonio, Texas*, poster, 1 page.
Chiu et al. (2014) "Polymer-coated gold nanoprobes for the concentration and detection of protein biomarkers for resource-poor settings," *The Biomedical Engineering Society Annual Meeting, San Antonio, Texas*, published abstract, 1 page.
Chiu et al. (2014) "Simultaneous concentration and detection of biomarkers on paper," *Lab Chip* 14: 3021-3028.
Chiu et al. (2014) "Simultaneous concentration and detection of biomarkers on paper," poster presentation, *MicroTAS Annual Meeting, San Antonio, Texas*, 1 page.
Chiu et al. (2014) "Simultaneously concentrating and detecting biomarkers on paper," abstract of podium presentation, *The Biomedical Engineering Society Annual Meeting, San Antonio, Texas*, 1 page.
Chiu et al. (2014) "Simultaneously concentrating and detecting biomarkers on paper," slides from podium presentation, *The Biomedical Engineering Society Annual Meeting, San Antonio, Texas*, 52 slides.
Chiu et al. (2015) "Creating the gold standard point-of-care test for sexually transmitted infections," 20 slide deck, not published, not distributed, for judging only, *OneStart Competition*, 20 pages.
Chiu et al. (2015) "Creating the gold standard point-of-care test for sexually transmitted infections," 3 minute/3 slide deck, *OneStart Competition*, 3 pages.
Chiu et al., (2015) "An aqueous two-phase system for the concentration and extraction of proteins from the interface for detection using the lateral-flow immunoassay," *PLoS One* 10: e0142654 (14 pages).
Chiu, et al. (2010) "Generation of Porous Poly(Ethylene Glycol) Hydrogels by Salt Leaching," *Tissue Engineering Part C: Methods* 16: 905-912.
Cho, et al. (2013) "Lateral-flow enzyme immunoconcentration for rapid detection of Listeria monocytogenes." *Anal Bioanal Chem* 405:3313-3319.
Fang et al. (2011) "Barcode lateral flow immunochromatographic strip for prostate acid phosphatase determination," *J. Pharmaceut. Biomed. Anal.*, 56(5): 1035-1040.
Fu et al. (2011) "Enhanced sensitivity of lateral flow tests using a two-dimensional paper network format," *Anal. Chem.* 83(20): 7941-7946 (NIH Public Access—Author Manuscript—12 pages).
Fung et al. (2009) "Development of a creatinine enzyme-based bar-code-style lateral-flow assay," *Analytical and Bioanalytical Chemistry*, 393(4): 1281-1287.
Fung et al. (2009) "Development of enzyme-based bar code-style lateral-flow assay for hydrogen peroxide determination," *Anal Chim Acta*. 634(1): 89-95.

(56) References Cited

OTHER PUBLICATIONS

GCA Saliva-Check Mutans product sheet. 2011. http://www.gcamerica.com/storage/dps_c/GCA_SALIVA-CHECK_MUTANS-iPad.pdf retrieved Sep. 21, 2019.
Jue et al. (2014) "Simultaneous Concentration and Detection of Biomarkers on Paper," published document for the Capstone Design team, *MicroTAS Annual Meeting, San Antonio, Texas*, 7 pages.
Jue et al. (2014) "Using an aqueous two-phase polymer-salt system to rapidly concentrate viruses for improving the detection limit of the lateral-flow immunoassay," *Biotechnology and Bioengineering* 111(12): 2499-2507.
Jue et al. "Simultaneous Concentration and Detection of Biomarkers on Paper," document submitted but not published, UCLA, 23 pages.
Kim, et al. (2013) "Image Analysis of a Lateral Flow Strip Sensor for the Detection of *Escherichia coli* 0157:H7," *J. of Biosystems Eng*. 38(4):335-340.
Leung et al. (2008) "InfectCheck CRP barcode-style lateral flow assay for semi-quantitative detection of C-reactive protein in distinguishing between bacterial and viral infections," *J Immunol Meth*. 336(1): 30-36.
Luo, et al. (2005) "PDMS microfludic device for optical detection of protein immunoassay using gold nanoparticles." *Lab on a Chip* 5:726-729.
Mashayekhi et al. (2009) "Concentration of mammalian genomic DNA using two-phase aqueous micellar systems," *Biotechnology and Bioengineering* 102(6): 1613-1623, publ online Nov. 3, 2008, publ in journal Apr. 15, 2009.
Mashayekhi et al. (2010) "Enhancing the lateral-flow immunoassay for viral detection using an aqueous two-phase micellar system," *Anal. Bioanal. Chem*. 398(7): 2955-2961.
Mashayekhi et al. (2012) "Enhancing the lateral-flow immunoassay for detection of proteins using an aqueous two-phase micellar system," *Anal. Bioanal. Chem*. 404: 2057-2066.
McCudden et al. (2012) "Evaluation of high resolution gel beta 2-transferrin for detection of cerebrospinal fluid leak," *Clinical Chemistry and Laboratory Medicine* 6 pages [Abastract].
McCudden et al. (2013) "Evaluation of high resolution gel β2-transferrin for detection of cerebrospinal fluid leak." *Clin. Chem. Lab. Med*., 51(2): 311-315, CCLM / FESCC. 0. 1-5. 10.1515/cclm-2012-0408.
NIH Small Business Technology Transfer Grant Application, Proposal to improve healthcare of tooth decay by developing a point-of-care (POC) diagnostic device, 6 pages, submitted Nov. 19, 2014.
Pereira et al. (2014) "Enhancing the phase separation behavior of a micellar aqueous two-phase system in a paper-based diagnostic," *The Annual UC System wide Bioengineering Symposium, Irvine, California*, poster, 1 page.
Pereira et al. (2014) "Enhancing the phase separation behavior of a micellar aqueous two-phase system in a paper-based diagnostic," *UC Bioengineering Symposium 2014*, Abstract, 2 pages.
Pereira et al. (2014) "Paper-based diagnostic accelerates phase separation of a micellar aqueous two-phase system," *The Biomedical Engineering Society Annual Meeting, San Antonio, Texas*, poster, 1 page.
Pereira et al. (2015) "Improving malaria biomarker detection and accelerating micellar two-phase separation with a paper-based diagnostic," *Department of Engineering, UCLA 90095, UCLA Tech Forum*, abstract, 1 page.
Pereira et al. (2015) "Improving malaria biomarker detection and accelerating micellar two-phase separation with a paper-based diagnostic," *The UCLA Engineering Tech Forum, Los Angeles, California*, poster, 1 page.
Pereira et al. (2015) "Single-step, paper-based concentration and detection of a malaria biomarker," *Analytica Chimica Acta* 882: 83-89.
Pereira et al. "Paper-based diagnostic accelerates phase separation of a micellar aqueous two-phase system," *Department of Engineering, University of California, Los Angeles*, abstract, 2 pages.
Phase Diagnostics, Business Plan, *OneStart Competition* 2015, May 2015, 12 pages.
Sampaio et al. (2009) "Predictability of quantification of beta-trace protein for diagnosis of cerebrospinal fluid leak: Cutoff determination in nasal fluids with two control groups." *Am. J. Rhinol. Allerg*. 23(6): 585-590.
Song, et al. (2016) "Instrument-Free Point-of-Care Molecular Detection of Zika Virus." *Analytical Chemistry* 88: 7289-7294.
Wong et al. (2015) "Direct Reading of Bona Fide Barcode Assays for Diagnostics with Smartphone Apps," *Scientific Reports* 5, Article No. 11727 (11 pages).
Wu et al. (Jul. 21, 2014) "Research highlights: increasing paper possibilities" *Lab on a Chip*, 14(17) 3258-3261.
Yu, et al. (2009) "Flow-through functionalized PDMS microfluidic channels with dextran derivative for ELISAs." *Lab on a Chip* 9:1243-1247.
EP Extended Search Report dated Mar. 23, 2021 issued in EP 20200335.6.
KR Office Action dated Mar. 22, 2021 issued in KR 10-2016-7027705.
CN Second Office Action dated Feb. 20, 2021 issued in CN 201680059385.6.
JP Office Action dated Sep. 7, 2020 issued in JP 2018-511707.
EP Office Action dated Oct. 6, 2020 issued in EP 17810966.6.
EP Extended Supplementary Search Report dated Jan. 27, 2021 issued in EP 18809609.3.
U.S. Final Office Action dated Jun. 4, 2020 issued in U.S. Appl. No. 15/756,542.
U.S. Office Action dated Jan. 21, 2021 issued in U.S. Appl. No. 15/756,542.
U.S. Office Action dated Oct. 27, 2020 issued in U.S. Appl. No. 16/498,312.
Koczula, et al. (2016) "Lateral flow assays." *Essays in Biochemistry* 60: 111-120.
Mosley G. et al. (2017) "Improved lateral-flow immunoassays for chlamydia and immunoglobulin M by sequential rehydration of two-phase system components within a paper-based diagnostic" *Mikrochimica Acta* 184(10): 4055-4064.
Risch, et al. (2005) "Rapid, accurate and non-invasive detection of cerebrospinal fluid leakage using combined determination of β-trace protein in secretion and serum" *Clinica Chimica Acta* 351: 169-176.
AU Examination report No. 1 dated May 24, 2021 issued in AU 2020201579.
AU Office Action dated Nov. 4, 2021 issued in AU 2016318103.
CN Third Office Action dated Jun. 22, 2021 issued in CN 201680059385.6.
JP 2nd Office Action dated August 30, 2021 issued in JP 2018-511707.
EP 2nd Office Action dated Jul. 27, 2021 issued in EP 17810966.6.
JP Office Action dated May 17, 2021 issued in JP 2018-564267.
KR Office Action dated Aug. 23, 2021 issued in KR 10-2019-7000413.
U.S. Final Office Action dated Jun. 1, 2021 issued in U.S. Appl. No. 15/756,542.
U.S. Office Action Advisory Action dated Aug. 20, 2021 issued in U.S. Appl. No. 15/756,542.
U.S. Office Action Advisory Action (second) dated Sep. 17, 2021 issued in U.S. Appl. No. 15/756,542.
U.S. Notice of Allowance dated Nov. 16, 2021 issued in U.S. Appl. No. 15/756,542.
U.S. Office Action dated Jun. 9, 2021 issued in U.S. Appl. No. 16/307,125.
U.S. Final Office Action dated May 17, 2021 issued in U.S. Appl. No. 16/498,312.
U.S. Notice of Allowance dated Aug. 23, 2021 issued in U.S. Appl. No. 16/498,312.

* cited by examiner

HYDROGEL PLATFORM FOR AQUEOUS TWO-PHASE CONCENTRATION OF A TARGET TO ENHANCE ITS DETECTION

CROSS-REFERENCE TO RELATED APPLICATIONS

This application is a U.S. 371 National Phase of PCT/US2017/047849, filed on Aug. 21, 2017, which claims benefit of and priority to U.S. Ser. No. 62/483,221, filed on Apr. 7, 2017, and to U.S. Ser. No. 62/378,087, filed on Aug. 22, 2016, all of which are incorporated herein by reference in their entirety for all purposes.

STATEMENT OF GOVERNMENTAL SUPPORT

[Not Applicable]

BACKGROUND

Assays have been used to detect the presence or the concentration of various substances or pathogens in biological fluids. In a solid phase immunoassay, a receptor, typically an antibody which is specific for the ligand to be detected, is immobilized on a solid support. A test fluid that may comprise the analyte to be detected is contacted with the solid support, and a receptor-analyte pair is formed when the target analyte is present. In order to make the receptor-ligand pair visible, labeled antibodies may be used that bind to the receptor-ligand pair followed by visual detection of the labeled antibody bound to the receptor-ligand pair.

The most commercialized point-of-care diagnostic device is the lateral-flow immunoassay (LFA), due to its low cost and simplicity. In typical so-called lateral-flow assays, a fluid potentially containing the analyte to be detected is applied to one end of a porous membrane layer and flows in a lateral direction through the membrane under the action of capillary forces, and an analyte in the fluid is to be bound and captured by an immobilized "receptor". LFAs often incorporate a so-called sandwich immunoassay, in which the analyte is sandwiched between a labeled antibody and an antibody immobilized on a solid support.

The LFA, however, suffers from an inferior sensitivity when compared to laboratory-based assays, such as ELISA. While there has been significant effort put forth to improve LFA sensitivity, many of these approaches have relied on the use of expensive, electronic readers or required multiple user steps which detract from the point-of-care nature of the LFA.

Similarly, while efforts have been made to design point-of-care friendly nucleic acid amplification tests (NAATs) for DNA detection, these often either lack sensitivity due to over-simplification, or sacrifice ease-of-use to retain test accuracy. Moreover, current point-of-care (POC) NAATs still typically require equipment to analyze and process samples. Thus, there are no commercialized POC NAATs that are entirely stand-alone or portable.

SUMMARY

It was discovered that hydrogel scaffolds can be used to induce phase separation as aqueous two-phase systems (ATPSs) pass through and/or rehydrate the scaffolds, allowing for concentration of target analyte(s) (e.g., biomolecule(s)) into a particular phase of the ATPS, and that phase can end up as the leading front. Accordingly, in various embodiments, methods and devices are provided that utilize aqueous two-phase systems and hydrogel scaffolds to improve the sensitivity of assays (e.g., of point-of-care assays) without sacrificing cost or ease of use. The two-phase components are relatively inexpensive, and the analyte-concentrating process via phase separation can take place in minutes or less when facilitated by dehydrated hydrogels. Therefore, biomarker concentration and detection can occur seamlessly with little to no additional user steps.

Various embodiments contemplated herein may include, but need not be limited to, one or more of the following:

Embodiment 1

A system for the separation and/or concentration of an analyte, said system comprising:

an aqueous two-phase system (ATPS) comprising a mixed phase solution that separates into a first phase solution and a second phase where, in use, said first phase solution becomes a leading phase and said second phase solution becomes a lagging phase; and a hydrogel where said hydrogel and ATPS are disposed to permit said ATPS to flow through said hydrogel.

Embodiment 2

The system of embodiment 1, wherein said system is configured so the hydrogel is substantially dry and is rehydrated as the ATPS flows through said hydrogel.

Embodiment 3

The system of embodiment 1, wherein said hydrogel is hydrated prior to passage of said ATPS through said hydrogel.

Embodiment 4

The system according to any one of embodiments 1-3, wherein said hydrogel comprises a naturally-occurring polymer.

Embodiment 5

The system according to any one of embodiments 1-3, wherein said hydrogel comprises a synthetic polymer.

Embodiment 6

The system according to any one of embodiments 1-5, wherein said hydrogel comprises a hydrogel selected from the group consisting of polyethylene glycol hydrogels, polyethylene oxide hydrogels, polyphosphazene hydrogels, collagen hydrogels, polysaccharide hydrogels, hydroxyethyl methacrylate hydrogels, acrylic hydrogels, copolymers of polyoxyethylene/polyoxypropylene/polyoxyethylene hydrogels, alginate hydrogels, gelatin based hydrogels, chitosan based hydrogels, dextran-aldehyde conjugate hydrogels, hyaluronan/gelatin hydrogels, acrylamide/itaconic acid copolymer hydrogels, acrylic hydrogels, nanometal hydroxide hydrogels, poly(N-vinyl pyrrolidone) hydrogels, poly(N-isopropylacrylamide) hydrogels, collagen-chondroitin sulfate hyaluronic acid hydrogels, polyacrylic acid hydrogels, polyvinyl alcohol hydrogels.

Embodiment 7

The system according to any one of embodiments 1-3 and 5, wherein said hydrogel comprises a hydrogel that is a PEGDMA or a PEGUDM hydrogel.

Embodiment 8

The system of embodiment 7, wherein said hydrogel comprises polyethylene glycol dimethacrylate.

Embodiment 9

The system according to any one of embodiments 1-8, wherein said hydrogel is a hydrogel formed using a porogen.

Embodiment 10

The system of embodiment 9, wherein said hydrogel is formed using a porogen selected from the group consisting of salt crystals, beads, sodium bicarbonate, sugars, paraffin, and gelatin.

Embodiment 11

The system of embodiment 9, wherein said hydrogel is formed using a porogen that comprises a salt.

Embodiment 12

The system according to any one of embodiments 1-11, wherein said ATPS is selected from the group consisting of a polymer/salt ATPS, a polymer/polymer ATPS, a micellar/polymer ATPS, a micellar ATPS, a micellar/salt ATPS, a micellar/sugar ATPS, and an ionic liquid/salt ATPS.

Embodiment 13

The system of embodiment 12, wherein a first phase of solution of said ATPS comprises a Component 1 of Table 1 and a second phase solution of said ATPS comprises a Component 2 of Table 1.

Embodiment 14

The system of embodiment 12, wherein said ATPS is a polymer/salt ATPS.

Embodiment 15

The system of embodiment 14, wherein said ATPS is a PEG/salt ATPS.

Embodiment 16

The system of embodiment 15, wherein said ATPS is a PEG/potassium phosphate ATPS.

Embodiment 17

The system of embodiment 12, wherein said ATPS is a micellar ATPS.

Embodiment 18

The system of embodiment 17, wherein said ATPS is a surfactant/salt ATPS.

Embodiment 19

The system of embodiment 18, wherein said ATPS comprises Triton X-114 (TX-114) surfactant and potassium phosphate salt.

Embodiment 20

The system of embodiment 17, wherein said ATPS comprises a surfactant.

Embodiment 21

The system of embodiment 20, wherein said ATPS comprises TX-114.

Embodiment 22

The system of embodiment 12, wherein said ATPS comprises polypropylene glycol.

Embodiment 23

The system of embodiment 12, wherein said ATPS is a micellar/polymer ATPS.

Embodiment 24

The system of embodiment 23, wherein said ATPS comprises Triton X-100 and dextran.

Embodiment 25

The system of embodiment 12, wherein said ATPS is a micellar/sugar ATPS.

Embodiment 26

The system of embodiment 25, wherein said ATPS comprises Triton X-100 and sucrose.

Embodiment 27

The system of embodiment 12, wherein said ATPS is an ionic liquid ATPS.

Embodiment 28

The system of embodiment 27, wherein said ATPS comprises 1-Butyl-3-methylimidazolium tetrafluoroborate ([BMIM][BF4]).

Embodiment 29

The system according to any one of embodiments 1-28, wherein said system is configured to concentrate an analyte in a leading phase of said ATPS.

Embodiment 30

The system according to any one of embodiments 1-28, wherein said system is configured to concentrate an analyte in a trailing phase of said ATPS.

Embodiment 31

The system according to any one of embodiments 1-28, wherein said system is configured to concentrate an analyte at an interface between a leading phase and a trailing phase of said ATPS.

Embodiment 32

An assay device for the detection and/or quantification of an analyte in a sample, said device comprising:

a concentration component comprising a hydrogel configured to receive and/or contain an ATPS; and a detection component configured to detect and/or quantify an analyte separated and/or concentrated by said concentration component.

Embodiment 33

The device of embodiment 32, wherein said hydrogel is hydrated prior to contact with an ATPS.

Embodiment 34

The device of embodiment 32, wherein said hydrogel is dried and configured to hydrate on contact with an ATPS.

Embodiment 35

The device according to any one of embodiments 32-34, wherein said device comprises a lateral flow assay (LFA) or a flow-through (spot) assay.

Embodiment 36

The device of embodiment 35, wherein said device comprises a lateral flow assay (LFA).

Embodiment 37

The device of embodiment 36, wherein said lateral-flow assay comprises a porous matrix disposed in fluid communication with said hydrogel so that a fluid in said hydrogel can pass into said porous matrix.

Embodiment 38

The device according to any one of embodiments 36-37, wherein said concentration component, when in use, comprises a system according to any one of embodiment 1-31.

Embodiment 39

The device according to any one of embodiments 36-38, wherein said lateral-flow assay comprises a probe and/or a development reagent.

Embodiment 40

The device of embodiment 39, wherein said lateral-flow assay comprises probe and a development reagent and is configured so that in use said probe associates said development reagent to enhance a signal.

Embodiment 41

The device according to any one of embodiments 37-40, wherein said porous matrix is configured to receive and/or contain an ATPS or components thereof and/or said probe, and/or said development reagent.

Embodiment 42

The device according to any one of embodiments 36-41, wherein said LFA comprises a conjugate pad, a test line comprising an antibody that binds said analyte, optionally a control line comprising a secondary antibody, optionally an absorbent pad, and optionally a sample pad.

Embodiment 43

The device of embodiment 35, wherein said device comprises a flow-through (spot) assay.

Embodiment 44

The device of embodiment 43, wherein said device comprises a detection component disposed beneath said concentration component and in fluid communication with said hydrogel so that a fluid in said hydrogel can pass into said detection component.

Embodiment 45

The device according to any one of embodiments 43-44, wherein said concentration component, when in use, comprises a system according to any one of embodiments 1-31.

Embodiment 46

The device according to any one of embodiments 43-45, wherein said flow-through assay comprises a probe and/or a development reagent.

Embodiment 47

The device of embodiment 46, wherein said flow-through assay comprises a probe and a development reagent where said device is configured so that in use said probe associates with said development reagent to enhance a signal.

Embodiment 48

The device according to any one of embodiments 43-47, wherein said detection component comprises a conjugate pad, a reaction pad, and optionally a sink.

Embodiment 49

The device according to any one of embodiments 32-48, wherein said probe is disposed in said ATPS.

Embodiment 50

The device of embodiment 49, wherein said probe is associated with a leading phase solution of said ATPS.

Embodiment 51

The device according to any one of embodiments 32-50, wherein said development reagent is disposed in said ATPS.

Embodiment 52

The device according to any one of embodiments 32-51, wherein said development reagent is disposed in LFA or flow through assay prior to contact with said ATPS.

Embodiment 53

The device of embodiment 51, wherein said development reagent is associated with said second phase solution of said ATPS.

Embodiment 54

The device according to any one of embodiments 32-53, wherein said device is configured for said ATPS to be combined with said sample before application to said device.

Embodiment 55

The device according to any one of embodiments 32-54, wherein said probe is dehydrated in the hydrogel of said concentration component.

Embodiment 56

The device according to any one of embodiments 32-54, wherein said probe is dehydrated in the detection component of the lateral-flow assay or the flow-through assay.

Embodiment 57

The device according to any one of embodiments 32-56, wherein said development reagent is dehydrated on the lateral-flow assay or the flow-through assay before the device is contacted with the sample.

Embodiment 58

The device according to any one of embodiments 32-57, wherein said probe is selected to extremely partition into a hydrophilic phase of said ATPS.

Embodiment 59

The device according to any one of embodiments 32-58, wherein said development reagent is selected to extremely partition into a hydrophobic phase of said ATPS.

Embodiment 60

The device according to any one of embodiments 32-59, wherein said probe comprises a binding moiety that binds to said target analyte.

Embodiment 61

The device of embodiment 60, wherein said target analyte comprises a moiety selected from the group consisting of a protein, a nucleic acid, a sugar or lectin, and a microorganism.

Embodiment 62

The device of embodiment 61, wherein said target analyte comprises a microorganism selected from the group consisting of a bacterium, a protozoan, a fungus, a virus, and an alga.

Embodiment 63

The device of embodiment 61, wherein said target analyte comprises a biomarker for a microorganism.

Embodiment 64

The device of embodiment 63, wherein said target analyte comprises a biomarker for a microorganism selected from the group consisting of a bacterium, a protozoan, a fungus, a virus, and an alga.

Embodiment 65

The device of embodiment 63, wherein said target analyte comprises a biomarker for a disease condition, a biomarker for food safety (or hazard), or a biomarker for a bioterror agent.

Embodiment 66

The device according to any one of embodiments 60-65, wherein said binding moiety is selected from the group consisting of an antibody or antibody fragment, a lectin, a nucleic acid, and an aptamer.

Embodiment 67

The device of embodiment 66, wherein said probe comprises an antibody or an antibody fragment.

Embodiment 68

The device according to any one of embodiments 32-67, wherein said probe comprises a material selected from the group consisting of a synthetic polymer, a metal, a mineral, a glass, a quartz, a ceramic, a biological polymer, and a plastic.

Embodiment 69

The device of embodiment 68, wherein said probe comprises a material selected from the group consisting of polyethylene, polypropylene, cellulose, chitin, nylon, polyoxymethylene, polytetrafluoroethylene, or polyvinyl chloride, dextran, polypropylene, or polyethylene glycol.

Embodiment 70

The device of embodiment 68, wherein said probe comprises a metal selected from the group consisting of gold, silver, iron, platinum, and titanium.

Embodiment 71

The device according to any one of embodiments 32-70, wherein said probe comprises a nanoparticle.

Embodiment 72

The device according to any one of embodiments 32-71, wherein said probe comprises an agent that can react with said development reagent to produce a detectable signal.

Embodiment 73

The device of embodiment 72, wherein said agent comprises an enzyme that reacts with a substrate to form a strong visible signal.

Embodiment 74

The device of embodiment 73, wherein said development reagent comprises said substrate.

Embodiment 75

The device of embodiment 73, wherein said development reagent comprises an antibody that binds said enzyme.

Embodiment 76

The device of embodiment 72, wherein said agent comprises a substrate that reacts with an enzyme to form a strong visible product.

Embodiment 77

The device of embodiment 76, wherein said development reagent comprises said enzyme.

Embodiment 78

The device according to any one of embodiments 73 and 77, wherein said enzyme is selected from the group consisting of alkaline phosphatase, horse radish (or other) peroxidase, and glucose oxidase.

Embodiment 79

The device according to any one of embodiments 32-78, wherein said probe comprises a coating that has an affinity for the first phase solution or the second phase solution of said ATPS.

Embodiment 80

The device of embodiment 79, wherein said coating comprises a material selected from the group consisting of polypropylene glycol, polyethylene glycol, dextran, a hydrophilic protein, and a hydrophobic protein.

Embodiment 81

The device according to any one of embodiments 32-80, wherein said device comprises two or more probes that each interact with different analytes.

Embodiment 82

The device of embodiment 81, wherein said device includes at least two different probes, or at least 3 different probes, or at least 4 different probes, or at least 5 different probes, or at least 7 different probes, or at least 10 different probes, or at least 15 different probes, or at least 20 different probes.

Embodiment 83

The device according to any one of embodiments 32-82, wherein said device is configured to perform a competitive assay.

Embodiment 84

The device according to any one of embodiments 32-82, wherein said device is configured to perform a sandwich assay.

Embodiment 85

A method of separating and/or concentrating an analyte, said method comprising:

applying a sample comprising said analyte to a system according to any one of embodiments 1-31;

permitting said ATPS to pass through said hydrogel thereby concentrating said analyte into a phase of said ATPS or concentrating said analyte into an interface between two phases of said ATPS.

Embodiment 86

A method of detecting and/or quantifying an analyte, said method comprising:

applying a sample comprising said analyte to a device according to any one of embodiments 32-84 where, in the presence of said analyte, said detection component produces a signal indicating the presence of said analyte; and detecting and/or quantifying said signal to indicate the presence and/or quantity of said analyte in said sample.

Embodiment 87

The method of embodiment 86, wherein said LFA or flow-through assay is one in which a binding moiety captures said analyte and in which a detection probe binds to said captured analyte.

Embodiment 88

The method according to any one of embodiments 86-87, wherein said target analyte comprises a moiety selected from the group consisting of a protein, a nucleic acid, a sugar or lectin, and a microorganism.

Embodiment 89

The method of embodiment 88, wherein said target analyte comprises a microorganism selected from the group consisting of a bacterium, a protozoan, a fungus, a virus, and an alga.

Embodiment 90

The method of embodiment 88, wherein said target analyte comprises a biomarker for a microorganism.

Embodiment 91

The method of embodiment 90, wherein said target analyte comprises a biomarker for a microorganism selected from the group consisting of a bacterium, a protozoan, a fungus, a virus, and an alga.

Embodiment 92

The method of embodiment 88, wherein said target analyte comprises a biomarker for a disease condition, a biomarker for food safety (or hazard), or a biomarker for a bioterror agent.

Embodiment 93

A kit for the detection and/or quantification of an analyte, said kit comprising:

a device according to any one of embodiments 32-84; and a collection device for collecting a sample.

Embodiment 94

The kit of embodiment 93, wherein said collection device comprises a device for collecting oral fluid.

Embodiment 95

The kit of embodiment 93, wherein said collection device comprises a device for collecting blood.

Embodiment 96

The kit of embodiment 93, wherein said collection device comprises a urine collection device.

Embodiment 97

The kit of embodiment 93, wherein said collection device comprises a device for collecting vaginal fluid or from an endocervical swab.

Embodiment 98

The kit of embodiment 93, wherein said collection device comprises a device for an environmental sample.

Embodiment 99

A smartphone configured for the detection and/or quantification of an analyte in an assay detection component, said smartphone comprising:

a smartphone comprising a camera; and a smartphone attachment said attachment comprising:
  - a region for receiving an assay detection component;
  - a light source that illuminates said detection component when said detection component is present in said attachment; and
  - an optical path that transmits images of said detection component or regions thereof to said camera.

Embodiment 100

The smartphone of embodiment 99, wherein said light source comprises a light emitting diode (LED).

Embodiment 101

The smartphone according to any one of embodiments 99-100 wherein a diffuser is disposed between said light source and said detection component.

Embodiment 102

The smartphone according to any one of embodiments 99-101, wherein a lens is disposed between said detection component and said camera.

Embodiment 103

The smartphone according to any one of embodiments 99-102, wherein said attachment is configured to transmit illumination through said detection component and into said optical path.

Embodiment 104

The smartphone according to any one of embodiments 99-102, wherein said attachment is configured to reflect illumination from a surface of said detection component and into said optical path.

Embodiment 105

The smartphone according to any one of embodiments 99-104, wherein said smartphone is configured to obtain a control image of a control detection component lacking the analyte to be detected.

Embodiment 106

The smartphone according to any one of embodiments 99-105, wherein said smartphone is configured to obtain a test image of a test detection component containing the analyte to be detected.

Embodiment 107

The smartphone according to any one of embodiments 105-106, wherein said smartphone is configured to detect the centroids of the signal(s) in the acquired control and/or test images.

Embodiment 108

The smartphone of embodiment 107, wherein said smartphone is configured to extract pixel information from a pixel box disposed around said centroid(s).

Embodiment 109

The smartphone of embodiment 108, wherein said pixel box ranges from about 50 or from about 100, or from about 150, or from about 200 or from about 250, or from about 300 pixels by from about 50 or from about 100, or from about 150, or from about 200 or from about 250, or from about 300 pixels around said centroids.

Embodiment 110

The smartphone of embodiment 108, wherein said pixel box by pixel box is about 200×200 pixels.

Embodiment 111

The smartphone according to any one of embodiments 99-110, wherein said smartphone is configured to determine the relative absorbance of the analyte bound in the detection component.

Embodiment 112

The smartphone of embodiment 111, wherein said smartphone is configured to determine relative absorbance as $$A_{anal} = \log\left(\frac{I_{control}}{I_{test}}\right)$$

wherein $A_{anal}$ is the relative absorbance of bound analyte in the sample, $I_{control}$ is the signal intensity from the control sample, and $I_{test}$ is the signal intensity from the test sample.

Embodiment 113

The smartphone according to any one of embodiments 99-112, wherein said smartphone is configured to prompt a user to identify one or more analytes for detection.

Embodiment 114

The smartphone according to any one of embodiments 99-113, wherein said smartphone is configured to provide a calibration curve for the analyte(s) to be detected.

Embodiment 115

The smartphone of embodiment 114, wherein said smartphone is configured to calculate the analyte concentration from said calibration curve.

Embodiment 116

The smartphone of embodiment 99-115, wherein said smartphone is configured to calculate the analyte concentration as:

$$A_{anal} = \varepsilon C_{anal} L \Rightarrow C_{anal} = \frac{A_{anal}}{\varepsilon L}$$

wherein $A_{anal}$ is the relative absorbance of bound analyte, $\varepsilon L$ is a calibration factor, and $C_{anal}$ is the concentration of analyte.

Embodiment 117

An assay system for the detection and/or quantification of an analyte in a sample, said system comprising: a concentration component comprising a hydrogel configured to receive and/or contain an ATPS; and a detection component configured to detect and/or quantify an analyte separated and/or concentrated by said concentration component.

Embodiment 118

The system of embodiment 117, wherein said system further comprises a smartphone according to any one of embodiments 99-117.

Embodiment 119

The assay system according to any one of embodiments 117-118, wherein said concentration component comprises a system according to any one of embodiments 1-31.

Embodiment 120

The assay system according to any one of embodiments 117-119, wherein the said detection component comprises a device according to any one of embodiments 32-84.

Embodiment 121

The assay system according to any one of embodiments 117-120, wherein said detection component comprises a transparent or translucent polymeric material.

Embodiment 122

An assay system for the detection and/or quantification of an analyte in a sample, said system comprising: an assay device according to any one of embodiments 32-84; and a smartphone according to any one of embodiments 99-117.

Embodiment 123

The assay system according to any one of embodiments 117-122, wherein said detection component comprises a transparent or translucent polymeric material, or glass.

Embodiment 124

The assay systems of embodiment 123, wherein said detection component comprises a material selected from the group consisting of PDMS, PMMA, Thermoset Polyester (TPE), and Polyurethane Methacrylate (PUMA).

Embodiment 125

The assay systems of embodiment 123, wherein said detection component comprises PDMS.

Embodiment 126

The assay system according to any one of embodiments 117-125, wherein said detection component comprises moiety that competes for substrate binding with said analyte.

Embodiment 127

The assay system according to any one of embodiments 117-125, wherein said detection component comprise a moiety that binds said analyte.

Embodiment 128

The assay system of embodiment 127, wherein said moiety is an antibody or antibody fragment.

Embodiment 129

The assay system according to any one of embodiments 117-128, wherein said system is configured to detect and/or quantify Zika virus.

Embodiment 130

A method of separating and/or concentrating an analyte, said method comprising: applying a sample comprising said analyte to a system according to any one of embodiments 117-128; permitting said ATPS to pass through said hydrogel thereby concentrating said analyte into a phase of said ATPS or concentrating said analyte into an interface between two phases of said ATPS; disposing the ATPS phase or interface containing the analyte onto said detection component; and detecting and/or quantifying said analyte.

Embodiment 131

The method of embodiment 130, wherein said detecting and/or quantifying is performed using a smartphone according to any one of embodiments 99-117.

Embodiment 132

The method according to any one of embodiments 130-131, wherein said analyte comprise Zika virus or a component thereof.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "nucleic acid" or "oligonucleotide" or grammatical equivalents herein refer to at least two nucleotides covalently linked together. A nucleic acid of the present invention is preferably single-stranded or double-stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110: 4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. In addition, it is possible that nucleic acids of the present invention can alternatively be triple-stranded.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA,* 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv). However, alternative expression strategies have also been successful. For example, Fab molecules can be displayed on phage if one of the chains (heavy or light) is fused to g3 capsid protein and the complementary chain exported to the periplasm as a soluble molecule. The two chains can be encoded on the same or different replicons; the important point is that the two antibody chains in each Fab molecule assemble post-translationally, and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

An aptamer is an antibody-analogue formed from nucleic acids. An aptazyme is an enzyme analogue formed from nucleic acids. In particular, an aptazyme can function to change its configuration to capture a specific molecule, only in the presence of a second, specific analyte. Aptamers may not even require the binding of the first label to be detected in some assays, such as nano-CHEM-FET, where the reconfiguration would be detected directly.

The term "binding moiety", or a member of a "binding pair" refers to molecules that specifically bind other molecules, cells, microorganisms, and the like to form a binding complex such as antibody-antigen, lectin-carbohydrate, nucleic acid-nucleic acid, biotin-avidin, etc. Such binding moieties include, but are not limited to, monomeric or polymeric nucleic acids, aptamers, aptazymes, proteins, polysaccharides, sugars, lectins, and the like (see, e.g., Haugland, "Handbook of Fluorescent Probes and Research Chemicals" (Sixth Edition)), and any of the molecules capable of forming a binding pair as described above.

The phrase "specifically binds" indicates that the molecule binds preferentially to the target of interest or binds with greater affinity to the target (analyte) than to other molecules. For example, an antibody will selectively bind to the antigen against which it was raised. A DNA molecule will bind to a substantially complementary sequence and not to unrelated sequences under stringent conditions. Specific binding can refer to a binding reaction that is determinative of the presence of a target in a heterogeneous population of molecules (e.g., proteins and other biologics). Thus, under designated conditions (e.g. immunoassay conditions in the case of an antibody or stringent hybridization conditions in the case of a nucleic acid), the specific ligand or antibody binds to its particular "target" molecule and does not bind in a significant amount to other molecules present in the sample.

The term "small organic molecules" refers to molecules that are comparable in size to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term analyte refers to any moiety that is to be detected. Analytes include, but are not limited to particular biomolecules (proteins, antibodies, nucleic acids), bacteria or components thereof, viruses or components thereof (e.g., coat proteins), fungi or components thereof, protozoa or components thereof, drugs, toxins, food pathogens, and the like.

The term "paper", as used herein, is not limited to thin sheets from the pulp of wood or other fibrous plant substances although, in certain embodiments, the use of such papers in the devices described herein is contemplated. Papers more generally refer to porous materials often in sheet form, but not limited thereto that allow a fluid to flow through.

In some embodiments, the porous matrix is sufficiently porous to allow the mixed phase solution, first phase solution and/or second phase solution of an aqueous two-phase system (ATPS), and/or target analyte to flow through the LFA. In some embodiments, the porous matrix is sufficiently long and/or deep enough for the mixed phase solution, first phase solution and/or second phase solution, and/or target analyte to flow vertically and/or horizontally through the LFA or spot assay device. In some embodiments, the first phase solution flows through the porous matrix at a first rate and the second phase solution flows through the porous matrix at a second rate, where the first rate and the second rate are different. In some embodiments of the LFA or spot assay, the porous matrix comprises inter alia a material such as a sintered glass ceramic, a mineral, cellulose, a fiberglass, a nitrocellulose, polyvinylidene fluoride, a nylon, a charge modified nylon, a polyethersulfone, combinations thereof, and the like.

In some embodiments, the hydrogel is sufficiently porous to allow the mixed phase solution, first phase solution and/or second phase solution of an aqueous two-phase system (ATPS), and/or target analyte to flow through the hydrogel and, where desired, into a detection component (e.g., an LFA, a flow-through assay, etc.). In some embodiments, the hydrogel is sufficiently long and/or deep enough for the mixed phase solution, first phase solution and/or second phase solution, and/or target analyte to flow vertically and/or horizontally through the hydrogel. In some embodiments, the first phase solution flows through the hydrogel at a first rate, and the second phase solution flows through the hydrogel at a second rate, where the first rate and the second rate are different. In some embodiments of the aqueous two-phase system, the aqueous two-phase system is comprised of polyethylene glycol-salt, polypropylene-salt, polyethylene glycol-dextran, Triton X-114, or C10E4, as well as others. In some embodiments of the hydrogel, the hydrogel is comprised of polyethylene glycol dimethacrylate, polyacrylic acid, polyvinyl alcohol, or hyalauronic acid, as well as others. In some embodiments, the porogens used to make pores in the hydrogel are comprised of NaCl, polymethyl methacrylate beads, or polyethylene glycol, as well as others.

DETAILED DESCRIPTION

Figure 1A:
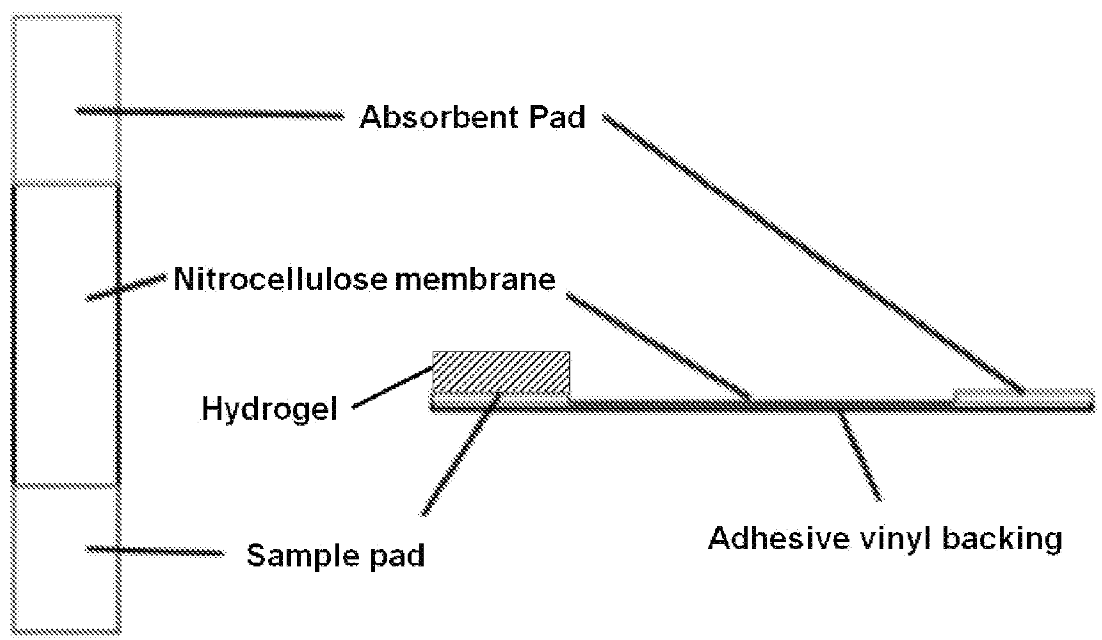
FIG. 1A shows a schematic of a lateral-flow immunoassay test strip integrated with a hydrogel.

Aqueous two-phase systems (ATPSs) have been used to concentrate biomarkers prior to detection using lateral-flow assay formats (see, e.g., PCT Publication No: WO 2015134938 (PCT/US2015/019297). In particular, it was discovered that the use of ATPSs to concentrate biomarkers, prior to detection with LFA, can provide 10-100 fold (or greater) improvement in the limit of detection over conventional LFA.

In an ATPS, analytes (e.g., biomolecules) may partition preferentially into one of the phases based primarily on excluded-volume and hydrophobic interactions with the components in each phase. Analytes that partition extremely into one phase can be concentrated by adjusting the volume ratio to decrease the volume of the phase containing the target. Additionally, for analytes that partition more evenly on their own, such as many proteins and small molecules, probes decorated with specific antibodies (e.g., functionalized gold nanoprobes (GNPs)) have been used to capture the target analyte (e.g., biomolecule) within the sample, and then partition extremely into one of the phases. These probes (e.g., GNPs) can then serve as colorimetric signal generators in the LFA. In addition to utilizing ATPSs that phase separate under stagnant conditions in a test tube, we have demonstrated that ATPSs can phase separate within a very short timescale as the solution flows through paper, allowing for simultaneous concentration and detection of a target biomolecule at the point-of-care. This technology significantly reduced the time required to concentrate a target biomolecule, as well as simplified the assay by eliminating user steps.

It was a surprising discovery that hydrogel scaffolds can be used to induce phase separation as ATPSs pass through and/or rehydrate the scaffolds, allowing for concentration of target analyte(s) (e.g., biomolecule(s)) into a leading front. When used in conjunction with any detection system, this pre-concentration step can lead to more a sensitive detection. Although this separation system can be integrated with a variety of detection systems, in certain embodiments, a lateral-flow immunoassay (LFA) or a flow-through (spot) test format provides the detection system.

Accordingly in various embodiments, the systems, methods, and devices described herein utilize hydrogel scaffolds (instead of paper or other media) to achieve ATPS phase separation and target analyte concentration. Prior to the experiments described herein, it was not clear if hydrogel scaffolds could enhance phase separation and target concentration. It was discovered that the porous network comprising a hydrogel can function in a manner similar to that of a paper to accelerate the coalescence of microscopic phase domains.

Additionally, 3D architecture has been found to affect fluid flow through the device. Paper, however, is limited in the shapes that can be formed, and it can be tedious to manually cut and assemble 3D paper structures. On the other hand, hydrogels can be easily formed into customized 3D configurations, offering greater versatility in controlling fluid flow as well as convenience and consistency in device fabrication. Additionally, hydrogels have easily tunable chemical and physical properties, that can be manipulated to enhance phase separation.

As demonstrated herein, phase separation of a mixed ATPS and the subsequent concentration of an analyte (e.g., a biomarker) can be achieved within lyophilized hydrogel scaffolds with pores on the micron scale. The feasibility of this system was demonstrated by using a polyethylene glycol dimethacrylate (PEGDMA) hydrogel system to induce phase separation of a polymer/salt ATPS comprised of polyethylene glycol (PEG) and potassium phosphate salt.

To make the gels, a precursor solution was formed containing PEGDMA, photoinitiator (Irgacure 2959), and filtered sodium chloride (NaCl) crystals as porogens. The precursor solution was transferred into a mold, and then placed under UV light to initiate crosslinking. The gels were then soaked overnight in deionized water to dissolve out the salt crystals, and lyophilized to form porous scaffolds.

Figure 3:
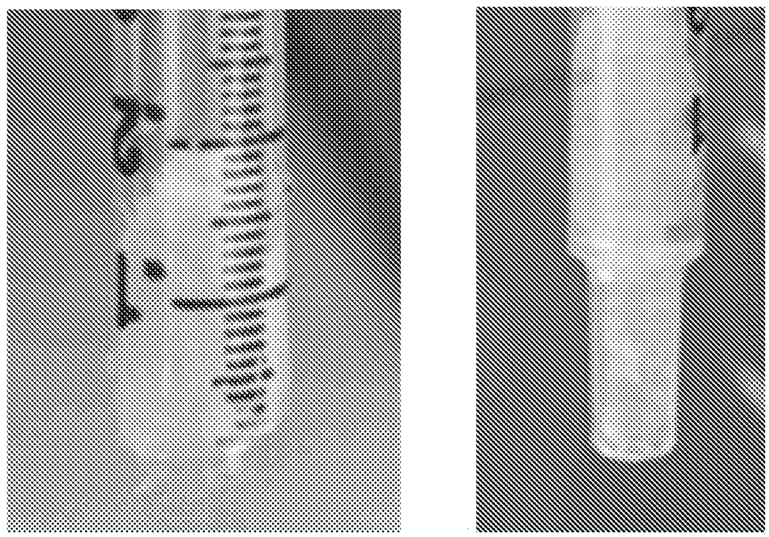
FIG. 3: Control solutions applied to hydrogel scaffolds. (Left) Solution of blue dye only; (Right) solution of BSA-GNs only.
Figure 4:
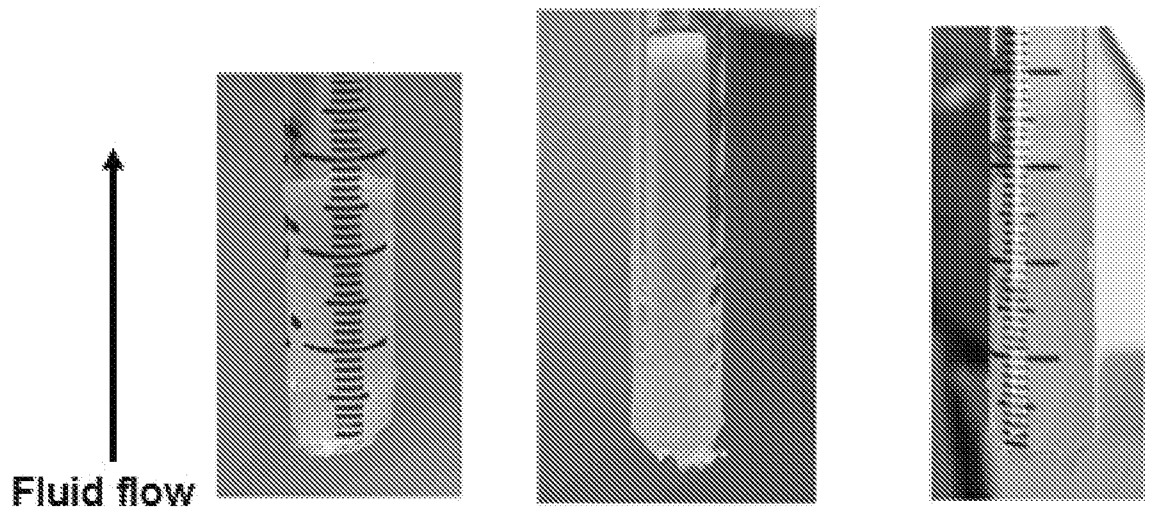
FIG. 4: ATPSs of various top phase to bottom phase volume ratios when applied to the hydrogel scaffold.
Figure 5:
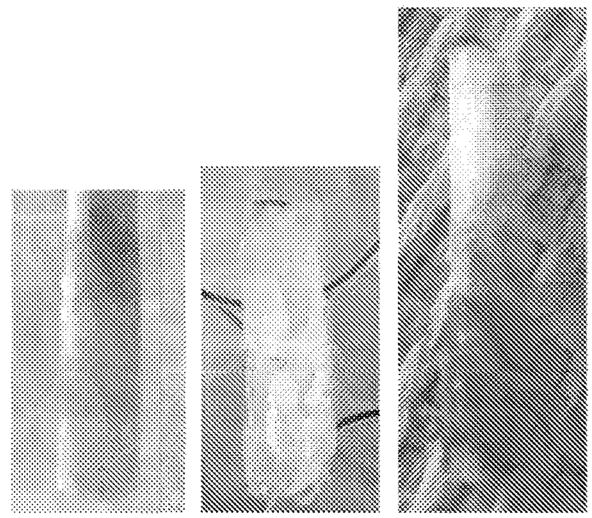
FIG. 5: Hydrogel-based phase separation achieved with a variety of two-phase systems. From left to right: Phase separation achieved with a Triton X-114 (TX-114) surfactant/salt system at room temperature, TX-114 system at 65° C., and polypropylene glycol-salt system at room temperature.

ATPS solutions were prepared with various concentrations of PEG and salt to form systems with different volume ratios of top phase to bottom phase (1:1, 6:1, 9:1 $V_{top}$:$V_{bottom}$). To visualize the phase separation, Brilliant Blue FCF dye was added to the system, as the hydrophobic dye molecules partition extremely into the more hydrophobic PEG-rich phase. Gold nanoparticles coated with bovine serum albumin (BSA-GNs), which are red in color, were also added to the system as they are driven out of the PEG-rich phase into the PEG-poor phase due to experiencing greater repulsive, excluded-volume interactions with the more abundant PEG molecules in the PEG-rich phase. Controls were performed, where water solutions containing only dye and only BSA-GNs, were flown up the strip. The color was found to be present evenly throughout the gel, indicating no concentration of either dye or BSA-GNs (FIG. 3). A dried hydrogel scaffold was then placed vertically into a well-mixed ATPS solution containing dye and BSA-GNs, and phase separation was observed as the fluid wicked up the gel. The red leading phase contained the concentrated gold nanoparticles, while the blue lagging phase contained the concentrated hydrophobic blue dye molecules. Macroscopic phase separation was visualized for several volume ratios (FIG. 4). The hydrogel scaffold was also found to induce phase separation of a variety of other ATPSs. For example, preliminary tests showed that phase separation of ATPSs consisting of (i) Triton X-114 (TX-114) surfactant and potassium phosphate salt at room temperature, (ii) TX-114 at 65° C., and (iii) polypropylene glycol at room temperature was also able to be induced on hydrogel scaffolds (FIG. 5).

Figure 6:
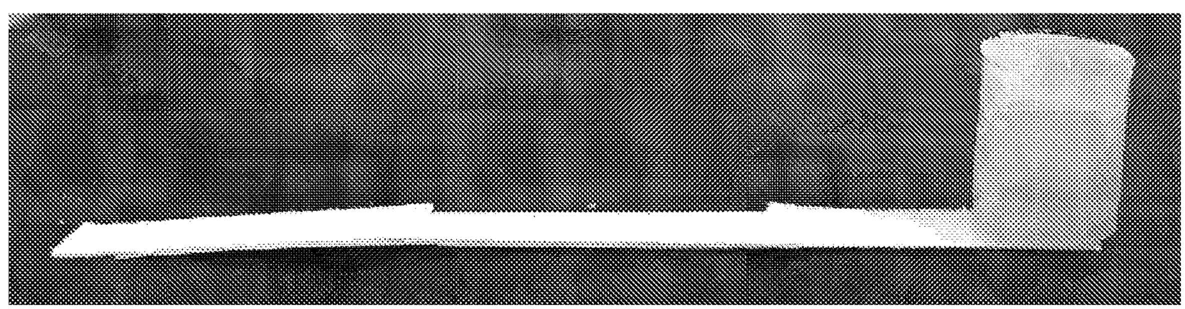
FIG. 6: One embodiment illustrating a design that integrates the hydrogel scaffold with the LFA. A sample mixed within an ATPS is applied to the dehydrated scaffold and phase separation is allowed to occur. Since, in the illustrated embodiment, the hydrogel sits on top of the LFA sample pad, the sample then travels from the hydrogel to the sample pad, and then finally to the detection region of the test strip.
Figure 7:
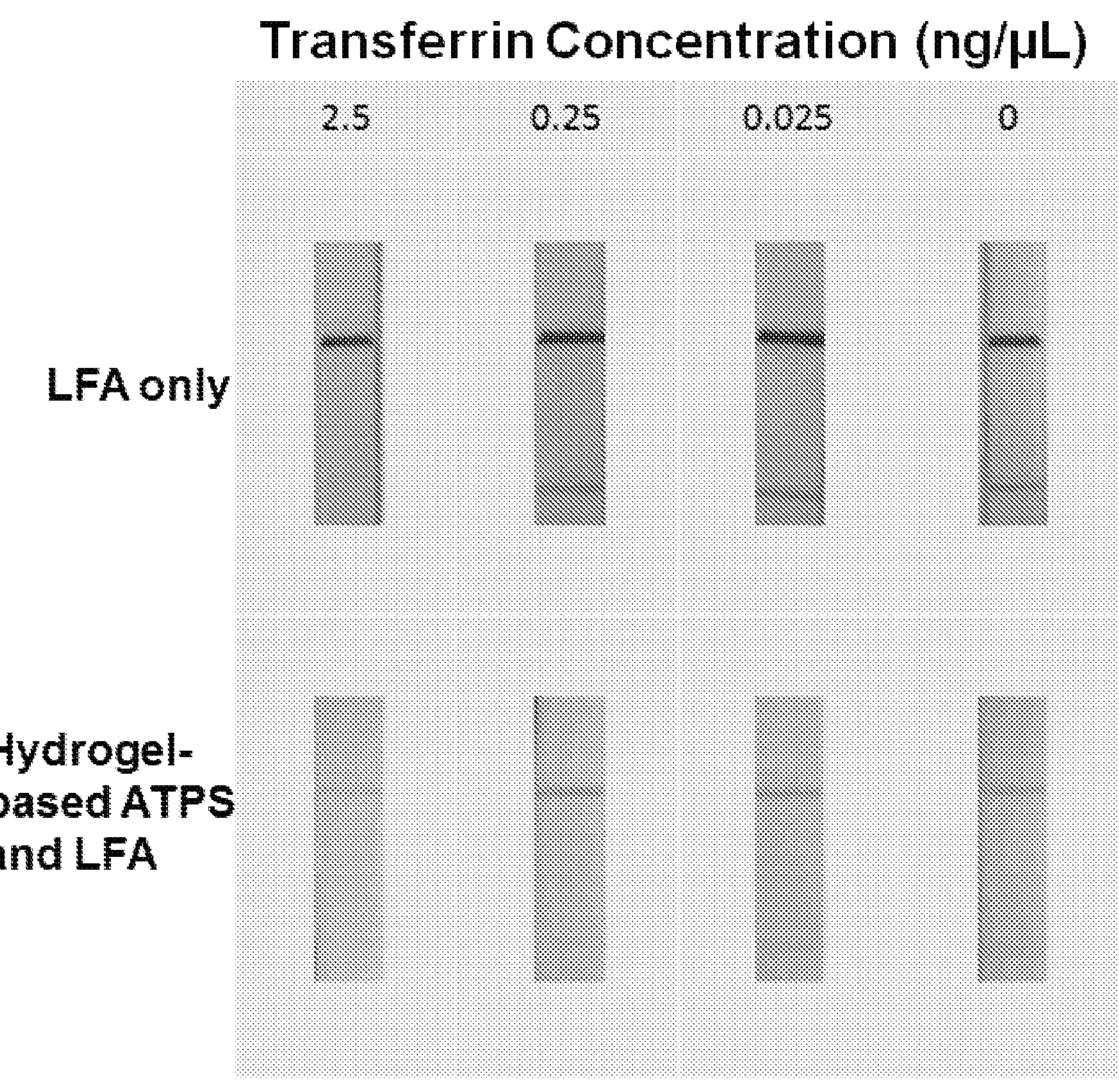
FIG. 7: Panel of LFA results comparing the detection limit of the conventional competitive LFA to the improved detection limit when combined with the hydrogel-based ATPS. The detection limit is designated as the lowest concentration that results in the absence of a lower test line. The test line appears at 0.25 ng/μL for the LFA only case, indicating a detection limit of 2.5 ng/μL. For the integrated hydrogel-ATPS-LFA system, the test line appears at 0.025 ng/μL, indicating a detection limit of 0.25 ng/μL.

In one illustrative, but non-limiting embodiment, to combine hydrogel two-phase concentration with LFA detection, a dry hydrogel scaffold was placed on top of the sample pad of an LFA (see, e.g., FIG. 6). In this proof-of-concept study, the model protein transferrin (Tf) was detected using a conventional LFA setup and then compared to a setup integrating hydrogel concentration of the target with LFA. GNPs were synthesized by conjugating gold nanoparticles with anti-Tf antibodies. A competitive LFA was utilized, in which the presence of the test line indicates a negative test result, while the absence of a test line indicates a positive test result. Using the conventional LFA setup, the detection limit was determined to be 2.5 ng/μL. Mixed ATPS solutions containing GNPs and various concentrations of Tf were then applied directly to the hydrogel scaffold. The target-bound GNPs were concentrated as they traveled through the gel, before reaching the test and control lines printed on the nitrocellulose membrane. Using this setup, the detection limit was determined to be 0.25 ng/μL, demonstrating a 10-fold improvement in detection over conventional LFA (FIG. 7). While we have demonstrated the feasibility of this system using a PEG-salt ATPS with gel scaffolds formed using PEGDMA and NaCl porogens, this technique can be applied to other ATPS systems (polypropylene-salt, PEG-dextran, TX-114, $C_{10}E_4$, etc.) and hydrogel systems (polyacrylic acid, polyvinyl alcohol, hyaluronic acid, etc.) and porogens (polymethyl methacrylate beads, polyethylene glycol, etc.).

The methods and systems described herein, can readily be extended to any detection method. For example, the methods and systems described herein can be used to improve laboratory-based tests for biomarker detection. Commercialized enzyme-linked immunosorbant assay (ELISA) kits typically require large volumes of reagents and many intermediate washing steps. Miniaturization of these immunoassay systems typically result in decreased signals that need to be amplified in some form. Hydrogel-based immunoassays can be mass produced as dry scaffolds with sizes small enough to fit in microarray formats. Furthermore, the unique use of hydrogel scaffolds as a matrix to enable target concentration via ATPS reduces the loss of signal that typically occurs with miniaturization. Therefore, with this technology, it is possible to achieve miniaturization of benchtop assays with the integration of inexpensive materials and less sample preparation.

In view of the foregoing, in certain embodiments, systems for the separation and/or concentration of an analyte are provided. In various embodiments the systems comprise an aqueous two-phase system (ATPS) comprising a mixed phase solution that separates into a first phase solution and a second phase where, in use, said first phase solution becomes a leading phase and said second phase solution becomes a lagging phase; and a hydrogel where said hydrogel and ATPS are disposed to permit the ATPS to flow through said hydrogel and achieve partial or full phase separation therein.

In various embodiments assay devices are also provided. In certain embodiments the assay devices comprise a concentration component comprising a hydrogel configured to receive and/or contain an ATPS (thereby forming a system for separation and/or concentration of an analyte as described herein), and a detection component configured to detect and/or quantify an analyte separated and/or concentrated by the concentration component. In certain embodiments the devices comprise a lateral flow assay (LFA) or a flow-through (spot) assay.

Also provided are methods of separating and/or concentrating an analyte using the systems described herein. Thus, for example, in certain embodiments a method of separating and/or concentrating an analyte, where the method comprises applying a sample comprising the analyte to a system comprising an ATPS and a hydrogel as described herein, and permitting the ATPS to pass through said hydrogel thereby concentrating the analyte into a phase of said ATPS or concentrating the analyte into an interface between two phases of said ATPS. In certain embodiments the sample is combined with the ATPS before application to the hydrogel. In other embodiments, the sample is applied to a hydrogel containing the ATPS.

In various embodiments methods of detecting and/or quantifying an analyte are provided. In certain embodiments the methods comprise applying a sample comprising said analyte to a device as described herein (e.g., a device comprising a hydrogel and/or a hydrogel/ATPS component) where, in the presence of said analyte, the detection component produces a signal indicating the presence of said analyte; and detecting and/or quantifying said signal to indicate the presence and/or quantity of said analyte in said sample.

Hydrogels to be Used in Combination with ATPS.

Any of a variety of hydrogels can be used in the methods, systems, and devices described herein. Hydrogels are polymer networks that, when hydrated, are extensively swollen with water (or other aqueous solutions). Typically a hydrogel is a polymeric material that exhibits the ability to swell and retain a significant fraction of water (or other aqueous solution) within its structure, but will not dissolve in water. Hydrogels are well known to those of skill in the art (see, e.g., Buchholz and Graham (1998) *Modern superabsorbent polymer technology*. New York: Wiley-VCH [chapters 1-7]; Brannon-Peppas and Harland (1991) *J. Controlled Release* 17(3): 297-298; Yuhui et al. (2013) *Adv. Funct. Mater.* 23(6): 660-672; Ahmed (2015) *J. Adv. Res.*, 6: 105-121, and the like).

The ability of hydrogels to absorb water typically arises from hydrophilic functional groups attached to the polymeric backbone, while their resistance to dissolution typically arises from cross-links between network chains. Many materials, both naturally occurring and synthetic, fit the definition of hydrogels. In certain embodiments hydrogels can be two- or multicomponent systems consisting of a three-dimensional network of polymer chains and water (or other aqueous solution) that fills the space between macromolecules.

Hydrogels can be synthesized in a number of "classical" chemical ways. These include one-step procedures like polymerization and parallel cross-linking of multifunctional monomers, as well as multiple step procedures involving synthesis of polymer molecules having reactive groups and their subsequent cross-linking, and/or also by reacting polymers with suitable cross-linking agents. One of skill in the art can routinely design and synthesize polymer networks with molecular-scale control over structure such as cross-linking density and with tailored properties, such as mechanical strength, characteristic pore size, and the like (see, e.g., (Burkert et al. (2007) *Radiat. Phys. Chem.* 76(8-9):1324-1328, and the like).

In certain embodiments the hydrogels comprise homopolymeric hydrogels derived from a single species of monomer and may have various cross-linked skeletal structures depending on the nature of the monomer and polymerization technique. In certain embodiments the hydrogels comprise copolymeric hydrogels comprised of two or more different monomer species. In certain embodiments such copolymeric hydrogels comprise at least one hydrophilic component, arranged in a random, block or alternating configuration along the chain of the polymer network (see, e.g., Yang et al. (2002) *Int. J. Pharm.* 235:1-15, and the like). In certain embodiments the hydrogels comprise (c) multipolymer interpenetrating polymeric hydrogels (IPN) that typically comprise two (or more) independent cross-linked synthetic and/or natural polymer components, contained in a network form. In certain embodiments the hydrogel comprises a semi-IPN hydrogel in which one component is a cross-linked polymer and the other component is a non-cross-linked polymer. In certain embodiments the hydrogels can comprise an amorphous (non-crystalline) hydrogel, or a semicrystalline hydrogel (e.g., a mixture of amorphous and crystalline phases, or a crystalline hydrogel).

Chemical or permanent hydrogels are typically formed by covalent crosslinking of polymers (Connell (1975) *J. Sci. Food and Agriculture,* 26(12): 1925-1929). One common way to create a covalently crosslinked network is to polymerize end-functionalized macromers (see, e.g., Liu et al. (2010) *Soft Matter.* 6(1):67-81; Miyata et al. (2002) *Adv. Drug Deliv. Rev.* 54: 79-98; Imamura et al. (1989) *J. Cardiac Surg.,* 4: 50-57). Hydrogels can be crosslinked with many compounds such as glutaraldehyde, formaldehyde, epoxy compounds, dialdehyde (see, e.g., Gulati et al. (2011) *Asian J. Pharmacy Life Sci.* 1(4): 2231-4423; Zhu (2010) *Biomaterials,* 31(17): 4639-4656; Ramamurthi and Vesely (2003) *J. Biomed. Mater. Res. A.* 2003; 66(2): 317-329; Denizli et al. (2004) *Polymer,* 45(19): 6431-6435; and the like), and other cross-linking reagents.

Hydrogels can be prepared from natural, synthetic or synthetic/natural hybrid polymers. A variety of naturally occurring polysaccharides like heparin, chitosan, dextran and alginate have frequently been used to form hydrogels (see, e.g., Kim et al. (2008) *Biotechnol. Adv*. (1): 1-21; Liang et al. (2011) *Coll. Surf B.* 82(1): 1-7; Davidenko et al. (2010) *Acta Biomater.* 6(10): 3957-3968; Stabenfeldt et al. (2006) *J. Biomed. Mater. Res. A.* 77(4): 718-725; Shikanov et al. (2009) *Biomaterials,* 30(29): 5476-5485; and the like). Polysaccharide hydrogels can be formed by covalent crosslinking, chemical conjugation, esterification and polymerization. In addition, polysaccharides have been combined with proteins such as collagen, gelatin, laminin and fibrin to form an interpenetrating network or composite hydrogels (see, e.g., Sakai et al. (2007) *J. Biosci. Bioeng.* 103(10): 22-26; Huang et al. (2005) *Biomaterials,* 26(36): 7616-7627; Dhandayuthapani et al. (2010) *J. Biomed. Mater. Res. B. Appl. Biomater.* 94(1): 264-272; Tan et al. (2009) *Acta Biomater.* 5(1): 328-337; Rosellini et al. (2009) *J. Biomed. Mater. Res. A.* 91(2): 447-453; Liu and Chan-Park (2009) *Biomaterials,* 30(2): 196-207; Hoffman (2002) *Adv. Drug Deliver. Rev.* 43(1): 3-12; Lin and Metters (2006) *Adv. Drug Deliver. Rev.* 58(12-13): 1379-1408; Schneider et al. (2004) *Biomaterials,* 25(15): 3023-3028; and the like).

Protein-based hydrogels can be formed by thermal gelation and their mechanical properties can be enhanced using chemical crosslinkers such as glutaraldehyde. Hydrogels formed from synthetic polymers possess more reproducible physical and chemical properties compared to hydrogels formed from natural materials. While designing a scaffold mechanical stability of the gel can an important consideration. The strength of hydrogels can be increased by incorporating crosslinking agents, comonomers, and increasing the degree of crosslinking (see, e.g., Nguyen and West (2002) *Biomaterial,* 23: 4307-4314; Hoffman (2002) *Adv. Drug Deliver. Rev.* 43(1): 3-12; Lin and Metters (2006) *Adv. Drug Deliver. Rev.* 58(12-13): 1379-1408; and the like). In certain embodiments nonbiodegradable synthetic hydrogels can be prepared, inter alia, from the copolymerization of various vinylated monomers or macromers (see, e.g., Hejcl et al. (2010) *Cells Delvelop.* 19(10): 1535-1546; Woerly et al. (2001) *Biomaterials,* 22(10): 1095-1111; Takezawa et al. (1990) *Nat. Biotechnol.* 8(9): 854-856; Vihola et al. (2005) *Biomaterials,* 26(16): 3055-3064; Park (2002) *Biotechnol. Lett.* 24(14): 1131-1135; Buxton et al. (2007) *Tissue Eng.* 13(10): 2549-2560; Beamish et al. (2010) *J. Biomed. Mater. Res. A.* 92(2): 441-450; Yang et al. (2005) *Biomaterials*26 (30): 5991-5998; Ossipov et al. (2007) *J. Appl. Polym. Sci.* 106(1): 60-70; and the like), such as 2-hydroxyethyl methacrylate (HEMA), 2-hydroxypropyl methacrylate (HPMA), acrylamide (AAm), acrylic acid (AAc), N-isopropylacrylamide (NIPAm), and methoxyl poly (ethylene glycol) (PEG) monoacrylate (mPEGMA or PEGMA), with crosslinkers, such as N,N'-methylenebis(acrylamide) (MBA), ethylene glycol diacrylate (EGDA) and PEG diacrylate (PEGDA). Poly (N-isopropylacrylamide) (PNIPAm) has been investigated extensively as a thermo-sensitive polymer, that can form thermosensitive hydrogels from free radical copolymerizing of NIPAm with crosslinkers like MBA (see, e.g., Takezawa et al. (1990) *Nat. Biotechnol.* 8(9): 854-856; Vihola et al. (2005) *Biomaterials,* 26(16): 3055-3064). PEG-based hydrogels can be prepared, inter alia, by radiation crosslinking of PEG or free radical polymerization of PEG macromers. PVA is another synthetic hydrophilic polymer that has extensively utilized in hydrogels (see, e.g., Sawhney et al. (1993) *Macromolecules,* 26(4): 581-587; Gibas and Janik (2010) *Chemistry Chemical Technol.* 4: 297-304). PVA can also be modified with acryloyl chloride or glycidyl methacrylate to generate reactive acrylate groups through the pendant hydroxyl groups, followed by crosslinking polymerization to form hydrogels. In addition, PVA can blend with other water-soluble polymers to form hydrogels Hydrogels can be synthesized by different polymerization methods using both chemical and physical crosslinking routes. Both natural polymers such as proteins or synthetic polymers like PVA, PEGDMA, and the like, with a high affinity for water, can be crosslinked to form hydrogels. Different crosslinking methods can be implemented for the design of a particular hydrogel.

In certain embodiments, chemically crosslinked hydrogels are synthesized by chain growth polymerization, addition and condensation polymerization and gamma and electron beam polymerization. Chain-growth polymerization includes, inter alia, free radical polymerization, controlled free radical polymerization, anionic and cationic polymerization. It is typically done by three processes viz., initiation, propagation, and termination. After initiation, a free radical active site is generated which adds monomers in a chain link-like fashion. For example, poly (N-isopropyl acrylamide) hydrogel are typically synthesized by free radical polymerization while PVA based hydrogels are typically prepared by free radical copolymerization. In certain embodiments PVA can be cross-linked chemically with monomer (methacrylic acid) in aqueous media using ethylene glycol di-methacrylate (EGDMA) as a cross-linking agent and benzoyl peroxide as reaction initiator.

Addition and condensation polymerization typically involves stepwise addition of polyfunctional crosslinking agents with monomer functional groups. Water soluble monomers can be converted into hydrogels using crosslinking agents such as tetramethylethylenediamine (TEMED) Polymer chains may be crosslinked in the presence of water to form a hydrogel. Water occupies voids in the network, giving the hydrogel its characteristic surface properties. Polyurethanes, polyesters, and nylon polymers are among the most common polymers synthesized for hydrogel applications (Hennink and van Nostrum (2002) *Adv. Drug Deliveries Rev.* 54: 13-36).

In certain embodiments hydrogels can be formed using gamma and electron beam polymerization, processes that involve high energy electromagnetic irradiation as crosslinker. These high energy radiations can crosslink water-soluble monomer or polymer chain ends without the addition of a crosslinker. During irradiation, using a gamma or electron beam, aqueous solutions of monomers are polymerized to form a hydrogel. Gamma and electron beam polymerizations can also involve the initiation, propagation, and termination steps as in the free radical polymerization. In certain embodiments hydroxyl radicals are formed and initiate free radical polymerization among the vinyl monomers which propagate in a rapid chain addition fashion (Hennink and van Nostrum (2002) *Adv. Drug Deliveries Rev.* 54: 13-36). The hydrogel is finally formed once the network reaches the critical gelation point. This process has an advantage over other crosslinking methods since it can be performed at room temperature and in physiological pH without using toxic and hard to remove crosslinking agents such as potassium persulfate (Id.)

Physically crosslinked hydrogels are typically synthesized by ionic interaction, crystallization, stereocomplex formation, hydrophobized polysaccharides, protein interaction and hydrogen bond. In ionic interactions, hydrogels can be crosslinked under mild conditions, at room temperature and physiological pH. This process of cross-linking does not require presence of ionic groups in the polymer. Metallic ions can be used to yield a stronger hydrogel (Id.). For stereocomplex formation, a hydrogel can be formed, e.g., through crosslinking that is formed between lactic acid oligomers of opposite chirality (Id.). Hydrophobic interactions can cause the polymer to swell and uptake water thereby forming the hydrogel. Polysaccharides such as chitosan, dextran, pullulan and carboxymethyl curdlan are reported in literature for the preparation of physically cross-linked hydrogels by hydrophobic modification. Protein interaction hydrogels can be formed using block copolymers that contain repetition of silk-like and elastine-like blocks called ProLastins (Id.). These ProLastins are fluid solutions in water and can undergo a transformation from solution to gel under physiological conditions because of the crystallization of the silk-like domains.

Poly Acrylic Acid (PAA) and Poly Methacrylic Acid (PMA) form complexes with Poly Ethylene Glycol (PEG) from the hydrogen bonds between the oxygen of the PEG and carboxylic group of PMA (Hennink and van Nostrum (2002) *Adv. Drug Deliveries Rev.* 54: 13-36). This interaction allows for the complex to absorb liquids and swell at low pH which transforms the system into a gel. Crystallization processes involving freezing-thawing processes can also create a strong and highly elastic gel (Yokoyama et al. (1986) *Colloid Polym. Sci.,* 264: 595-601). PVA hydrogels can be formed by physically crosslinking through repeated freezing/thawing methods, or chemically crosslinked with glutaraldehyde or epichlorohydrin.

As noted above, in certain embodiments the hydrogels can be comprised of one or more naturally-occurring polymers (e.g., cellulose or hyaluronan-based hydrogels), while in other embodiments, the hydrogels can comprise one or more synthetic polymers (e.g. polyethylene glycol dimethacrylate, urethane dimethacrylate, etc.). Illustrative hydrogels include, but are not limited to polyethylene glycol hydrogels, polyethylene oxide hydrogels, polyphosphazene hydrogels, collagen hydrogels, polysaccharide hydrogels, hydroxyethyl methacrylate hydrogels, acrylic hydrogels, copolymers of polyoxyethylene/polyoxypropylene/polyoxyethylene hydrogels, alginate hydrogels, gelatin based hydrogels, chitosan based hydrogels, dextran-aldehyde conjugate hydrogels, hyaluronan/gelatin hydrogels, acrylamide/itaconic acid copolymer hydrogels, acrylic hydrogels, nano-metal hydroxide hydrogels, poly(N-vinyl pyrrolidone) hydrogels, poly(N-isopropylacrylamide) hydrogels, collagen-chondroitin sulfate hyaluronic acid hydrogels, polyacrylic acid hydrogels, polyvinyl alcohol hydrogels, and the like.

In certain embodiments the hydrogels comprise a polyethylene glycol dimethacrylate (PEGDM aka PEGDMA) hydrogel, or a urethane dimethacrylate (PEGUDM) hydrogel.

In the illustrative experiments described herein, a polyethylene glycol dimethacrylate (PEGDMA) hydrogel was utilized. However, it will be recognized that any of a number of other hydrogels can similarly be used.

Methods of preparing hydrogels are well known to those of skill and numerous hydrogels are commercially available. For example, methods of synthesizing PEGDMA and urethane-dimethacrylate (PEGUDM) hydrogels are described by Lin-Gibson et al. (2004) *Biomacromolecules,* 5(4): 1280-1287. Alternatively the PEGDMA hydrogels can be obtained from commercial sources.

Methods of cross-linking polymers (e.g., PDGDMAs) to form hydrogels are well known to those of skill in the art.

Calcium crosslinked alginate, photocrosslinked alginate, and collagen hydrogels can be prepared as described by e.g., Krebs et al. (2009) *J. Am. Chem. Soc.,* 131(26): 9204-9206). Gils, et al. (2010 *Am. J. Biomed. Sci.* 2(4), 373-383 describe modification of xanthum gum (XG) polysaccharide to produce drug delivery hydrogels. In particular, they prepared XG-g-poly [HEMA-co-AA] superporous hydrogel (SPH) through chemical cross-linking by graft copolymerization of 2-hydroxyethyl methacrylate (HEMA) and acrylic acid (AA) on to XG via redox initiator system of ammonium persulfate (APS) and N, N, N', N'-tetramethylethylenediamine (TMED), in the presence of N, N'-methylenebisacrylamide (MBA) crosslinking agent, sodium bicarbonate foaming agent, a triblock copolymer of polyoxyethylene/polyoxypropylene/polyoxyethylene as a foam stabilizer. Oxidized alginate and gelatin (e.g., periodate oxidized sodium alginate) hydrogels are described by Balakrishnan and Jayakrishnan (2005) *Biomaterials* 26(18): 3941-3951. A number of alginate, chitosan, hyaluronan, polyethylene oxide/polypropylene oxide hydrogels are described by Gutowska et al. (2001) *Anat Rec.* 263(4): 342-349. A dextran-aldehyde conjugate hydrogel can be formulated by mixing carboxymethylcellulose-hydrazide with dextran-aldehyde as described by Hudson et al. (2010) *Biomaterials* 31(6): 1444-1452).

In certain embodiments the hydrogel comprises a hyaluronan (or a functionalized/derivatized hyaluronan) and a gelatin (or a functionalized/derivatized gelatin). In various embodiments the hyaluronan and/or the gelatin are each thiol-modified, e.g., by using carbodiimide mediated hydrazide chemistry. In some embodiments, the gel-forming material is based on chemically-modified hyaluronic acid. In some embodiments, the gel-forming hyaluronic acid matrix is HYSTEM®, HYSTEM®-HP, or HYSTEM®-C. The HYSTEM® hydrogels are formed by crosslinking mixtures of these thiolated macromolecules using polyethylene glycol diacrylate (PEGDA) or other suitable cross-linkers. The rate of gelation and hydrogel stiffness can be controlled by varying the amount of cross-linker. In addition, CM-Tec (Newark, Del.) offers commercial hydrogels made from gelatin and polyaspartate (or polyglutamate).

In certain embodiments the hydrogels are formed using a porosity generator (porogen) to determine/control the porosity of the hydrogel. Illustrative porogens include, but are not limited to salt crystals (e.g., NaCl crystals), beads (e.g., polymethyl methacrylate beads, polyethylene glycol beads (see, e.g., Badiger et al. (1993) *Biomaterials,* 14(14): 1059-1063), acetone, sodium bicarbonate, sugars (see, e.g., Horak et al. (2004) *Biomaterials* 25: 5249), paraffin (see, e.g., Draghi et al. (2005) *J. Mater. Sci. Mater. Med.* 16: 1093), gelatin (see, e.g., Gong et al. (2007) *Acta Biomater.* 3: 531), and the like.

The foregoing hydrogels are illustrative and not limiting. Using the teachings provided herein, numerous other hydrogels can be used in the ATPS/hydrogel systems described herein.

Aqueous Two Phase System (ATPS)

As explained above, it was discovered that hydrogels can be used in conjunction with (e.g., support) an aqueous two-phase system (ATPS) to facilitate separation and/or concentration of one or more analytes. In some embodiments, the ATPS comprises a phase solution. The term "phase solution" generally refers to a first phase solution or a second phase solution of the ATPS. In some embodiments, the phase solution is in a mixed solution (e.g. with the first/second phase solution). In some embodiments, the phase solution is the first/second phase solution after it separates from the mixed solution of the ATPS. In some embodiments, the phase solution is the first/second phase solution after it separates from the mixed solution in the hydrogel and/or LFA or flow-through assay. In certain embodiments the phase solution can refer to the second phase solution while it is in a mixed state (e.g. with the first phase solution). In some embodiments, the phase solution is a leading fluid in a hydrogel and/or an LFA or flow-through assay. In some embodiments, the phase solution is a lagging fluid in a hydrogel and/or LFA or flow-through assay.

In some embodiments, the ATPS comprises two aqueous solutions, a first phase solution and a second phase solution that are initially mixed (e.g., a mixed phase solution). In some embodiments, the mixed phase solution is a homogeneous solution, while in certain other embodiments the first phase solution and the second phase solution are immiscible. In some embodiments, the first phase solution and the second phase solution are immiscible, but domains of the first phase solution are mixed with domains of the second phase solution. In some embodiments, the immiscibility is driven by changes in temperature, and/or changes in the concentrations of the different components, such as salt. In some embodiments, the first/second phase solutions comprise components, such as, micelles, salts, and/or polymers. In some embodiments, the target analyte (e.g., biomolecule, bacterium (or fragment thereof), fungus (or fragment thereof), or virus (or fragment thereof), biomolecule such as a sugar, protein lectin, nucleic acid, etc., and the like) in contact with the ATPS, distributes, partitions, and/or concentrates preferentially into the first phase solution over the second phase solution, or vice versa, based on its physical and chemical properties, such as size, shape, hydrophobicity, and charge. In some embodiments, the target analyte partitions predominantly (or extremely) into the first or second phase solution of the ATPS, and therefore concentrates in the ATPS. In some embodiments, the target analyte is concentrated by adjusting the ratio of volumes between the first phase solution and the second phase solution. In some embodiments, the target analyte is concentrated by reducing the volume of the phase in which the analyte partitions. By way of illustration, in some embodiments, the target analyte is concentrated by 10-fold in the first phase solution, e.g., by using a 1:9 volume ratio of first phase solution to second phase solution, since the volume of the phase into which the analyte extremely partitions into is 1/10 the total volume.

In some embodiments, other concentrations are obtained by using other ratios. Thus, in some embodiments the ratio of the first phase solution to the second phase solution comprises a ratio of about 1:1, about 1:2, about 1:3, about 1:4, about 1:5, about 1:6, about 1:7, about 1:8, about 1:9, or about 1:10. In some embodiments the ratio of the first phase solution to the second phase solution comprises a ratio of about 1:20, about 1:30, about 1:40, about 1:50, about 1:60, about 1:70, about 1:80, about 1:90, or about 1:100. In some embodiments the ratio of the first phase solution to the second phase solution comprises a ratio of about 1:200, about 1:300, about 1:400, about 1:500, about 1:600, about 1:700, about 1:800, about 1:900, or about 1:1000.

In some embodiments the ratio of the second phase solution to the first phase solution comprises a ratio of about 1:1, about 1:2, about 1:3, about 1:4, about 1:5, about 1:6, about 1:7, about 1:8, about 1:9, or about 1:10. In some embodiments the ratio of the second phase solution to the first phase solution comprises a ratio of about 1:20, about 1:30, about 1:40, about 1:50, about 1:60, about 1:70, about 1:80, about 1:90, or about 1:100. In some embodiments the ratio of the second phase solution to the first phase solution comprises a ratio of about 1:200, about 1:300, about 1:400, about 1:500, about 1:600, about 1:700, about 1:800, about 1:900, or about 1:1000.

In some embodiments, the analyte partitions substantially evenly between the first phase solution and second phase solution, preventing concentration of the analyte. In such systems, concentration of the target analyte are achieved by introducing an additional component, such as a probe that captures the target analyte, and wherein the probe partitions predominantly into one phase, thereby enhancing the partitioning behavior of the target analyte to enable concentration. In some embodiments, the first/second phase solution containing the concentrated analyte is collected and applied to the LFA or to the flow-through assay device.

In some embodiments, the first/second phase solution comprises a micellar solution. In some embodiments, the micellar solution comprises a nonionic surfactant. In some embodiments, the micellar solution comprises a detergent. In some embodiments, the micellar solution comprises Triton-X. In some embodiments, the micellar solution comprises a surfactant similar to Triton-X, such as Igepal CA-630 and Nonidet P-40, and the like, by way of non-limiting example. In some embodiments, the micellar solution consists essentially of Triton-X.

In some embodiments, the micellar solution has a viscosity (at room temperature (~25° C.)) of about 0.01 centipoise to about 5000 centipoise, about 0.01 centipoise to about 4500 centipoise, about 0.01 centipoise to about 4000 centipoise, about 0.01 centipoise to about 3500 centipoise, about 0.01 centipoise to about 3000 centipoise, about 0.01 centipoise to about 2500 centipoise, about 0.01 centipoise to about 2000 centipoise, about 0.01 centipoise to about 1500 centipoise, about 0.01 centipoise to about 1000 centipoise, or about 0.01 centipoise to about 500 centipoise. In some embodiments, the micellar solution has a viscosity at room temperature of about 0.01 centipoise to about 450 centipoise, about 0.01 centipoise to about 400 centipoise, about 0.01 centipoise to about 350 centipoise, about 0.01 centipoise to about 300 centipoise, about 0.01 centipoise to about 250 centipoise, about 0.01 centipoise to about 200 centipoise, about 0.01 centipoise to about 150 centipoise, or about 0.01 centipoise to about 100 centipoise.

In some embodiments, the first/second phase solution comprises a polymer (e.g., polymer solution). In certain embodiments, the polymer is polyethylene glycol (PEG). In various embodiments, the PEG may have a molecular weight between 1000 and 100,000. In certain embodiments, the PEG comprises PEG-4600, PEG-8000, or PEG-20,000. In certain embodiments, the polymer is polypropylene glycol (PPG). In various embodiments, the PPG may have a molecular weight between 100 and 10,000. In certain embodiments, the PPG comprises PPG 425. In certain embodiments, the polymer is dextran. In various embodiments, the dextran may have a molecular weight between 1000 and 1,000,000. In certain embodiments, the dextran comprises dextran 6000, dextran 9000, dextran 15,000, dextran-35,000, or dextran-200,000.

In some embodiments, the polymer solution comprises a polymer solution that is about 0.01% w/w polymer, or about 0.05% w/w polymer, or about 0.1% w/w polymer, or about 0.15% w/w polymer, or about 0.2% w/w polymer, or about 0.25% w/w polymer, or about 0.3% w/w polymer, or about 0.35% w/w polymer, or about 0.4% w/w polymer, or about 0.45% w/w polymer, or about 0.5% w/w polymer, or about 0.55% w/w polymer, or about 0.6% w/w polymer, or about 0.65% w/w polymer, or about 0.7% w/w polymer, or about 0.75% w/w polymer, or about 0.8% w/w polymer, or about 0.85% w/w polymer, or about 0.9% w/w polymer, or about 0.95% w/w polymer, or about 1% w/w polymer. In some embodiments, the polymer solution comprises a polymer solution that is about 1% w/w polymer, or about 2% w/w polymer, or about 3% w/w polymer, or about 4% w/w polymer, or about 5% w/w polymer, or about 6% w/w polymer, or about 7% w/w polymer, or about 8% w/w polymer, or about 9% w/w polymer, or about 10% w/w polymer, or about 11% w/w polymer, or about 12% w/w polymer, or about 13% w/w polymer, or about 14% w/w polymer, or about 15% w/w polymer, or about 16% w/w polymer, or about 17% w/w polymer, or about 18% w/w polymer, or about 19% w/w polymer, or about 20% w/w polymer, or about 21% w/w polymer, or about 22% w/w polymer, or about 23% w/w polymer, or about 24% w/w polymer, or about 25% w/w polymer, or about 26% w/w polymer, or about 27% w/w polymer, or about 28% w/w polymer, or about 29% w/w polymer, or about 30% w/w polymer, or about 31% w/w polymer, or about 32% w/w polymer, or about 33% w/w polymer, or about 34% w/w polymer, or about 35% w/w polymer, or about 36% w/w polymer, or about 37% w/w polymer, or about 38% w/w polymer, or about 39% w/w polymer, or about 40% w/w polymer, or about 41% w/w polymer, or about 42% w/w polymer, or about 43% w/w polymer, or about 44% w/w polymer, or about 45% w/w polymer, or about 46% w/w polymer, or about 47% w/w polymer, or about 48% w/w polymer, or about 49% w/w polymer, or and about 50% w/w polymer. In some embodiments, the polymer solution comprises a polymer solution that is about 10% w/w polymer, or about 20% w/w polymer, or about 30% w/w polymer, or about 40% w/w polymer, or about 50% w/w polymer, or about 60% w/w polymer, or about 70% w/w polymer, or about 80% w/w polymer, or about 90% w/w polymer. In some embodiments, the polymer solution comprises a polymer solution that is about 10% w/w polymer to about 80% w/w polymer. In some embodiments, the polymer solution comprises a polymer solution that is about 10% w/w to about 25% w/w polymer.

In some embodiments, the first and/or second phase solution comprises a salt and thereby forms a salt solution. In some embodiments, the target analyte (e.g., bacterium, fungus, virus, etc.) and/or a probe-analyte complex partitions into the salt solution. In certain embodiments the salt solution comprises a kosmotropic salt. In some embodiments the salt solution comprises a chaotropic salt. In some embodiments, the salt comprises one or more of a magnesium salt, a lithium salt, a sodium salt, a potassium salt, a cesium salt, a zinc salt, and an aluminum salt. In some embodiments, the salt comprises a bromide salt, an iodide salt, a fluoride salt, a carbonate salt, a sulfate salt, a citrate salt, a carboxylate salt, a borate salt, or a phosphate salt. In some embodiments, the salt is potassium phosphate. In some embodiments, the salt is ammonium sulfate.

In some embodiments, the salt solution comprises a salt solution comprising about 0.01% w/w salt, or about 0.05% w/w salt, about 0.1% w/w salt, or about 0.15% w/w salt, or about 0.2% w/w salt, or about 0.25% w/w salt, or about 0.3% w/w salt, or about 0.35% w/w salt, or about 0.4% w/w salt, or about 0.45% w/w salt, or about 0.5% w/w salt, or about 0.55% w/w salt, or about 0.6% w/w salt, or about 0.65% w/w salt, or about 0.7% w/w salt, or about 0.75% w/w salt, or about 0.8% w/w salt, or about 0.85% w/w salt, or about 0.9% w/w salt, or about 0.95% w/w salt, or about or about 1% w/w salt. In some embodiments, the salt solution comprises a salt solution that is about 1% w/w salt, or about 2% w/w salt, or about 3% w/w salt, or about 4% w/w salt, or about 5% w/w salt, or about 6% w/w salt, or about 7% w/w salt, or about 8% w/w salt, or about 9% w/w salt, or about 10% w/w salt, or about 11% w/w salt, or about 12% w/w salt, or about 13% w/w salt, or about 14% w/w salt, or about 15% w/w salt, or about 16% w/w salt, or about 17% w/w salt, or about 18% w/w salt, or about 19% w/w salt, or about 20% w/w salt, or about 21% w/w salt, or about 22% w/w salt, or about 23% w/w salt, or about 24% w/w salt, or about 25% w/w salt, or about 26% w/w salt, or about 27% w/w salt, or about 28% w/w salt, or about 29% w/w salt, or about 30% w/w salt, or about 31% w/w salt, or about 32% w/w salt, or about 33% w/w salt, or about 34% w/w salt, or about 35% w/w salt, or about 36% w/w salt, or about 37% w/w salt, or about 38% w/w salt, or about 39% w/w salt, or about 40% w/w salt, or about 41% w/w salt, or about 42% w/w salt, or about 43% w/w salt, or about 44% w/w salt, or about 45% w/w salt, or about 46% w/w salt, or about 47% w/w salt, or about 48% w/w salt, or about 49% w/w salt, or and about 50% w/w. In some embodiments, the salt solution comprises a salt solution that is about 0.1% w/w to about 10%. In some embodiments, the salt solution is about 1% w/w to about 10%.

In some embodiments, the first/second phase solution comprises a solvent that is immiscible with water. In some embodiments, the solvent comprises a non-polar organic solvent. In some embodiments, the solvent comprises an oil. In some embodiments, the solvent comprises pentane, cyclopentane, benzene, 1,4-dioxane, diethyl ether, dichloromethane, chloroform, toluene, or hexane.

In some embodiments, the first phase solution comprises a micellar solution and the second phase solution comprises a polymer. In some embodiments, the second phase solution comprises a micellar solution and the first phase solution comprises a polymer. In some embodiments, the first phase solution comprises a micellar solution and the second phase solution comprises a salt. In some embodiments, the second phase solution comprises a micellar solution and the first phase solution comprises a salt. In some embodiments, the micellar solution is a Triton-X solution. In some embodiments, the first phase solution comprises a first polymer and the second phase solution comprises a second polymer. In some embodiments, the first/second polymer comprises polyethylene glycol and/or dextran. In some embodiments, the first phase solution comprises a polymer and the second phase solution comprises a salt. In some embodiments, the second phase solution comprises a polymer and the first phase solution comprises a salt. In some embodiments, the first phase solution comprises polyethylene glycol and the second phase solution comprises potassium phosphate. In some embodiments, the second phase solution comprises polyethylene glycol and the first phase solution comprises potassium phosphate. In some embodiments, the first phase solution comprises a salt and the second phase solution comprises a salt. In some embodiments, the first phase solution comprises a kosmotropic salt and the second phase solution comprises a chaotropic salt. In some embodiments, the second phase solution comprises a kosmotropic salt and the first phase solution comprises a chaotropic salt.

In some embodiments, the first phase solution comprises a Component 1 of Table 1 and the second phase solution comprises a Component 2 of Table 1. In some embodiments, the second phase solution comprises a Component 1 of Table 1 and the second phase solution comprises a Component 2 of Table 1.

In some embodiments, the components of Table 1 are suspended or dissolved in a buffer. In some embodiments, the components of Table 1 are suspended/dissolved in a buffer compatible with a biological system from which the sample was derived. In some embodiments, the components of Table 1 are suspended/dissolved in a saline solution. In some embodiments, the components of Table 1 are suspended/dissolved in PBS. In some embodiments, the components of Table 1 are suspended/dissolved in water. In some embodiments, the components of Table 1 are suspended/dissolved in the biological fluid.

TABLE 1

Illustrative aqueous two-phase extraction/concentration systems.

| Component 1 | Component 2 |
|---|---|
| **Polymer/polymer Systems** | |
| Polyethylene glycol | Dextran |
| | Ficoll |
| | Polyvinyl pyrrolidone |
| | Polyvinyl alcohol |
| | Hydroxypropyl starch |
| Polypropylene glycol | Dextran |
| | Hydroxypropyl dextran |
| | Polyvinyl pyrrolidone |
| Polyvinyl alcohol | Dextran |
| | Hydroxypropyl dextran |
| Polyvinyl pyrrolidone | Dextran |
| | Maltodextrin |
| Methyl cellulose | Dextran |
| | Hydroxypropyl dextran |
| Ethylhydroxyethyl cellulose | Dextran |
| **Polymer/salt Systems** | |
| Polyethylene glycol | Potassium phosphate |
| | Sodium sulfate |
| | Magnesium sulfate |
| | Ammonium sulfate |
| | Sodium citrate |
| Propylene glycol (PPG) | Potassium phosphate |
| Methoxypolyethylene glycol | Potassium phosphate |
| Polyvinyl pyrrolidone | Potassium phosphate |

Detection of Target Analytes (e.g., Biomolecules)

Figure 1B:
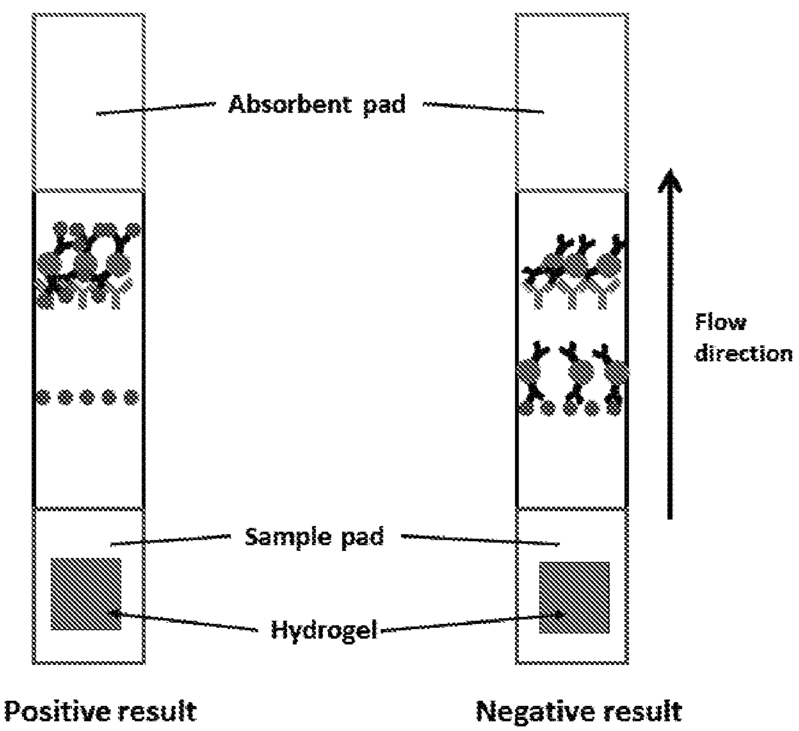
FIG. 1B illustrates the competitive format of a lateral-flow immunoassay integrating a hydrogel.
Figure 1C:
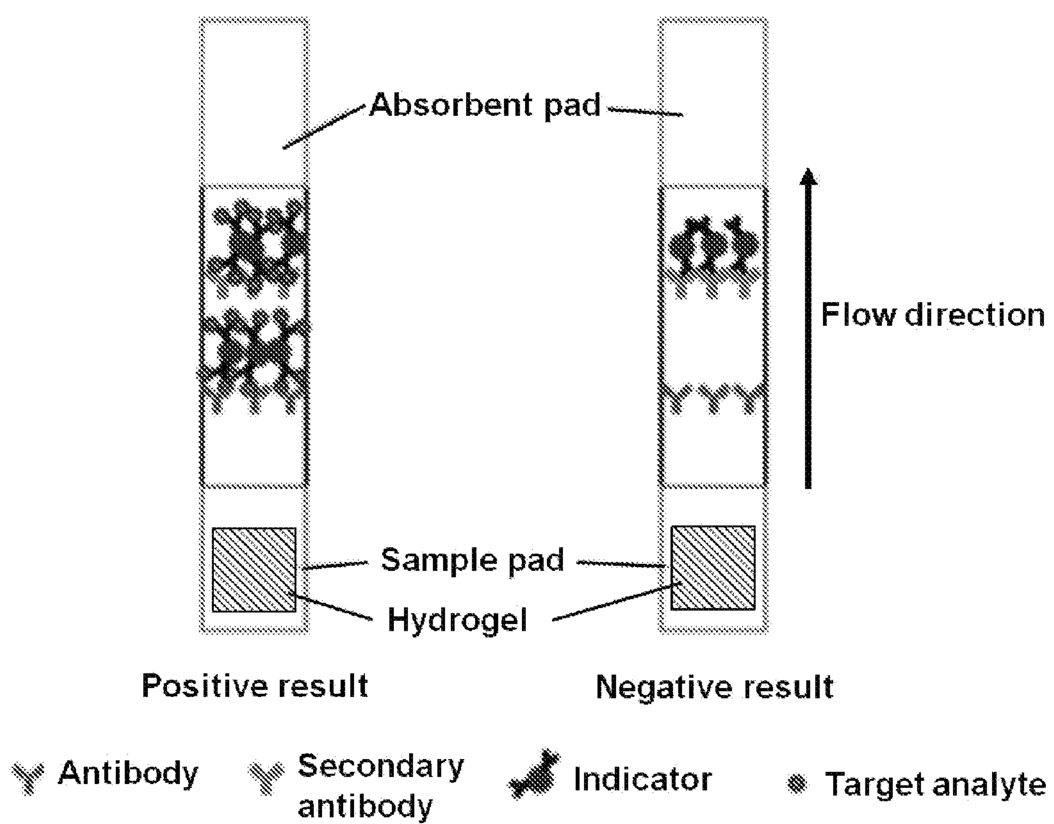
FIG. 1C illustrates a sandwich format of a lateral-flow immunoassay integrating a hydrogel.
Figure 2:
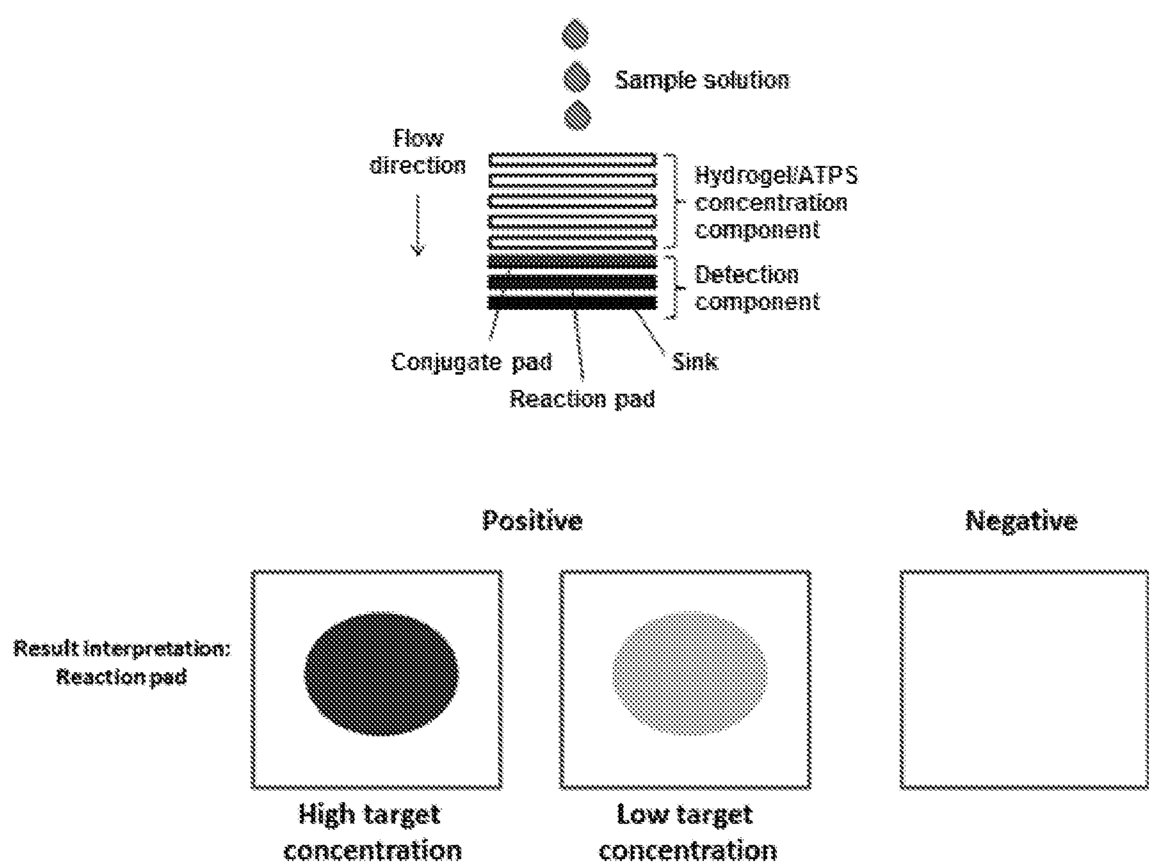
FIG. 2 shows a schematic of one embodiment of an all-in-one spot test for the detection of target analytes (e.g., biomolecules). In certain embodiments, the hydrogel (e.g., hydrogel or hydrogel containing ATPS) can be disposed on top of the spot test and thereby form a concentration component of the spot test. The user can simply apply the sample solution (or an ATPS containing the sample solution) to the device. The analytes will bind to the colorimetric indicator on the conjugate pad, and the resulting indicator-target complexes will be captured on the reaction pad as shown by a visible spot.

In various embodiments the hydrogel or hydrogel/ATPS systems described herein can be incorporated into assay devices comprising a lateral-flow assay (LFA) (see, e.g., FIGS. 1A-1C) or a flow-through (spot) assay (see, e.g. FIG. 2). In various embodiments both form factors may contain one or more of the following components:

Sample Pad

In certain embodiments a sample pad, when present, can connect the concentration component (e.g., a hydrogel or a hydrogel/ATPS system) to the detection component. It can act as a filter that can remove debris, contaminants, and mucus from the collected fluid. It can also store dried reagents, and when rehydrated, these reagents can (i) adjust the solution for optimal detection conditions (pH, ionic strength, etc.); and (ii) break down mucus, glycoproteins, and other viscous materials in the collected specimen that may affect detection. Illustrative materials for the sample pad include, but are not limited to, cellulose, nitrocellulose, fiberglass, cotton, woven or nonwoven paper, etc. Reagents on the pad may include, but are not limited to, surfactants such as Triton X-100, Tween 20, or sodium dodecyl sulfate, etc.; polymers such as polyethylene glycol, poloxamer, polyvinylpyrrolidone (PVP), etc.; buffers such as phosphate-buffered saline, 4-(2-hydroxyethyl)-1-piperazineethanesulfonic acid (HEPES), Tris(hydroxymethyl)aminomethane (Tris), sodium borate, TRICINE, etc.; proteins such as albumin, etc.; enzymes such as protease, etc.; salts such as sodium chloride, sodium phosphate, sodium cholate, potassium phosphate, etc. In various embodiments these reagents can be applied to the sample pad by (i) soaking the paper material in the reagent solution, or (ii) through wicking the membrane via capillary flow. The treated sample pad can be dried by (i) air drying (let sit in room temperature); (ii) baking (place in high temperature using an oven or heating device); (iii) vacuum; (iv) desiccation; or (iv) lyophilization.

In certain embodiments the sample pad can be upstream of the hydrogel or hydrogel/ATPS concentration component.

Conjugate Pad

In various embodiments a conjugate pad, when present can contain dehydrated colorimetric indicators decorated with binding moieties that bind the target analyte(s). In certain embodiments the binding moieties are specific binding moieties that have high affinity towards the target analyte(s) (e.g., bacterium, fungus, virus, proteins, DNA, etc.). When the sample solution reaches the conjugate pad, the colorimetric indicators are rehydrated. The binding moieties on the colorimetric indicators can then bind to the target analyte(s) and the resulting complexes can flow to the reaction pad. In certain embodiments the colorimetric indicators can comprise metallic particles such as gold, silver particles, polymeric particles such as latex beads, and polystyrene particles encapsulating visible or fluorescent dyes. Illustrative materials for the conjugate pad include, but are not limited to, cellulose, nitrocellulose, fiberglass, cotton, woven or nonwoven paper etc. In certain embodiments the colorimetric indicators can be applied and dehydrated onto the pad as described above.

Reaction Pad

In certain embodiments the reaction pad, when present, can comprise immobilized reagents, and when the immobilized reagents react with the sample solution, they may produce signals (e.g., visual signals) to indicate the presence or absence or quantity of the target analyte(s). Illustrative materials for the reaction pad include, but are not limited to cellulose, nitrocellulose, fiberglass, cotton, woven or nonwoven paper etc.

Lateral-Flow Format

In certain embodiments for a lateral-flow test strip, the reagents on the reaction pad will be immobilized in the form of lines perpendicular to the direction of flow to ensure all samples can interact with the immobilized reagents. The concentrations of the reagents can be optimized to control the signal intensities, and thus, control the sensitivity of the assay. For example, a semi-quantitative assay can be designed by immobilizing multiple lines of the same reagent with various concentrations. Each line therefore will yield signals only when a specific concentration of target biomolecules is reached. The concentration of the target biomolecules can then be interpreted by counting the number of lines that are visible.

In certain embodiments the hydrogel or hydrogel/ATPS system can be disposed on a sample pad comprising the LFA or directly on the lateral flow strip itself. Typically the hydrogel will be in fluid communication with the sample pad and/or porous strip to permit the ATPS containing analyte to pass into the LFA (see, e.g., FIG. 1).

In addition, multiple lines of different reagents can be immobilized on the same strip to detect multiple target analyte(s). This allows the development of multiplex assays.

Flow-Through Format

In certain embodiments for the flow-through test, instead of lines, the reagents can be immobilized on the entire reaction pad. If the target analyte is present, it will bind to the colorimetric indicator on the conjugate pad and be trapped on the reaction pad as the indicator-target complex binds to the immobilized reagent. A visible spot would therefore appear if the target biomolecule is present. This test can be used if the sample volume is too low to wick up a lateral-flow test strip. The color intensity of the visible spot is correlated to the concentration of target biomolecules, while the size of the spot is correlated to the sample volume. In certain embodiments the concentration component can be placed directly on top of the flow-through test to remove the need for extracting and applying the concentrated samples to the detection component.

In certain embodiments the hydrogel or hydrogel/ATPS system can be disposed on top of the flow-through (spot) assay. In certain embodiments the hydrogel or hydrogel/ATPS system is disposed on a sample pad on top of the flow-through assay or on the flow-through assay media itself. Typically the hydrogel will be in fluid communication with the sample pad and/or flow-through media to permit the ATPS containing analyte to pass into the flow-through assay (see, e.g., FIG. 2).

In various embodiments the immobilized reagents can comprise a specific antibody against the target analyte (primary antibody), antibodies against the primary antibody (secondary antibody), antigens, proteins, or antigen-protein conjugates. Illustrative materials for the reaction pad include, but are not limited to cellulose, nitrocellulose, fiberglass, cotton, woven and nonwoven paper etc. In various embodiments the reagents can be applied and dehydrated onto the pad as described above.

Sink

In certain embodiments the sink, when present, can comprise an absorbent pad that collects excess fluid and prevents back-flow, which can affect the test performance. Illustrative materials for the sink include, but are not limited to cellulose, nitrocellulose, fiberglass, cotton, woven and nonwoven paper etc.

Signal Enhancement

As described above, in various embodiments the visible signal intensity can be enhanced to improve the sensitivity and/or accuracy of the detection assay. In certain embodiments this can be performed by introducing additional development (signal enhancement) reagents to the reaction pad after the initial detection assay (analyte binding).

In certain embodiments the probes and ATPS can be designed to first deliver the probes to a detection zone (e.g., in a leading phase or interface of an ATPS) followed by later delivery of a development reagent (e.g., in a lagging phase of an ATPS).

In certain embodiments the signal enhancement reagent can comprise a substrate that reacts with an enzyme that is decorated on the surface of, e.g., colorimetric indicator to form a strong visible product. By way of example, if the colorimetric indicator comprises a gold probe, the signal enhancement can be achieved by silver-enhancement labeling, where an enhancement reagent containing silver ion can be applied to the reaction pad where the gold probe is bound to the immobilized line/spot. In this scenario, the gold probes can act as nucleation sites so that silver can be deposited onto the particle, resulting in increased signal intensity. In these examples, the signal enhancement reagents can either be added separately after the initial detection assay, or stored/dehydrated on the paper device to be released automatically/manually.

In other illustrative, but non-limiting embodiments, the development reagent can be a substrate for an enzyme (e.g., of alkaline phosphatase, horse radish (or other) peroxidase, glucose oxidase, etc.) that reacts with the corresponding enzyme associated with or attached to the probe(s) to produce an enhanced detectable signal. Alternatively the developing reagent can comprise the enzyme while the substrate is attached to or associated with the probe(s).

The foregoing components and assay formats are illustrative and non-limiting. Using the teachings and examples, provided herein, numerous other assay devices and configurations will be available to one of skill in the art and some further design considerations and components are described below.

Lateral-Flow Assay (LFA) or Flow-Through (Spot) Assay

As explained above, in certain embodiments, the devices and systems described herein are configured to provide a lateral-flow assay (LFA) or a flow-through (spot) assay for detection of the target analyte in a sample, where the LFA or spot assay is typically used in conjunction with a hydrogel or hydrogel/ATPS system to facilitate analyte separation and/or concentration. In certain embodiments the components of the ATPS can be provided in a dried form in the dry hydrogel (or into a porous matrix/paper comprising the LFA and/or spot assay). In certain embodiments the ATPS is added (separately or combined with sample) to the hydrogel. Typically the hydrogel and the porous matrix are configured to and have porosity sufficient to allow the ATPS or components thereof to flow through the hydrogel and matrix materials when the ATPS or components thereof are in a fluid phase. Such porous LFA or spot assay devices are referred to herein as paper or paper fluidic devices and these terms are used interchangeably.

The term "paper", as used herein, is not limited to thin sheets from the pulp of wood or other fibrous plant substances although, in certain embodiments the use of such papers in the devices described herein is contemplated. Papers more generally refer to porous materials often in sheet form, but not limited thereto that allow a fluid to flow through.

In some embodiments, the hydrogel and/or porous matrix is sufficiently porous to allow the mixed phase solution, first phase solution and/or second phase solution of the ATPS, and/or target analyte, to flow through the hydrogel or hydrogel/ATPS system and/or the LFA. In some embodiments, the hydrogel and/or porous matrix is sufficiently long and/or deep enough for the mixed phase solution, first phase solution and/or second phase solution, and/or target analyte, to flow vertically and/or horizontally through the hydrogel and/or LFA or spot assay device. In some embodiments, the first phase solution flows through the hydrogel and/or porous matrix at a first rate and the second phase solution flows through the hydrogel and/or porous matrix at a second rate, where the first rate and the second rate are different. In some embodiments of the hydrogel, the hydrogel is comprised of polyethylene glycol dimethacrylate, polyacrylic acid, polyvinyl alcohol, or hyalauronic acid, as well as others. In some embodiments, the porogens used to make pores in the hydrogel are comprised of NaCl, polymethyl methacrylate beads, or polyethylene glycol, as well as others. In some embodiments of the LFA or spot assay the porous matrix comprises inter alia a material such as a scintered glass ceramic, a mineral, cellulose, a fiberglass, a nitrocellulose, polyvinylidene fluoride, a nylon, a charge modified nylon, a polyethersulfone, combinations thereof, and the like.

Concentrate-as-it-Flows

It was discovered that ATPSs can phase separate as the solution flows through a hydrogel and through a porous substrate (e.g., a paper) which we have termed "concentrate-as-it-flows". Moreover it was also discovered that flow through the hydrogel and/or paper significantly speeds up the concentration process. Based on this phenomenon, the lateral-flow assay devices and the flow-through assay devices described herein can comprise a hydrogel optionally incorporated on or into a paper fluidic component that fully integrates the necessary components for a combined ATPS concentration with the LFA or flow-through detection. It was discovered that when a mixed ATPS solution is applied to a hydrogel and/or to certain paper materials, phase separation and analyte concentration occurs as the solution flows. It is believed this phenomenon is preserved even when making an ATPS that had varying volume ratios, e.g., volume of the top phase divided by that of the bottom phase.

In some embodiments, the LFA or the spot assay (e.g., the concentration component of the spot assay) comprises a paper. In some embodiments, the paper comprises a sheet of porous material that allows fluid to flow through it. In some embodiments, the paper comprises a plurality of sheets of porous material that allows fluid to flow through them. In some embodiments, the paper comprises one or more materials such as cellulose, fiberglass, nitrocellulose, polyvinylidine fluoride, charge modified nylon, polyether sulfone, and the like. In some embodiments, the paper is a HI-FLOW PLUS® membrane.

In some embodiments, the paper is a woven paper. In some embodiments, the paper is a Whatman paper. In some embodiments, the Whatman paper comprises Whatman S17, Whatman MF1, Whatman VF1, Whatman Fusion 5, Whatman GF/DVA, Whatman LF1, Whatman CF1, and/or Whatman CF4.

In some embodiments, the paper additionally concentrates (e.g., beyond the concentration afforded by the hydrogel) the target analyte as the target analyte flows through the LFA or through the concentration component of a flow-through assay (e.g. a ‘concentrate-as-it-flows’-based device). In some embodiments, the hydrogel and/or paper concentrates the target analyte as the target analyte flows through the LFA horizontally. In some embodiments, the hydrogel and/or paper concentrates the target analyte as the target analyte flows through the LFA or flow through assay vertically.

In some embodiments, the hydrogel or paper has a property that influences which phase solution will become the “leading fluid.” By way of non-limiting example, when using PEG-salt ATPS, adding the solution to fiberglass paper will cause the salt phase to become the leading solution, while using cellulose paper will cause the PEG phase to become the leading solution. Similarly, in certain embodiments, the hydrogel can be functionalized to cause a particular phase (e.g., salt phase, PEG phase, etc.) to become a leading or trailing solution.

In some embodiments, phase separation within the hydrogel and/or paper accelerates phase separation. Also by way of non-limiting example, a micellar ATPS typically takes several hours to phase separate in a stagnant ATPS, but if applied to a hydrogel and/or to a paper strip, this phase separation occurs far more rapidly. This speeds up the diagnostic process by allowing the ATPSs, which are traditionally the rate-determining step in the process, to become more viable options for our rapid paper diagnostic assays. In some embodiments, the ‘concentrate-as-it-flows’ device comprises a PEG-salt ATPS (e.g., as illustrated in the Examples). In some embodiments, the ‘concentrate-as-it-flows’ device comprises a micellar ATPS. In some embodiments, the LFA device or the flow-through assay device comprises fiberglass paper or nitrocellulose paper.

In certain embodiments the LFA or flow-through assay device comprises a filter that removes debris (e.g., blood cells or other particulates), a sample pad where the sample comprising the target analyte is applied to the device, a detection zone (e.g. test line and control line) where there the target analyte binds and is detected, and an absorbent pad (e.g., a dry receiving paper) that can absorb excess sample and/or solutions applied to the LFA or flow through device (see, e.g., FIGS. 1 and 2). In some embodiments, the control line and/or test line is not a line per se, but a region or spot.

In some embodiments, the LFA comprises an LFA strip. The terms “LFA” and “LFA strip” are used interchangeably herein. In some embodiments, the LFA strip has a length greater than its width and depth. In some embodiments, the LFA is rectangular. In some embodiments, the LFA has a shape that is round, ovoid, square, polygonal, or irregular-shaped. In some embodiments, the LFA comprises a plurality of routes and/or junctions. In some embodiments, the LFA strip comprises the sample pad, detection zone and absorbance pad. In some embodiments, the detection zone is located between the sample pad and the absorbent pad, the absorbent pad wicking the sample with the target analyte away from the sample pad and toward the detection zone.

Sandwich Assay

In some embodiments, detecting component, e.g., an LFA device, a flow-through (spot) assay device, etc., is configured to provide or run a sandwich assay (see e.g., FIG. 1, herein, and FIG. 1, bottom left, in copending PCT Application No: PCT/US2015/019297, filed on Mar. 6, 2015, which is hereby incorporated by reference for the LFA configurations described therein). In some embodiments, the sandwich assay comprises a capture moiety that binds the target analyte. In some embodiments, the device comprises a probe. In some embodiments, the probe comprises a detectable property (colorimetric, fluorescent, radioactive, etc.). In some embodiments, the probe comprises a binding moiety that interacts with the target analyte (e.g. an antibody). In some embodiments, the probe is added to the sample and binds the target analyte to form a probe-analyte complex.

In some embodiments, the probe-analyte complex is applied to the hydrogel, or to a sample pad on the hydrogel, and flows through the hydrogel and through the LFA or the flow-through device towards the absorbent pad. In some embodiments, the target analyte of the probe-analyte complex binds to the capture moiety. In some embodiments, the capture moiety is immobilized on a test line or a test region (e.g., a test layer in a flow-through device) and the probe-analyte complex becomes immobilized on the test line or in the test region. In some embodiments, the probe is colorimetric, and the test line or test region will exhibit a strong color (e.g. detectable signal) as the probe-analyte complex accumulates at the test line or in the test region, indicating a positive result. In some embodiments, there is no target analyte present in the sample, and the probe of the probe-analyte complex does not interact with the capture moiety, and the absence of the test line or signal in the test region indicates a negative result. In some embodiments, the LFA comprises a probe capture moiety on a control line (or in a control region, e.g., of a flow-through assay device) that interacts directly with the probe and/or the binding moiety, and thus, regardless of the presence of the target analyte in the sample, the probe/binding moiety binds to the probe capture moiety and accumulates on the control line or in the control region. In some embodiments, the probe capture moiety is a secondary antibody that binds the binding moiety, wherein the binding moiety is a primary antibody that binds that target analyte. In some embodiments, the probe becomes immobilized and detected on the control line or in the control region, indicating a valid test. In some embodiments, a positive result (e.g. target analyte is present in sample) is indicated by a detectable signal at the test line (or test region) and the control line (or control region). In some embodiments, a negative result is indicated by a detectable signal at the control line or in the control region.

Competition (Competitive) Assay

In some embodiments, the LFA comprises a competition or competitive assay. In some embodiments, the probe is added to the sample and binds the target analyte to form a probe-analyte complex. In some embodiments, the LFA comprises the target analyte immobilized on the test line. In some embodiments, the probe is saturated by the target analyte in the sample and the probe will not bind to the target analyte immobilized on the test line. In some embodiments, the absence the detectable signal on the test line indicates a positive result. In some embodiments, there is no target analyte present in the sample, and the probe binds to the target analyte on the test line, indicating a negative result. In some embodiments, the LFA comprises a probe capture moiety on a control line that interacts directly with the probe, and regardless of the presence of the target analyte in the sample, the probe can bind to the probe capture moiety and accumulate on the control line. In some embodiments, the probe becomes immobilized and detected on the control line, indicating a valid test. In some embodiments, a positive result (e.g., target analyte is present in sample) is indicated a detectable signal at the test line and the control line. In some embodiments, a negative result is indicated by a detectable signal at the control line.

Dehydrated ATPS in LFA or Flow-Through (Spot) Assay Device.

In some embodiments, the ATPS or components thereof and/or probes and/or development reagents are dehydrated on and/or in at least a first portion of a hydrogel (e.g., a dry hydrogel) and/or on and/or in at least a first portion of the porous matrix comprising an LFA or in a component of a flow-through assay device. In some embodiments, application of the sample to the device hydrates the hydrogel and/or ATPS, and/or probes and/or development reagent(s) thereby hydrating and expanding the hydrogel and converting the ATPS or components thereof and/or probes and/or development reagent(s) to a fluid phase. Dehydration may make the device more user friendly as the user just needs to add the sample (e.g., saliva, blood, urine, vaginal fluid, seminal fluid, sputum, cerebrospinal fluid, lymph, or similar fluid) to the device. In some embodiments, a user only has to apply a solution of the sample to the strip to detect the presence/absence of the target analyte or to quantify the analyte. In some embodiments, the solution of the sample flows through the LFA or the flow-through device and the ATPS is re-solubilized, triggering phase separation within the LFA or flow-through device and subsequent concentration of the target analyte.

In some embodiments, all the necessary components for a given ATPS are mixed to form a mixed solution, applied to the hydrogel and/or to the paper comprising the device (e.g., LFA or flow-through (spot) assay), and then dehydrated. When the sample solution is added to the dehydrated paper, the ATPS components are rehydrated as the sample flows, resulting in phase separation. In some ATPSs where the phase containing the concentrated analyte is less viscous, that phase will flow faster and the concentrated analyte will emerge in the leading fluid and will reach the detection zone of the LFA or flow-through assay to initiate detection. Additionally, the dehydrated ATPS component segment length (or thickness) and concentration can be adjusted for different applications.

Figure 16:
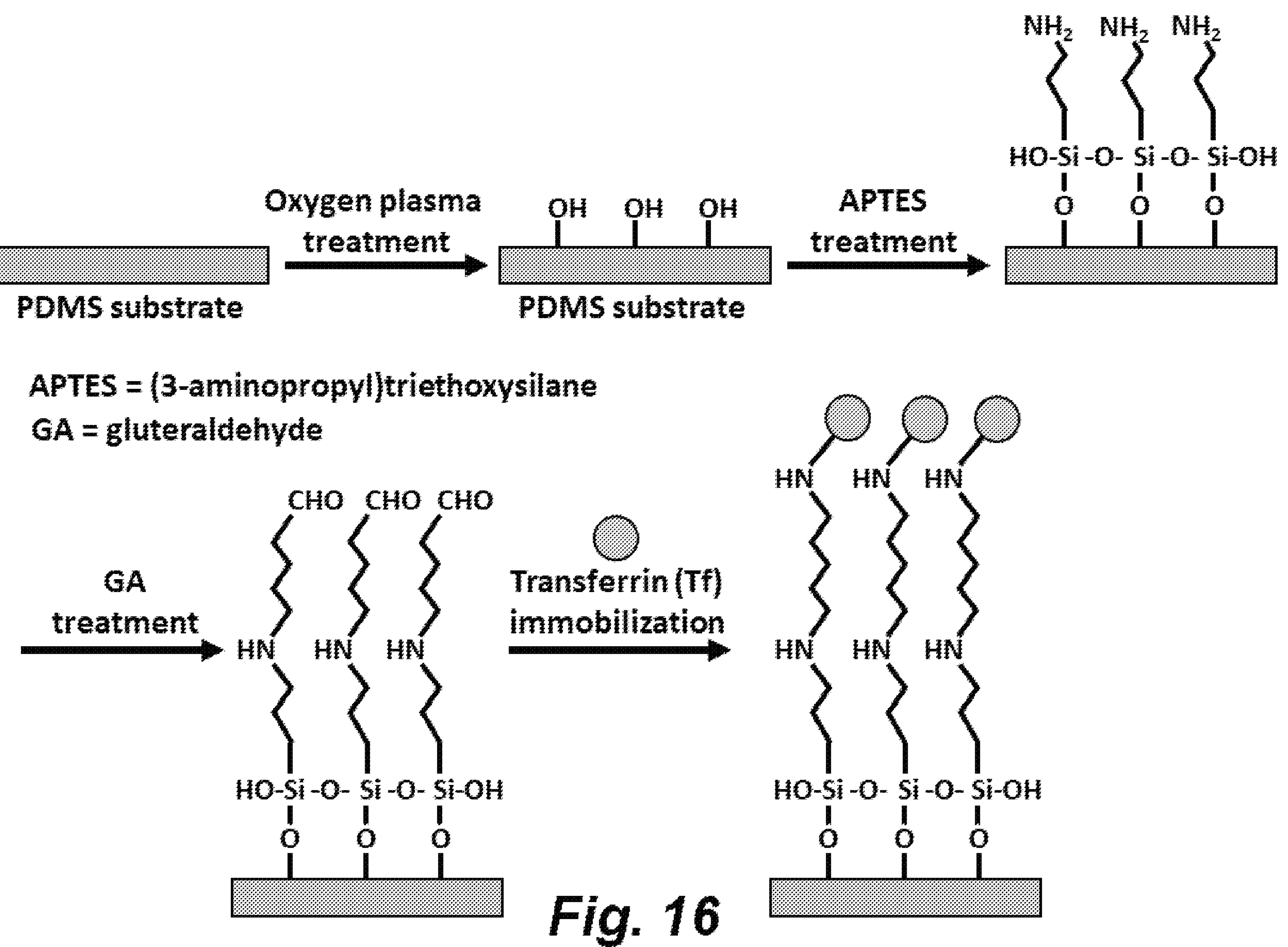
FIG. 16 illustrates a reaction scheme for (3-aminopropyl) triethoxysilane (APTES)—Glutaraldehyde (GA) conjugation.

In some embodiments, both (all) components of the ATPS are dehydrated on hydrogel and/or the LFA or in the flow-through assay (e.g., in the separation component). In some embodiments, a first ATPS component is dehydrated on (or in) the LFA or in the flow-through assay. In some embodiments, a second ATPS component is dehydrated on or in the hydrogel and/or the LFA or flow through assay. In some embodiments, the first phase solution component and/or first ATPS component is dehydrated on a first portion of the hydrogel and/or the LFA or in a first hydrogel layer and/or a first layer of the flow through assay (separation component). In some embodiments, the second phase solution component and/or second ATPS component is dehydrated on a second portion of the LFA or in a second layer of the flow-through assay (separation component). In some embodiments, the first portion and the second portion are same. In some embodiments, the first portion and the second portion are different. By way of non-limiting example, in a PEG-salt ATPS, the PEG and salt solutions can be dehydrated separately into different hydrogel portions and/or different paper portions or segments (see, e.g., FIG. 16 of copending PCT Application No: PCT/US2015/019297, filed on Mar. 6, 2015, which is hereby incorporated by reference for the LFA configurations described therein) or in separate layers comprising, e.g., the separation component of a flow-through assay. In some embodiments, dehydrating the first/second phase solution and/or ATPS component on different portions of the hydrogel and/or LFA or in different layers of the flow-through assay provides a more uniform concentration of the first/second phase solution components or ATPS components. In some embodiments, dehydrating the first/second phase solution components and/or ATPS components on different portions allows the first phase solution or ATPS component to flow in a first direction after hydration and the second phase solution and/or ATPS component to flow in a second direction after hydration, wherein the first and second directions are different. In some embodiments, the target analyte is concentrated in the first direction, but not the second direction. In some embodiments, the target analyte is concentrated in the second direction, but not the first direction. In some embodiments, dehydrating the first/second phase components and/or ATPS components on different portions allows the target analyte to flow in the first/second direction without requiring the sample to flow in the first/second direction. In some embodiments, dehydrating the first/second phase components and/or ATPS components on different portions allows the target analyte to flow faster, resulting in detection sooner. In some embodiments, dehydrating the first/second phase components and/or ATPS components on different portions allows for increased result reliability. In some embodiments, dehydrating the first/second phase components and/or ATPS components on different portions prevents aggregation of first/second phase solution components and/or ATPS components (e.g. PEG-salt ATPS). In some embodiments, the first/second phase component and/or ATPS component is dehydrated in multiple segments. In some embodiments the first/second phase component and/or ATPS component is dehydrated in multiple segments, wherein the first/second phase component and/or ATPS component comprises a salt solution. In some embodiments the first/second phase component and/or ATPS component is dehydrated in multiple segments, wherein the first/second phase component and/or ATPS component does not comprise a polymer (e.g. PEG). In some embodiments, dehydrated PEG is not located near the detection zone because the PEG-rich phase can slow the flow within the detection membrane. In some embodiments, the LFA strip or the flow-through assay can comprise a blank spacer near the detection zone that does not contain PEG or salt.

In some embodiments, a probe (e.g., an analyte binding moiety and associated detection reagent/material) is provided in a probe buffer. In some embodiments, the probe buffer is dehydrated in the hydrogel and/or on the LFA or in the flow-through assay.

In some embodiments, dehydration of ATPS components improves the limit of detection compared to a device in which the ATPS components are added in liquid form. In some embodiments, the addition of liquid form ATPS components dilutes the sample solution from the subject. In some embodiments, dehydration of ATPS components allows for a distinct first phase solution and/or distinct second phase solution to develop during flow, concentrating the target analyte or probe-analyte complex in a small volume at the front of the leading fluid that will reach the test and control lines or the detection component of a flow-through assay. In some embodiments, concentrating the target analyte and or probe-analyte complex at the front of the leading fluid will decrease the time period necessary for detection.

Probes

In certain embodiments the systems and/or devices described herein and/or the methods described herein utilize a probe, where the probe comprises a binding moiety that binds the target analyte to form a probe-analyte complex.

In some embodiments, the target analyte alone partitions preferentially into the first phase solution or second phase solution or interface of the first phase solution and second phase solution. In some embodiments, the target analyte alone partitions extremely into the first phase solution or second phase solution or interface of the first phase solution and second phase solution.

In some embodiments, the target analyte alone does not partition preferentially into the first phase solution or second phase solution or interface of the first phase solution and second phase solution. In some embodiments, the target analyte alone does not partition extremely into the first phase solution or second phase solution or interface of the first phase solution and second phase solution.

In some embodiments, the probe-analyte complex partitions preferentially into the first phase solution or second phase solution or interface of the first phase solution and second phase solution, thereby causing the target analyte (of the probe-analyte complex) to partition preferentially into the first phase solution or second phase solution or interface of the first phase solution and second phase solution.

In some embodiments, the probe-analyte complex partitions extremely into the first phase solution or second phase solution or interface of the first phase solution and second phase solution, thereby causing the target analyte (of the probe-analyte complex) to partition extremely into the first phase solution or second phase solution or interface of the first phase solution and second phase solution.

In some embodiments, the phrase "partitions preferentially," when used with respect to the partitioning of the target analyte (or probe-analyte complex) to a first/second phase solution of the ATPS, indicates that a greater amount of the target analyte becomes disposed in a preferred phase solution than in another phase solution of the ATPS.

In some embodiments, the phrase "partitions extremely," when used with respect to the partitioning of the target analyte (or probe-analyte complex) to a first/second phase solution of the ATPS, indicates that about 90% or more of the target analyte becomes disposed in a preferred phase solution than in another phase solution of the ATPS.

In some embodiments, a greater amount of the target analyte partitions into the first phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the first phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the first phase solution.

In some embodiments, a greater amount of the analyte partitions into the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the second phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the second phase solution.

In some embodiments, a greater amount of the analyte partitions into the interface of the first phase solution and the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the interface. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the interface.

In some embodiments, the device comprises or is configured to utilize and/or the assay run on the device utilizes one probe (probes directed to a single analyte). In some embodiments, the device comprises or is configured to utilize and/or the assay run on the device utilizes at least two different probes (each directed to a different analyte), or at least 3 different probes, or at least 4 different probes, or at least 5 different probes, or at least 7 different probes, or at least 10 different probes, or at least 15 different probes, or at least 20 different probes.

In some embodiments, the probe comprises one or more of a synthetic polymer, a metal, a mineral, a glass, a quartz, a ceramic, a biological polymer, a plastic, and/or combinations thereof. In some embodiments, the probe comprises a polymer comprises a polyethylene, polypropylene, nylon (DELRIN®), polytetrafluoroethylene (TEFLON®), dextran and polyvinyl chloride. In some embodiments, the polyethylene is polyethylene glycol. In some embodiments, the polypropylene is polypropylene glycol. In some embodiments, the probe comprises a biological polymer that comprises one or more of a collagen, cellulose, and/or chitin. In some embodiments, the probe comprises a metal (e.g., that comprises one or more of gold, silver, platinum titanium, stainless steel, aluminum, or alloys thereof). In some embodiments, the probe comprises a nanoparticle (e.g., a gold nanoparticle, a silver nanoparticle, etc.).

In some embodiments, the probe further comprises a coating. In some embodiments, the coating comprises polyethylene glycol or polypropylene glycol. In some embodiments, the coating comprises polypropylene. In some embodiments, the coating comprises polypropylene glycol. In some embodiments, the coating comprises dextran. In some embodiments, the coating comprises a hydrophilic protein. In some embodiments, the coating comprises serum albumin. In some embodiments, the coating has an affinity for the first phase solution or the second phase solution.

In some embodiments, the amount of target analyte in the sample is very low, such that the analyte needs to be substantially concentrated to enable detection by LFA or flow-through assay. In certain embodiments, substantial concentration is achieved at an interface, since the degree of analyte concentration is dependent on the volume of a phase in which the analyte partitions, or concentrates, and the "volume" at the interface is very small relative to the bulk phases.

In some embodiments, the probe partitions preferentially (or extremely) to the interface in order to drive the target analyte towards an interface. In some embodiments, the probe partitions preferentially (or extremely) to the interface due to their surface chemistry, wherein the surface chemistry is optimized to drive the probe to the interface. By way of non-limiting example, to drive the probe-analyte complex to the interface of a polymer-salt ATPS system, such as the polyethylene glycol-potassium phosphate (PEG/salt) system, the probes are conjugated to PEG (or PEGylated) to promote the PEG-PEG interaction with the PEG-rich phase, and/or are decorated with hydrophilic proteins to promote hydrophilic interactions with the PEG-poor phase. Using such an optimized probe decorated with specific antibodies or other molecules capable of binding to the target, the target analyte is captured and collected at the interface. Since the volume of the interface is very small, the analytes are highly concentrated and are applied to the subsequent LFA or detection region of the flow-through assay.

In some embodiments, gold nanoprobes (GNP) are prepared that are capable of partitioning to the interface of a PEG/salt ATPS, and operating conditions are optimized to allow for a fast phase separation time with a very high recovery of GNP/analyte.

In some embodiments, the probe-analyte complex partitions to a solid-liquid interface in the ATPS. In some embodiments, the solid is the wall of the chamber that contains the ATPS. In some embodiments, the solid is the collector of the assay device. In some embodiments, the solid comprises a solid polymer. In some embodiments, the solid polymer comprises polyethylene, cellulose, chitin, nylon, polyoxymethylene (DELRIN®), polytetrafluoroethylene (TEFLON®), polyvinyl chloride, or combinations thereof. In some embodiments, the solid polymer comprises polypropylene. In some embodiments, the probe-analyte complex sticks to the solid and is highly concentrated since it is present in the small volume at the solid-liquid interface, and not diluted by the volume of the bulk phases. In some embodiments, the bulk phase is removed without disrupting the concentrated analyte, and is collected by washing, with subsequent application to the LFA or to the flow-through assay device. In some embodiments, this approach significantly concentrates the analyte and allows collection without use of an external force (e.g., magnet). Alternatively, the probe comprises a magnetic material and this approach is used with a magnet. In some embodiments, these probes are modified to be concentrated at the interface for extreme analyte concentration. As mentioned above, this approach can provide additional separation of the target analyte from other contaminants, which is nonspecifically concentrated by ATPS, through the use of a magnet. In some embodiments, the ATPS concentration enables the magnetic probe to work more efficiently, since the magnetic probe would first be concentrated into a very small volume at a specific location (the interface). Accordingly, a smaller magnet or a weaker magnetic field will be required to collect the concentrated analyte. In some embodiments, the combination of ATPS interface concentration with magnetic probes allows for the development of a more effective, rapid, and cheaper device compared to the current state-of-the-art.

Binding Moiety

In some embodiments, the binding moiety is a molecule that binds the target analyte (e.g., bacterium, fungus, virus, lectin, sugar, protein, DNA, etc.). In some embodiments, the binding moiety is a molecule that specifically binds the target analyte. In some embodiments, "specifically binds" indicates that the molecule binds preferentially to the target analyte or binds with greater affinity to the target analyte than to other molecules. By way of non-limiting example, an antibody will selectively bind to an antigen against which it was raised. Also, by way of non-limiting example, a DNA molecule will bind to a substantially complementary sequence and not to unrelated sequences under stringent conditions. In some embodiments, "specific binding" can refer to a binding reaction that is determinative of the presence of a target analyte in a heterogeneous population of molecules (e.g., proteins and other biologics). In some embodiments, the binding moiety binds to its particular target analyte and does not bind in a significant amount to other molecules present in the sample.

In some embodiments, the binding moiety comprises an antibody, a lectin, a protein, a glycoprotein, a nucleic acid, monomeric nucleic acid, a polymeric nucleic acid, an aptamer, an aptazyme, a small molecule, a polymer, a lectin, a carbohydrate, a polysaccharide, a sugar, a lipid, or any combination thereof. In some embodiments, the binding moiety is a molecule capable of forming a binding pair with the target analyte.

In some embodiments, the binding moiety is an antibody or antibody fragment. Antibody fragments include, but are not limited to, Fab, Fab', Fab'-SH, $F(ab')_2$, Fv, Fv', Fd, Fd', scFv, hsFv fragments, cameloid antibodies, diabodies, and other fragments described above.

In certain embodiments, the binding moiety comprises an aptamer. In some embodiments, the aptamer comprises an antibody-analogue formed from nucleic acids. In some embodiments, the aptamer does not require binding of a label to be detected in some assays, such as nano-CHEM-FET, where the reconfiguration would be detected directly. In some embodiments, the binding moiety comprises an aptazyme. In some embodiments, the aptazyme comprises an enzyme analogue, formed from nucleic acids. In some embodiments, the aptazyme functions to change configuration to capture a specific molecule, only in the presence of a second, specific, analyte.

In some embodiments, the probe comprises a detectable label. Detectable labels include any composition detectable by spectroscopic, photochemical, biochemical, immunochemical, electrical, optical, or chemical means. Illustrative useful labels include, but are not limited to, fluorescent nanoparticles (e.g., quantum dots (Qdots)), metal nanoparticles, including but not limited to gold nanoparticles, silver nanoparticles, platinum nanoparticles, fluorescent dyes (e.g., fluorescein, texas red, rhodamine, green fluorescent protein, and the like, see, e.g., Molecular Probes, Eugene, Oreg., USA), radiolabels (e.g., $^{3}H$, $^{125}I$, $^{35}S$, $^{14}C$, $^{32}P$, $^{99}Tc$, $^{203}Pb$, $^{67}Ga$, $^{68}Ga$, $^{72}As$, $^{111}In$, $^{113m}In$, $^{97}Ru$, $^{62}Cu$, 641Cu, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Ab$, $^{199}Ab$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Th$, $^{177}Lb$, $^{105}Rh$, $^{111}Ag$, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like.

Alternatively or additionally, the probe can bind to another particle that comprises a detectable label. In some embodiments, the probes provide a detectable signal at the detection zone (e.g., test line, control line, test region, control region). In some embodiments, the detectable label/property comprises one or more of a colorimetric label/property, a fluorescent label/property, an enzymatic label/property, a colorigenic label/property, and/or a radioactive label/property. In some embodiments, the probe is a gold nanoparticle and the detectable property is a color. In some embodiments, the color is orange, red or purple.

Sample Collection

In various embodiments the sample to be assayed using the devices and methods described herein comprises a biological sample, an environmental sample, a food sample, etc. Illustrative biological samples include, but are not limited to biofluids such as blood or blood fractions, lymph, cerebrospinal fluid, seminal fluid, urine, oral fluid, vaginal fluid, and the like, tissue samples, plaque samples, endocervical swab samples, cell samples, tissue or organ biopsies or aspirates, histological specimens, and the like.

Where the biological sample comprises a tissue, in certain embodiments, the tissue may be lysed, homogenized, and/or ground and, optionally suspended in a sample solution. Where the biological sample comprises a biological fluid, the fluid may be assayed directly or suspended in a sample solution prior to assay. In certain embodiments the sample solution may act to preserve or stabilize the biological sample or components thereof, and/or may act to extract or concentrate the biological sample or components thereof. In certain embodiments the sample solution may comprise a buffer, optionally containing preservatives, and/or enzymes (protease, nuclease, etc.), and/or surfactants, and/or ATPS components.

In certain embodiments, particularly in point-of-care embodiments, the sample may be applied to the assay device immediately or after a modest time interval. In certain embodiments the sample may be delivered to a remote testing facility where the assay is run.

Methods and devices for collecting biological samples are well known to those of skill in the art, e.g., as illustrated below:

Oral Fluid Collection

Oral fluid can be collected by drooling into an empty vial, then transferring the fluid to the concentration component of the assay.

Oral fluid can also be collected using a swab and/or collection pad. For example, a swab or a collection pad can be placed in the user's mouth to soak up the oral fluid. The swab or the collection pad may contain compounds, such as peppermint extract, or a sour extract, to stimulate oral fluid production. The swab or collection pad can also act as a filter to remove food debris, contaminants, or mucus that may affect the downstream concentration and detection steps. In certain embodiments the oral fluid in the swab or collection pad can be extracted and mixed with aqueous two-phase (ATPS) components for concentration. Extraction of the oral fluid from the collection device can be accomplished, for example, by applying physical pressure to the swab/pad to squeeze the fluid out, or by capillary action to introduce the fluid to the concentration component. Another configuration corresponds to the ATPS components being dehydrated downstream of the swab or collection pad so that no further user interaction is necessary.

Plaque Collection

Plaque can be collected by brushes, swabs, or picks on the surfaces of teeth, underneath gum, or between teeth. In certain embodiments the collected plaque can then be mixed in buffer or an ATPS solution for subsequent concentration.

Urine Collection

In various embodiments urine can be obtained with a collection cup. The collected urine can then be mixed in an ATPS solution for subsequent concentration, or applied directly onto the device if ATPS components are dehydrated in the concentration component. In a catheterized subject, urine can be obtained from the catheter or from the catheter receiving bag.

Vaginal/Endocervical Swab

Target analytes on the vaginal or cervical surface and/or in vaginal fluid can be collected by commercially available swabs. The collected swab can be placed in a buffer to release the target, or placed in the ATPS solution for direct concentration of the target biomolecules.

Blood Collection

Blood can be collected by pin (lancet) prick and collection in a capillary tube, by syringe, and the like.

Illustrative Analytes.

While essentially any analyte can be detected and/or quantified using the assay devices and methods described herein, in certain embodiments, the analyte is a clinically relevant analyte (e.g., a bacterium, a fungus, a protozoan, an amoeba, a virus, and the like).

Clinically relevant targets are well known to those of skill in the art.

Clinically Important Bacteria in Vaginal Fluids

Finding *Trichomonas vaginalis*, bacterial vaginosis and *actinomyces* infections in vaginal fluid or tissue samples, pap smears might be considered an indication for treatment without performing other diagnostic tests. Treatment of asymptomatic infections can prevent complications in selected patients. *Candida* can be a commensal bacterium in the vagina, therefore asymptomatic patients may not require treatment. Detection of a higher rate of *Trichomonas vaginalis* and *candida* infection in intrauterine device (IUD) users show that IUDs can increase the risk of vaginal infections and associated complications.

Gonorrhea is a bacterial infection caused by the organism *Neisseria gonorrheae* and is a clinically important pathogen. Similarly, *Chlamydia*, caused by *Chlamydia trachomatis* and *syphilis*, caused by *Treponema pallidum* are important sexually transmitted disease whose rapid diagnosis is desirable.

Clinically Important Bacteria in Urine

*Escherichia coli* and *Proteus* sp. are bacterial pathogens that when found in urine are typically indicative of urinary tract infections.

Clinically Important Bacteria in the Oral Cavity

Gram-negative oral anaerobes have frequently been associated with periodontal disease, some species more frequently than others. Such anaerobes include, but are not limited to *Prevotella* species (e.g., *Pr. intermedia, Pr. Nigrescens, Pr. Melaninogenica, Pr. Veroralis*, and the like) and *Porphyromonas* species (e.g., *Porph. Gingivalis*).

Additionally *Streptococcus mutans* has been implicated in the formation of dental caries. Additional clinically important bacteria of the instant disclosure include but are not limited to *Actinomyces viscosus, Lactobacillus casei, Staphylococcus aureus, Candida albicans, Lactobacillus acidophilus, Capnocytophaga gingivalis, Fusobacterium nucleatum*, or *Bacteroides fortsythus*.

It will be recognized that these pathogens are illustrative and non-limiting. One of skill will recognize that the assay devices and methods described herein can be used to detect and/or to quantify numerous other analytes including, but not limited to food toxins and/or pathogens, environmental toxins and/or pathogens, and the like. Thus, for example, the methods and devices described herein can be used to detect *E. coli* contamination of vegetables or other foods and/or any other food pathogens including, but not limited to those illustrated in Table 2.

TABLE 2

Illustrative, but non-limiting food pathogens that can be detected using the methods and devices described herein.

| Pathogen | Sources |
|---|---|
| *Campylobacter jejuni* | Raw milk, untreated water, raw and undercooked meat, poultry, or shellfish |
| *Clostridium botulinum* | Home-canned and prepared foods, vacuum-packed and tightly wrapped food, meat products, seafood, and herbal cooking oils |
| *Clostridium perfringens* | Meat and meat products |
| *Escherichia coli* (*E. coli*) | Meat (undercooked or raw hamburger), uncooked produce, raw milk, unpasteurized juice, contaminated water, contaminated fruits and vegetables |
| *Listeria monocytogenes* | Refrigerated, ready-to-eat foods (meat, poultry, seafood, and dairy - unpasteurized milk and milk products or foods made with unpasteurized milk) |
| *Norovirus* (Norwalk-like Virus) | Raw oysters, shellfish, cole slaw, salads, baked goods, frosting, contaminated water, and ice. It can also spread via person-to-person. |
| *Salmonella enteritidis* | Raw and undercooked eggs, raw meat, poultry, seafood, raw milk, dairy products, produce, and nuts (e.g., almonds) |
| *Salmonella typhimurium* | Raw meat, poultry, seafood, raw milk, dairy products, and produce |
| *Shigella* | Salads, milk and dairy products, raw oysters, ground beef, poultry, and unclean water |
| *Staphylococcus aureus* | Dairy products, salads, cream-filled pastries and other desserts, high-protein foods (cooked ham, raw meat and poultry), and humans (skin, infected cuts, pimples, noses, and throats) |
| *Vibrio cholerae* | Raw and undercooked seafood or other contaminated food and water. |
| *Vibrio parahaemolyticus* | Raw or undercooked fish and shellfish |
| *Vibrio vulnificus* | Raw fish and shellfish, especially raw oysters |
| *Yersinia enterocolitica* | Raw meat and seafood, dairy products, produce, and untreated water |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Smartphones for the Analysis of Assay Results.

In certain embodiments a smartphone and associated attachment is provided for the detection and/or quantification of assay results. In certain embodiments the smartphone is configured for the detection and/or quantification of an analyte in an assay detection component, and comprises a smartphone comprising a camera; and a smartphone attachment where the attachment comprises a region for receiving an assay detection component; a light source that illuminates said detection component when the detection component is present in the attachment; and an optical path that transmits images of said detection component or regions thereof to said camera (see, e.g., FIG. 10). In certain embodiments the light source comprises a light emitting diode (LED). In certain embodiments a diffuser is disposed between the light source and the detection component. In certain embodiments a lens is disposed between the detection component and the camera. While Example 1 describes a smartphone attachment that is configured to transmit illumination through the detection component and into the optical path, it will be recognized that in certain embodiments, the attachment can configured to reflect illumination from a surface of the detection component and into the optical path.

In certain embodiments the smartphone is configured to obtain a control image of a control detection component lacking the analyte to be detected and/or a test image of a test detection component containing the analyte to be detected. In certain embodiments the smartphone is configured to detect the centroids of the signal(s) in the acquired control and/or test images. The smartphone can be configured to extract pixel information from a pixel box (or circle or ovoid, or other shape) disposed around the centroid(s). In certain embodiments the pixel box ranges from about 50 or from about 100, or from about 150, or from about 200 or from about 250, or from about 300 pixels by from about 50 or from about 100, or from about 150, or from about 200 or from about 250, or from about 300 pixels around said centroids. In certain embodiments the pixel box is about 200×200 pixels.

In various embodiments the smartphone is configured to determine the relative absorbance of the analyte bound in the detection component. For example, in certain embodiments the smartphone is configured to determine relative absorbance as $$A_{anal} = \log\left(\frac{I_{control}}{I_{test}}\right)$$

wherein $A_{anal}$ is the relative absorbance of bound analyte in the sample, $I_{control}$ is the signal intensity from the control sample, and $I_{test}$ is the signal intensity from the test sample. In certain embodiments the smartphone is configured to prompt a user to identify one or more analytes for detection. In certain embodiments the smartphone is configured to provide a calibration curve for the analyte(s) to be detected. In certain embodiments the smartphone is configured to calculate the analyte concentration from said calibration curve. In certain embodiments the smartphone is configured to back calculate the analyte concentration as:

$$A_{anal} = \varepsilon C_{anal} L \Rightarrow C_{anal} = \frac{A_{anal}}{\varepsilon L}$$

wherein $A_{anal}$ is the relative absorbance of bound analyte, εL is a calibration factor, and $C_{anal}$ is the concentration of analyte.

It will be recognized that the smartphone, attachment and algorithms described herein are illustrative and non-limiting. Using the teachings provided herein, numerous other attachments and analysis algorithms will be available to one of skill in the art.

Systems for the Detection and/or Quantification of an Analyte.

Figure 8A:
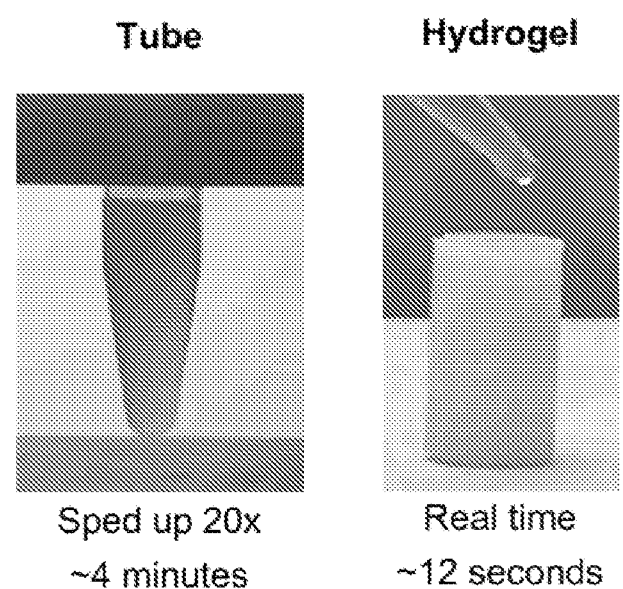
FIG. 8A illustrates that the use of a hydrogel can increase phase separation by as much as 20× or more.
Figure 8B:
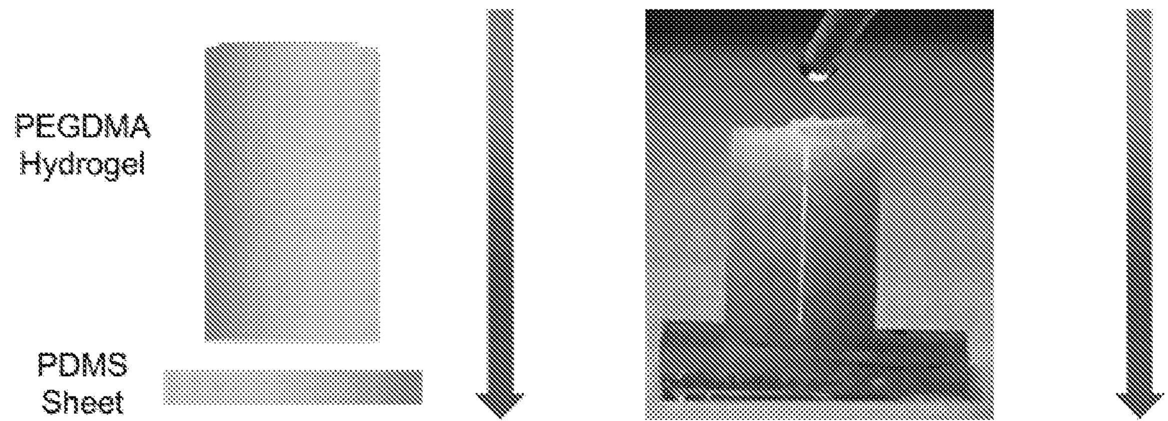
FIG. 8B illustrates that the ATPS can be combined with hydrogels. As shown, a solution of a mixed ATPS, in this case with gold nanoparticles (GNPs) and transferrin antigen (Tf), can flow through a hydrogel onto a detection component (e.g., polydimethylsiloxane (PDMS)) surface.

In various embodiments systems are provided for the detection and/or quantification of an analyte. In certain embodiments such systems utilize hydrogel scaffolds and aqueous two-phase systems as a pre-concentration method (see, e.g., FIG. 8A), and a conjugated transparent or translucent polymer (e.g., polydimethylsiloxane (PDMS)) as a detection component (see, e.g., FIG. 8B). In certain embodiments the system additionally includes a smartphone application and attachment that can provide greater sensitivity from the acquired signal (see, e.g., FIG. 9).

We have demonstrated the use of aqueous two-phase systems to concentrate biomarkers prior to detection with LFA, and in these approaches, have used paper to enhance the phase separation and concentration rate. Depending on the compositions of ATPSs used, 10-100 fold improvements in the limit of detection can be achieved over conventional LFAs. ATPSs improve on detection limits by concentrating biomolecules into one of the two phases (or to the interface), depending on hydrophobic and excluded-volume interactions the biomolecules experience with the components in each of the two phases.

For biomolecules that may not partition strongly to either phase, such as many proteins and small molecules, functionalized colorimetric nanoparticles conjugated with immobilized antibodies specific to the target biomolecule can be added to the system. These nanoparticles capture the biomolecule and then partition strongly to one phase of the ATPS primarily due to greater steric interactions with components in the other phase of the ATPS (or to the interface due to steric interactions with the components in both phases of the ATPS), causing the biomolecules to concentrate. The degree to which these biomolecules are concentrated can be well controlled due to fine adjustment of the volume ratio, which controls the volume of the phase containing the target. In certain embodiments the decorated nanoparticles can then serve as colorimetric indicators in the detection platform.

As described above, this approach can be extended to hydrogels, where hydrogel scaffolds are used as a pre-concentration method to accelerate phase separation as aqueous two-phase systems (ATPSs) rehydrate and travel through the scaffolds, concentrating target biomolecules into a leading front. This concentration was then coupled with the lateral-flow immunoassay (LFA).

This finding can be extended to the development of an integrated system that includes the hydrogel, ATPS, a detection component (e.g., a PDMS detection component), and, in certain embodiments, a smartphone application and attachment to improve detection limits.

We have demonstrated the ability of polyethylene glycol dimethacrylate (PEGDMA) hydrogels to enhance the phase separation rate of a variety of ATPS types. PEGDMA hydrogels be can synthesized by curing a precursor solution containing PEGDMA, a photoinitiator, and filtered sodium chloride crystals as porogens. The precursor solution is poured into transparent cylindrical (or other shaped) molds and placed under UV light to induce crosslinking. The salt is dissolved out from the gels by soaking the scaffolds in deionized water. The gels are then sublimated for, e.g., 2 hours before being stored at room temperature.

As described in Example 1, in one experiment, four different ATPS compositions (polyethylene glycol and potassium phosphate salt, Triton X-100 surfactant and dextran, Triton X-114 and sucrose, and 1-Butyl-3-methylimidazolium tetrafluoroborate ([BMIM][BF4]) and sulfate salt) were tested on these gels (see Table 3 in Example 1). To observe phase separation, bovine serum albumin (BSA)-gold nanoparticles and Brilliant Blue Dye FCF were added to the mixture, where the gold nanoparticles would partition to the relatively hydrophilic phase and the dye would partition to the relatively hydrophobic phase.

Figure 15:
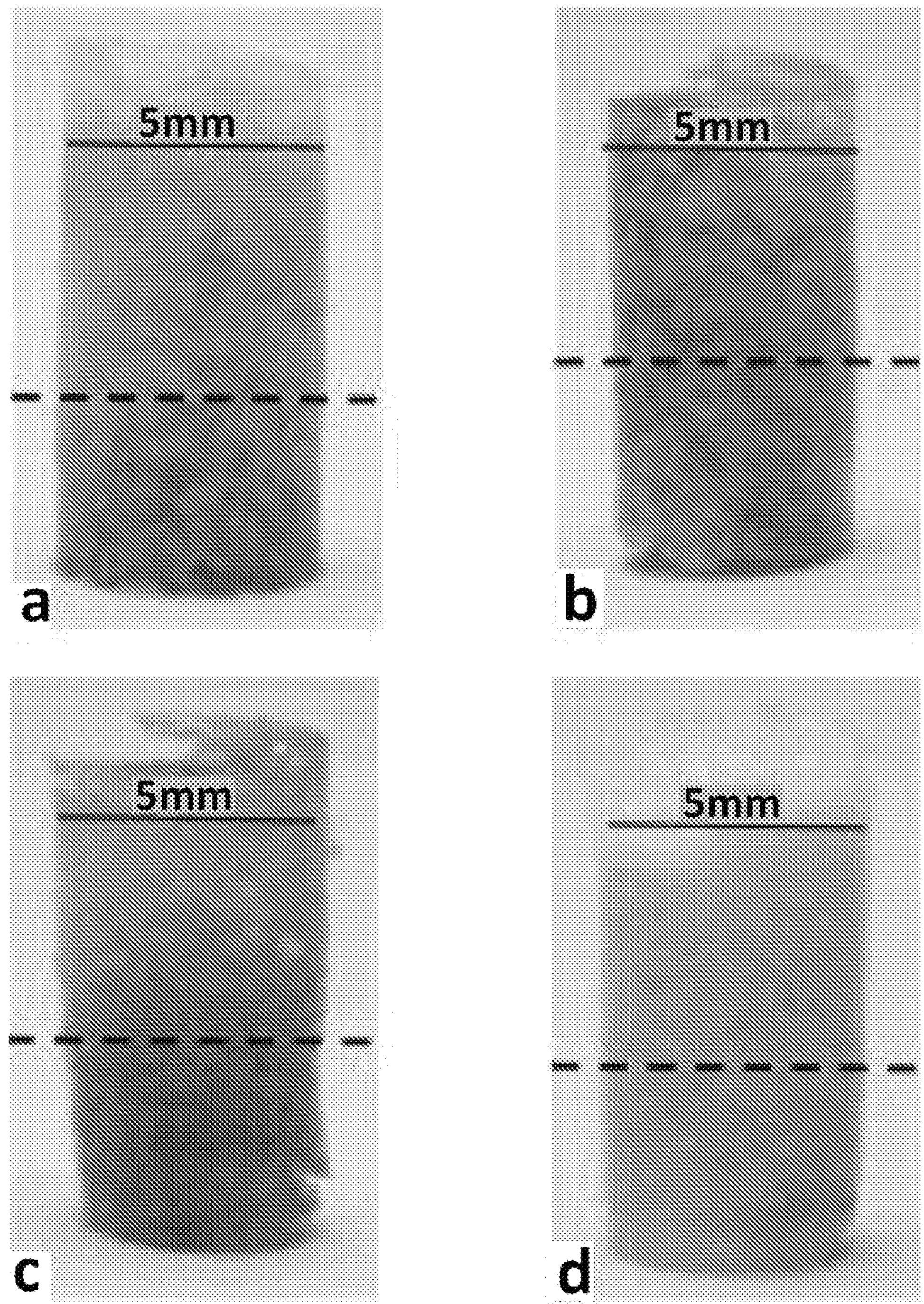

The mixture was applied to the top of the hydrogel and allowed to wick down the gel, producing two distinct phases in each of the ATPS types (see FIG. 15). These ATPS types range from polymer to micelle to ionic liquid and the ability of each ATPS to phase separate in our gel expands the general applicability of our system In certain embodiments detection components comprise a transparent or translucent polymeric substrate and glass. Illustrative substrates include, but are not limited to of PDMS, PMMA, Thermoset Polyester (TPE), and Polyurethane Methacrylate (PUMA).

In the illustrative example provided herein the detection component comprises PDMS. PDMS surfaces were conjugated with either target antigens or antibodies to induce binding between these immobilized proteins and conjugated nanoparticles that produced a colorimetric signal that indicated binding.

While many detection platforms utilize paper as a medium for testing, PDMS surfaces were utilized due to low cost and optical transparency, which reduces background and enhances sensitivity of detection as compared to opaque detection platforms such as LFAs. Furthermore, as PDMS surfaces are not porous and non-functionalized surfaces are inert, there is limited background caused by non-specific binding of the nanoparticles.

PDMS surfaces were synthesized by mixing 10 parts Sylgard silicone elastomer base with 1 part curing agent and placing the mixture in an oven for, e.g., 2 hours.

The cured scaffolds were then cut into smaller squares prior to protein conjugation. PDMS surfaces were conjugated with either target antigen or target antibody via an (3-aminopropyl)triethoxysilane (APTES)-glutaraldehyde conjugation scheme (see, e.g., FIG. 16). First, an APTES solution was prepared by mixing reagent alcohol, distilled water, glacial acetic acid, and APTES at a 95:5:5:1 ratio, respectively. This reaction was then covered with aluminum foil to prevent reaction to light and mixed with a magnetic stir bar for 15 minutes. Meanwhile, PDMS sheets were cleaned with isopropyl alcohol and plasma etched at room temperature for 3 minutes. They were then immersed in the APTES solution and placed on a slow-moving shaker for 45 minutes. The APTES solution was then removed, and the PDMS surfaces were rinsed in pH 7.4 phosphate-buffered saline (PBS) twice. The surfaces were then submerged in a 2.5% v/v solution of glutaraldehyde in PBS for 1 hour and 30 min at room temperature. Subsequently, the sheets were rinsed again twice in PBS and incubated in a 0.1 mg/mL solution of the capture protein in PBS with 1% Tween-20 for 30 minutes at room temperature. The surfaces were stored in PBS at 4° C. until use.

A smartphone application and attachment were developed and utilized to achieve quantitative analysis of the colorimetric signal. A smartphone attachment was designed using Computer Aided Design (CAD) software to hold and properly image the PDMS detection zone (see FIG. 10). The illustrated smartphone attachment consists of a green LED that emits light through a PDMS diffuser to diffuse the light as it travels through the PDMS sample. This transmitted light then travels through an aperture and is focused into the smartphone camera through the use of a plano-convex lens. This allows the transmitted light to be captured by the smartphone. It will be recognized, however, that the LED need not be limited to a green LED and, in certain embodiments LED color can be selected to optimize signal detection. Thus, for example, in certain embodiments, a UV LED might be used. Additionally, while the illustrated attachment utilizes light transmitted through the detection component, it will be recognized that the device (attachment) can be configured to utilize reflected light permitting, inter alia, the use of translucent or opaque detection components.

Figure 11:
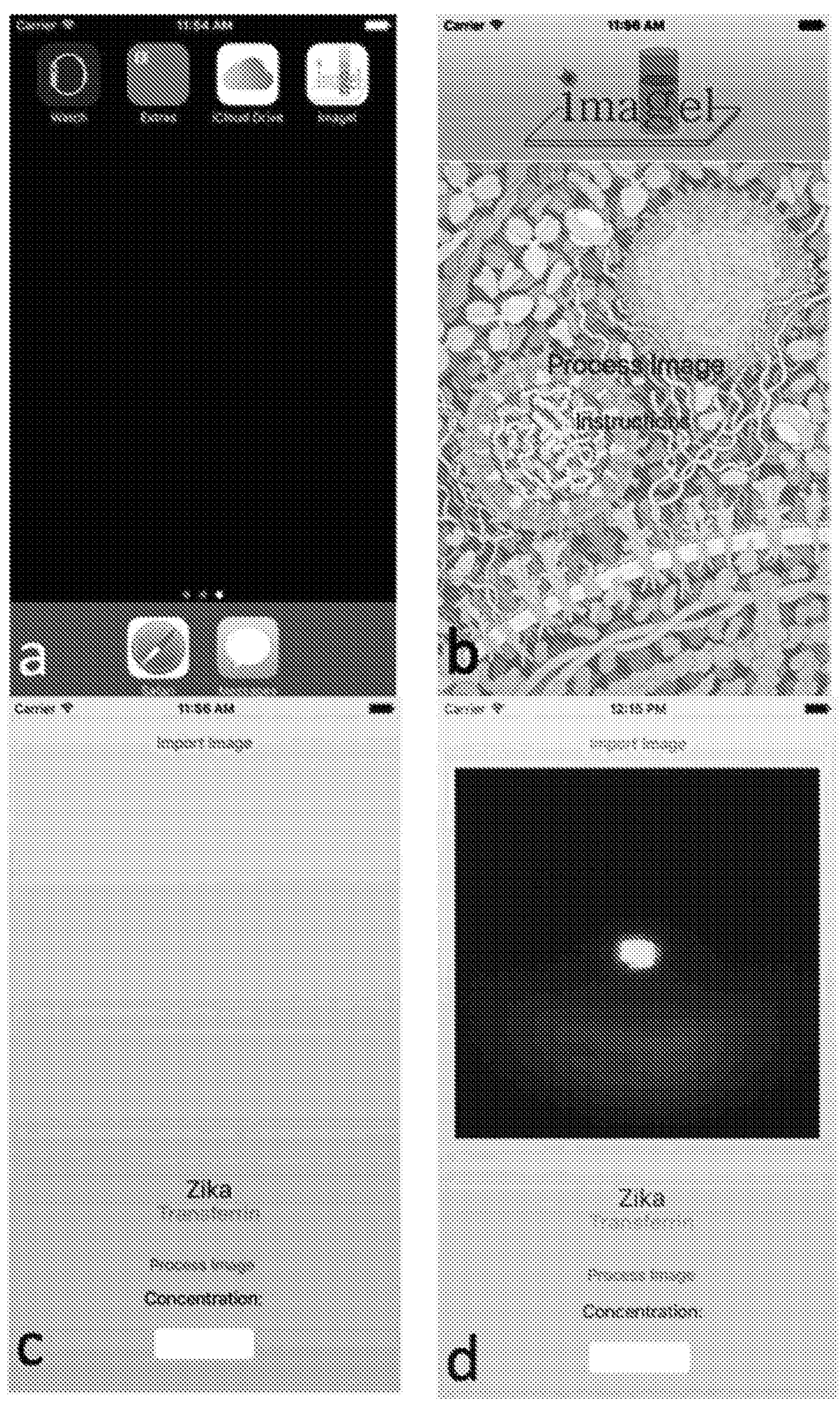
FIG. 11, panels a-d, illustrates a smartphone application user interface. Presented here are iPhone screenshots of the user workflow for the smartphone application. Panel a) The application icon presented on the iOS dashboard. Panel b) The application home page. Panel c) The user is prompted to upload an image from their camera roll. Panel d) User can select from various antigens to detect for, each with its own corresponding calibration factor, and then choose to process the image to attain an antigen concentration value.
Figure 12:
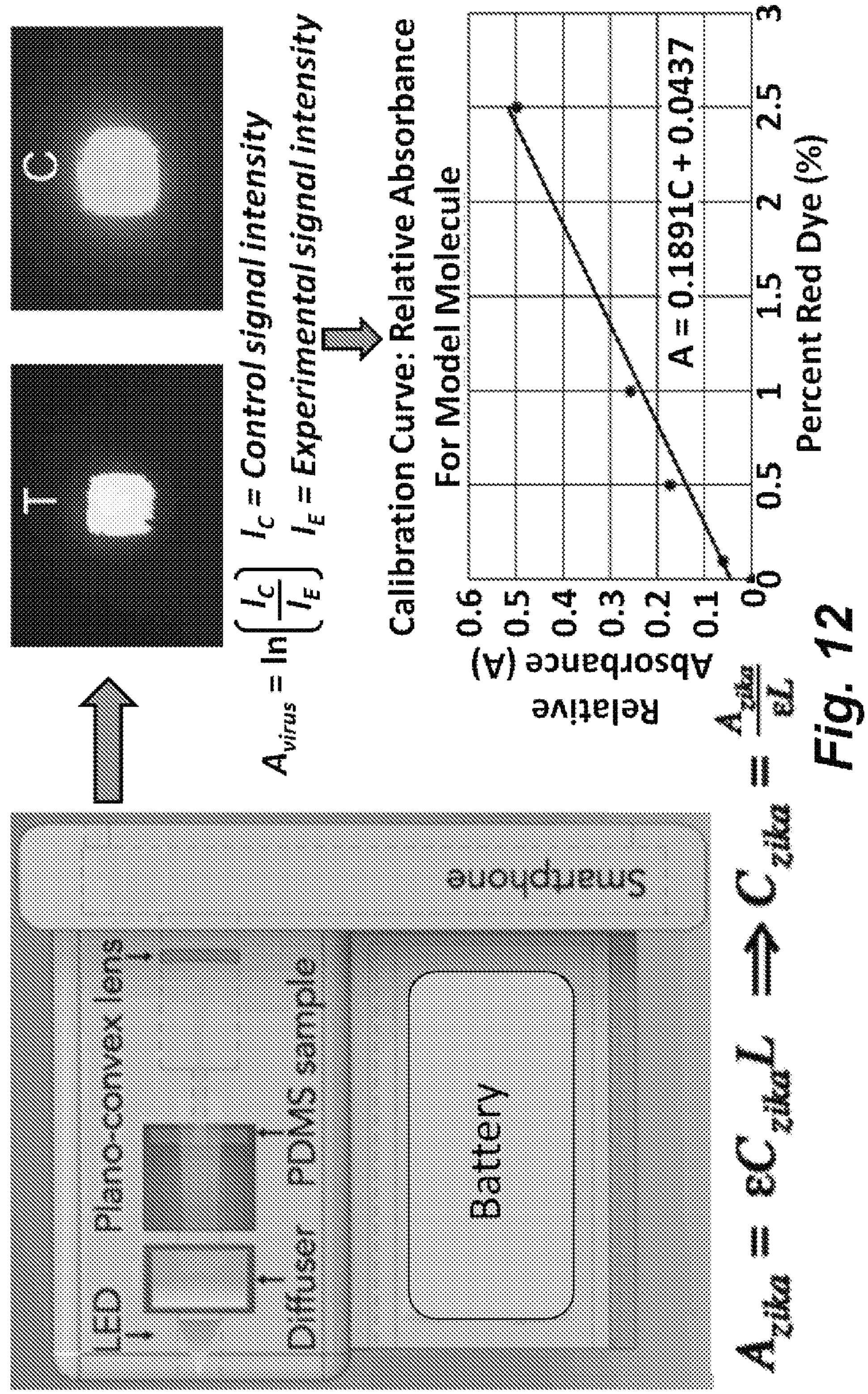
FIG. 12 illustrates the use of a smartphone and smartphone attachment to obtain a target analyte concentration. In the illustrated example, the analyte is a virus (Zika), however the analyte need not be so limited.

The generated image can be analyzed via a smartphone application (see, e.g., FIG. 11). In one illustrative, but non-limiting embodiment, both the test image and a control image used to normalize the test image intensity are inputted into the application. The application then extracts a 200×200 pixel box from the center of the most intense portion of the images. From this pixel box, the relative absorbance of the test PDMS surface can be calculated as $$A_{anal} = \log\left(\frac{I_{control}}{I_{test}}\right)$$

where $A_{anal}$ is the relative absorbance of the analyte, $I_{control}$ is the absorbance of the control and $I_{test}$ is the absorbance of the test sample. Analyte concentration can be calculated as $$C_{anal} = \frac{A_{anal}}{\varepsilon L}.$$

where $C_{anal}$ is the analyte concentration, and εL is determined via a calibration curve that is obtained from a panel of PDMS surfaces run with known concentrations of antigen.

To perform tests utilizing these PDMS surfaces and hydrogel scaffolds, a dehydrated hydrogel was placed upon a conjugated PDMS surface. A mixture containing conjugated colorimetric nanoparticles, ATPS components, and antigen was applied to the top of this dehydrated hydrogel. As it rehydrated the scaffold, phase separation was induced, producing a leading gold front that first contacted the PDMS surface. The remainder of the ATPS in the hydrogel exerted hydrostatic pressure to drive out the gold leading front and ensure that a large quantity of the gold makes contact with the detection surface.

In a proof-of-concept study, PDMS surfaces were conjugated with transferrin, while the nanoparticles were conjugated with transferrin antibodies, allowing for the detection of transferrin in the sample. In this case, a competition (competitive) assay was performed, due to the presence of antigen on the PDMS surface. Thus a negative result was exhibited by the presence of a red color in the PDMS, while a positive result was exhibited by the absence of red color, as the nanoparticles were saturated with antigen and could not bind to the surface. Alternatively, a sandwich assay can be performed using the same detection system, just by replacing the transferrin on the PDMS surface with immobilized transferrin antibodies.

Preliminary results indicate a limit of detection for transferrin to be 0.5 ng/μL, utilizing 1:1 polyethylene glycol and potassium phosphate salt ATPSs. Without using ATPSs within the hydrogels, early results show only a 5 ng/μL limit of detection, indicating a 10-fold improvement in detection. Furthermore, overall greater intensity in signal is achieved utilizing ATPSs, indicating not only greater sensitivity, but also reduced error due to greater contrast.

The detection component (e.g., PDMS surface) can then be transferred into the smartphone attachment and imaged. The image can subsequently be analyzed in the smartphone application.

This system has great potential as a point-of-care platform technology to detect for a variety of different diseases that have the appropriate antibodies and antigens available. This system improves upon existing point-of-care immunoassays, such as the LFA, due to (1) reduced background and increased signal intensity due to the optical transparency of the detection platform, e.g., PDMS, (2) improved limit of detection due to pre-concentration of biomarkers utilizing ATPSs in hydrogel scaffolds, and (3) quantitative results based on signal intensity utilizing a smartphone application and attachment.

It is believed that these systems are widely applicable due to the robustness of the conjugation scheme, the range of ATPSs able to phase separate within hydrogel scaffolds, and flexibility in assay schemes (competitive vs. sandwich).

Kits.

In certain embodiments kits are provided for use of the devices, systems, and/or practice of the methods described herein. In certain embodiments a kit for the detection and/or quantification of an analyte is provided where the kit comprises a container containing an assay device and/or the components of a system as described herein. In certain embodiments the kit additionally contains a collection device for collecting a sample. In certain embodiments the collection device comprises a device for collecting oral fluid, a device for collecting blood, a urine collection device, a device for collecting vaginal fluid or from an endocervical swab, or a device for collecting an environmental sample.

In certain embodiments the kits additionally contain reagents such as buffers, solvents, components of an ATPS system, detection reagents, and the like.

In certain embodiments the kits additionally contain instructional materials providing methods (e.g., protocols) for use of the assay devices provided therein. Often and typically the instructional materials are provided in written form and can be printed on the kit components themselves (e.g. on the cover of a box, container, or envelope), or can be provided as an insert/instructional page or booklet. While the instructional materials typically comprise written or printed materials they are not limited to such. Any medium capable of storing such instructions and communicating them to an end user is contemplated. Such media include, but are not limited to electronic storage media (e.g., magnetic discs, tapes, cartridges, chips, flash memory), optical media (e.g., CD ROM), and the like. Such media may include addresses to internet sites that provide such instructional materials.

EXAMPLES

The following examples are offered to illustrate, but not to limit the claimed invention.

Example 1

A Rapid, Sensitive, Hydrogel-Based Diagnostic Test for Point-of-Care Detection of the Zika Virus Abstract for Example 1.

The Zika virus, a flavivirus, recently emerged as a global threat particularly due to its devastating effects on fetal development. Therefore, a rapid, inexpensive Zika diagnostic test is critical for early, accurate detection as infected individuals are commonly asymptomatic or display nonspecific symptoms. Current diagnostic measures include point-of-care (POC) tests such as paper-based lateral-flow immunoassays (LFA), which lack in sensitivity and are unable to identify the active state of infection, and gold standard detection methods such as nucleic acid amplification tests, which require expensive laboratory equipment and trained personnel. Here, we report a novel, POC, polydimethylsiloxane (PDMS)-based immunoassay containing aqueous two-phase systems and polyethylene glycol dimethacrylate (PEGDMA) hydrogels for target pre-concentration, gold nanoparticles for colorimetric detection, and an image analysis software with a smartphone attachment for quantitative results. We demonstrate a proof-of-concept diagnostic device for transferrin (Tf) detection consisting of three components—(1) a hydrogel scaffold to concentrate target biomarkers through phase separation of aqueous two-phase systems, (2) a PDMS scaffold conjugated with anti-Tf antibodies, and (3) an image analysis component—to achieve detection of Tf at concentrations as low as 0.5 ng/μL. This technology offers an inexpensive (less than $5) and rapid (less than 30 minutes) alternative to gold standard diagnostic methods while improving upon the sensitivity of existing POC diagnostic tests.

Introduction

The Zika virus has existed and infected many populations since 1947, when it was first isolated in monkeys in Uganda. The first human infection was not recorded until 1954 in Nigeria, and for the next few decades, Zika did not cause any significant outbreaks to render the disease critical for diagnostic development. The first major outbreak of Zika was identified in 2007 in Gabon, and the infection quickly became a worldwide epidemic. By December 2015, Zika was suspected of infecting 1.3 million individuals. Additionally, transmission from mothers to babies is believed to lead to the development of Guillain-Barre syndrome, a crippling autoimmune disease (Baden 2016, Rasmussen 2016).

Commonly transmitted by *Aedes aegypti* mosquito, Zika disproportionately affects resource-poor areas, most notably Africa and South America (Marcondes 2016, Fauci 2016, Tambo 2016). There is thus a clear and present need for improved point-of-care (POC) detection to minimize the effect of future outbreaks. Currently, the gold standard tests for Zika detection include nucleic acid amplification tests (NAATs), plaque reduction neutralization tests (PRNTs), and enzyme-linked immunosorbant assays (ELISAs) (CDC 2017). All three benefit from high sensitivity, yet suffer several limitations. NAATs and ELISAs require access to laboratory equipment and trained personnel, and the PRNT takes several days to yield results. These drawbacks limit the use of these gold standard tests in the regions most impacted by Zika, leaving many infections undetected. As most of the cases of Zika occur in resource-poor settings, a highly sensitive yet easy-to-use POC device would be especially impactful at combatting this disease. Such a device would allow for easier screening of high-risk populations for the presence of the disease, and the implementation of health measures accordingly to reduce the number of congenital birth defects that occur as a result of infection.

One promising test is microfluidic immunoassays utilizing polydimethylsiloxane (PDMS). In recent years, PDMS has gained popularity for their low-cost, ease of fabrication, and optical transparency, and has served as a transparent detection platform for various immunoassays (Luo 2005, Yu 2009, Zhou 2009). However, PDMS surfaces suffer from a relatively inert surface and only a two-dimensional area to conjugate to, which can limit the sensitivity of any developed immunoassay (Kim, 2013). To improve upon this technology, a pre-concentration step can be applied.

Our approach is to utilize aqueous two-phase systems (ATPSs) in conjunction with hydrogel scaffolds, on which ATPSs will phase-separate. ATPSs have been used often for the purification and recovery of proteins for commercial purposes (Schütte 1997). Due to their ability to concentrate proteins while retaining protein functionality, ATPSs have also been demonstrated by the Kamei group to be useful as detection enhancement tools as they effectively enhance the sensitivity of lateral-flow immunoassays (Mashayekhi 2010, Mashayekhi 2012). However, phase separation in tubes may take hours to complete and require users to manually extract the top phase for detection. Therefore, to accelerate the phase separation and reduce user steps, we plan to use hydrogel scaffolds, a porous medium just like paper. Previously, the Kamei group has successfully incorporated ATPS concentration of target biomarkers with lateral-flow immunoassay (LFA) detection, and has demonstrated the acceleration of ATPS separation on paper compared to in a test tube (Chiu 2014, Pereira 2015). Through the incorporation of an ATPS through a hydrogel scaffold into our PDMS immunoassay, the antigen will similarly be concentrated prior to entering the detection zone, thus improving the limit of detection and decreasing the time scales for antigen to reach the detection zone. Moreover, the compatibility of ATPSs with patient samples will reduce the number of manual steps required to perform the test by eliminating any premixing steps.

Figure 9:
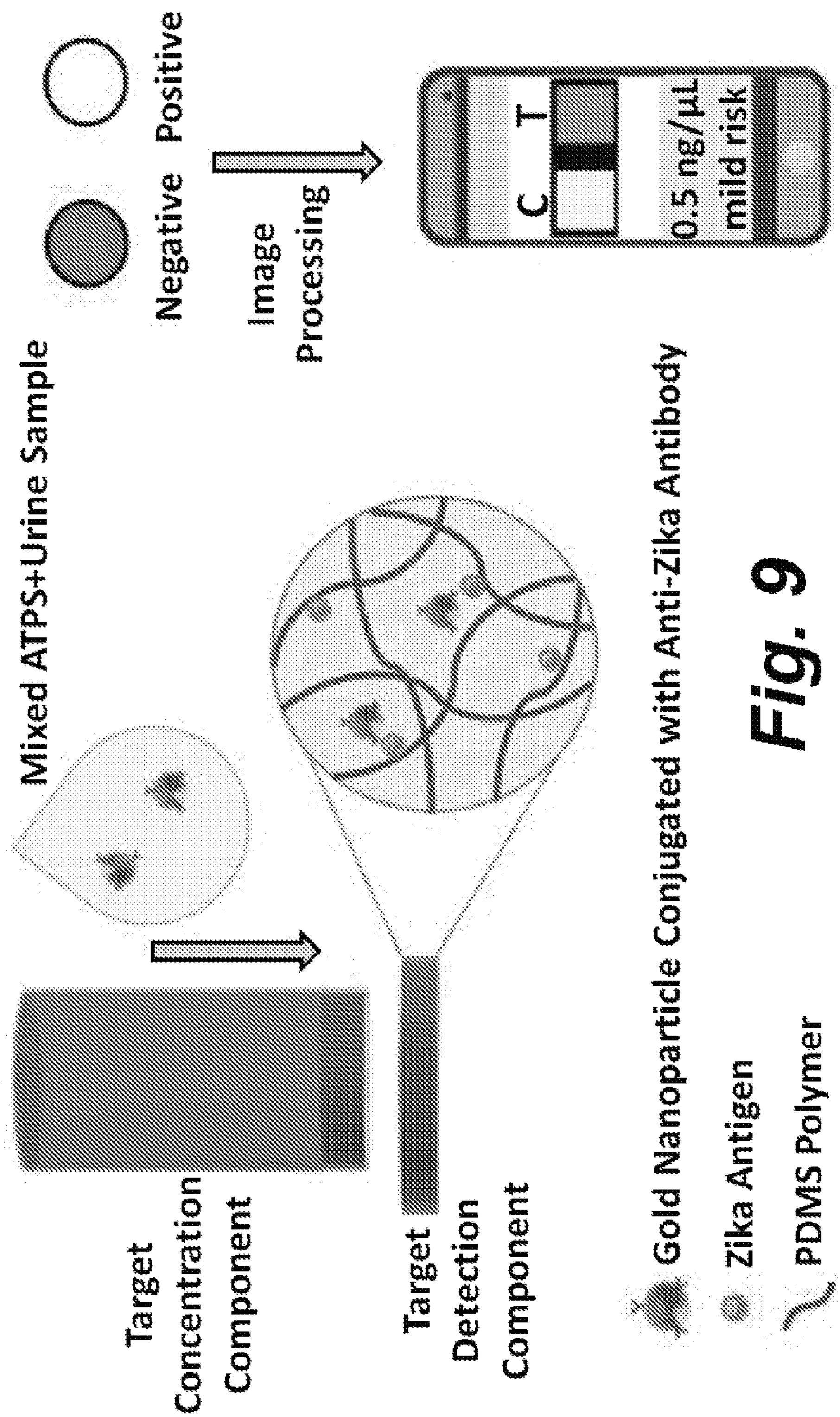
FIG. 9 shows an overview of an illustrative embodiment of an assay device/system. The device comprises a hydrogel component to concentrate the target antigen and a polydimethylsiloxane (PDMS) scaffold below it to detect the target. To perform a test, patient sample is mixed together with aqueous two-phase system (ATPS) components and gold nanoparticles (GNPs), then introduced at the top of the device. Phase separation of the ATPS occurs, concentrating any target-bound GNPs into the leading front. As the particles reach the PDMS detection surface, GNPs that are already bound to antigen from the sample (positive tests) will have no free binding sites and will not be able to bind to the antigen on the detection component. GNPs that are not bound to antigen from the sample (negative tests) will have available binding sites and will be able to bind to the antigen in the detection component. A mobile attachment and application quantifies the test results and assesses patient risk.

To our knowledge, this is the first study utilizing ATPSs to concentrate biomarkers on hydrogel scaffolds prior to detection on a PDMS surface. The device will also offer the ability to convert a qualitative measurement (indicated by the presence or absence of a "red" detection zone) into a quantitative measurement of Zika virus concentration in the patient sample through image analysis. In developing a PDMS-based immunoassay chip that incorporates a smartphone (with camera) attachment to analyze the chip, we can significantly improve upon the portability of current point-of-care detection methods for Zika. Furthermore, the use of Zika as our model antigen provides a framework to address a variety of diseases. Once developed, our device can serve as a starting point to develop a low-cost, rapid and widely applicable PDMS-based, multiplexed immunoassay platform for the simultaneous detection of several biomarkers. FIG. 9 presents an overview of the device components and the assay steps. The device will consist of a hydrogel scaffold followed by a PDMS surface, the hydrogel used to concentrate the target antigen, and the PDMS surface used for detection of the concentrated antigen.

Materials and Methods

All materials were acquired from Sigma-Aldrich Co., LLC, unless otherwise noted.

Synthesis of Polyethylene Glycol Dimethacrylate (PEGDMA) Hydrogels

PEGDMA hydrogels were prepared following a method described by the Brey group (Chiu 2010). Precursor solutions containing 70% PEGDMA and 0.1% Irgacure 2959 were prepared. NaCl crystals filtered through a sieve of 45 μm (therefore <0.45 μm) were introduced as porogens, at a ratio of 100 mg salt/200 μL solution. These solutions were pipetted into PDMS molds, then exposed to UV light on a UVP UV Transilluminator lamp (302 nm, 100V) for 20 minutes. Following crosslinking, hydrogels were soaked in deionized water for 16 hours to dissolve out the salt crystals, then sublimated for two hours and stored in a petri dish at room temperature.

Synthesis of Gold Nanoparticles (GNs)

Citrate-capped GNs were made according to Frens with slight modifications (Frens 1972, Frens 1973). First, 9.9 mL of filtered UltraPure sterile water (Rockland Immunochemicals Inc., Gilbertsville, Pa.) were stirred and heated to a boil in a scintillation vial. Then, 100 μL of 1% gold chloride were added and the solution was allowed to heat and stir for one minute. Next, 90 μL of 2% trisodium citrate were added and the solution was continuously stirred and heated until the color changed from clear to purple to red. Finally, the stir bar was removed and the GNs were stored at 4° C. The GNs were characterized for size and polydispersity via dynamic light scattering (DLS) measurements using a Zetasizer Nano ZS particle analyzer.

Conjugating Gold Nanoprobes (GNPs)

To make the GNPs, monoclonal anti-Zika antibodies (Fitzgerald Industries International, Acton, Mass.) were conjugated to the surface of the GNs through dative bonding. This was done by adding 0.1 M sodium borate to 1 mL of GNs to achieve a final pH of 9. Next, 8 μg of antibodies were added to the GNs and the solution was incubated on a Thermo Scientific Compact Digital MicroPlate Shaker at 700 rpm for twenty minutes to allow the dative bonding between the surface of the gold and the antibodies to occur. After this step, 100 μL of 10% bovine serum albumin (BSA) were added to cap the remaining binding sites on the GNPs. The solution was incubated for another ten minutes on the shaker, and then spun down three times at 8603 g to remove free antibodies. After the first two spins, the GNPs were resuspended in 200 μL of 1% BSA; and after the final spin, the GNPs were resuspended in 100 μL of 0.1M sodium borate. The GNPs produced were stored at 4° C. until needed.

Fluorescein Isothiocyanate (FITC)-Antigen Conjugation 10 mg of fluorescein isothiocyanate (FITC) were dissolved in 1 mL anhydrous dimethyl sulfoxide (DMSO). In a separate vial, antigen was prepared at a concentration of 1 mg/mL in phosphate-buffered saline (PBS) (Gibco). The two solutions were mixed to obtain 40-80 μg of FITC per mg of antigen. This was then incubated at room temperature for 1 hour. Unreacted FITC molecules were removed via dialysis against PBS. (i.e., MWCO: 8 kDa if the antigen is transferrin).

Synthesis of Polydimethylsiloxane (PDMS) Scaffold 10 parts Sylgard silicone elastomer base (Dow Corning) were mixed with 1 part curing agent (Dow Corning) and then placed in a 65° C. oven for 2 hours. The cured PDMS scaffolds were then cut into 0.5 cm by 0.5 cm squares prior to protein conjugation.

Conjugating Target Antigen onto PDMS Surface (3-aminopropyl)triethoxysilane (APTES) solution was prepared by mixing reagent alcohol (Fisher) and distilled water at a 95:5 ratio. Then, an equal volume of glacial acetic acid (Fisher) to the distilled water was added, and finally APTES was added to 1% of the total volume. The reaction was covered and allowed to run for 15 minutes at room temperature with a magnetic stir bar. Meanwhile, PDMS sheets fabricated as described previously were cleaned with isopropyl alcohol (J. T. Baker) and plasma etched at 500 mTorr for 3 minutes. Then, they were immersed in the APTES solution and placed on the shaker at room temperature for 45 minutes. The APTES solution was then removed, and the PDMS sheets were rinsed with PBS twice. A 2.5% v/v solution of glutaraldehyde in pH 7.4 PBS was poured over the PDMS scaffolds and the PDMS was placed on the shaker for two hours at room temperature. After the reaction was complete, the PDMS sheets were rinsed in pH 7.4 PBS and then incubated in a 0.1 mg/mL solution of the capture protein in PBS with 1% Tween 20 for 30 minutes at room temperature. Finally, the conjugated PDMS scaffolds were soaked in PBS and stored at 4° C. until needed.

Determining ATPS Compositions and Biocompatibility

Various ATPSs (composed of polymer/salt, surfactant/salt, surfactant/sugar, and ionic liquid/salt) with volume ratios (volume of top phase:volume of bottom phase) of 1:1, 9:1 and 1:9 were prepared by varying the weight percentages of the ATPS components. The compositions used are shown in Table 3. These systems were tested to determine which ATPSs phase separate quickly, while providing a mild bioenvironment to maintain the stability of proteins and GNPs. To test the biocompatibility of each ATPS, GNPs were introduced to the system and monitored for signs of aggregation which would indicate instability.

TABLE 3

Aqueous two-phase system (ATPS) compositions utilized that exhibited compatibility with gold nanoparticles. Compositions for both 1:1 volume ratios and 9:1 volume ratios are shown above.

| Aqueous Two-Phase System | 1:1 Volume Ratio Composition | 9:1 Volume Ration Composition |
|---|---|---|
| Triton X-114 (TX-114)/sucrose | 4.5% TX-114/10% sucrose | 8% TX-114/10% sucrose |
| Triton X-100 (TX-100)/dextran | 11% TX-100/9% dextran | 30% TX-100/4% dextran |

TABLE 3-continued

Aqueous two-phase system (ATPS) compositions utilized that exhibited compatibility with gold nanoparticles. Compositions for both 1:1 volume ratios and 9:1 volume ratios are shown above.

| Aqueous Two-Phase System | 1:1 Volume Ratio Composition | 9:1 Volume Ration Composition |
|---|---|---|
| Polyethylene glycol (PEG)/potassium phosphate salt | 9.83% PEG/7.67% potassium phosphate salt | 16.76% PEG/4.65% potassium phosphate salt |
| Ionic liquid/sulfate salt | 40% ionic liquid/4% sulfate salt | 70% ionic liquid/ 1.5% sulfate salt |

Investigating ATPS Phase Separation on Hydrogels

50 μL of well-mixed ATPS solutions was applied to the top of the dry hydrogel scaffolds. Macroscopic phase separation was visualized using Brilliant Blue FCF dye, which partitioned extremely into the more hydrophobic phase, and red GNs, which partitioned extremely into the phase with relatively fewer steric repulsive, excluded-volume interactions. Therefore, phase separation could be observed through the formation of a concentrated red phase containing the GNs and a blue phase containing the dye.

Performing Sample Detection on PDMS Immunoassay

Prepared lyophilized PEGDMA hydrogels were stacked on top of antigen-conjugated PDMS surfaces. Mixtures of 1:1 and 9:1 PEG/potassium phosphate salt ATPSs were prepared and mixed with 10 μg of antigen and 10 μL of GNPs. 504, of the mixed suspension were then applied to the top of the PEGDMA hydrogel and allowed to travel through the scaffold and make contact with the PDMS surface. A negative control, without any antigen, was performed concurrently. The sample was allowed to sit for 10 minutes before the hydrogel was removed. The PDMS surface was then inserted into its appropriate slot in the smartphone attachment and then imaged. The image was then analyzed as described below to give an antigen concentration.

Hardware Design

Figure 10:
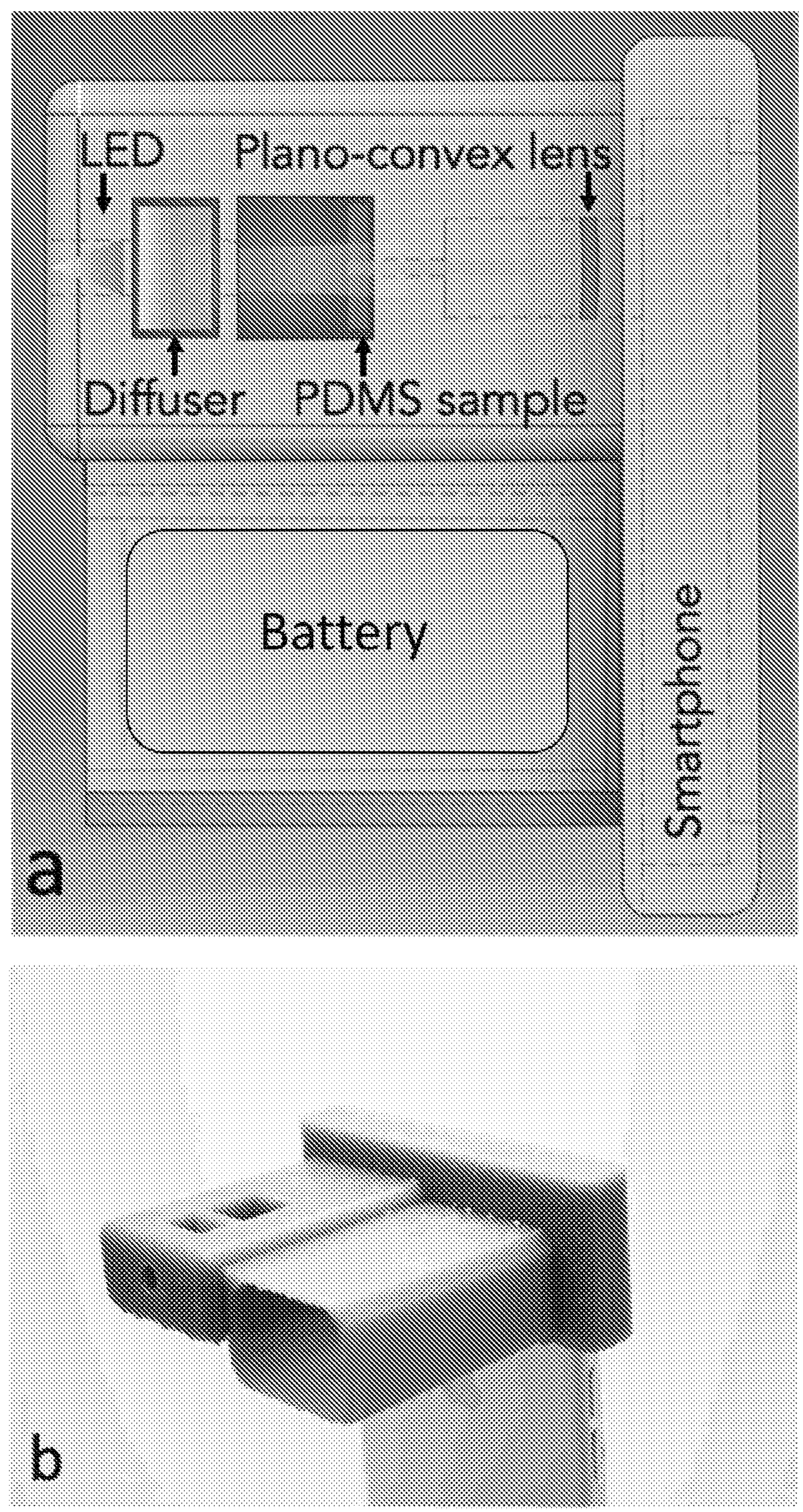
FIG. 10, panels a-b, illustrates a smartphone attachment. The smartphone attachment that we will use to image our samples is shown here. Panel a) Top view of the attachment, denoting the all optical components of the imaging pathway, consisting of an LED, diffuser, PDMS sample, and a plano-convex lens. Panel b) 3D-printed in ABS attachment design mounted onto an iPhone 6s.

A smartphone attachment (FIG. 10, panels a-b) was designed using Computer Aided Design (CAD) software (Inventor, Autodesk) to hold and properly image the PDMS detection zone. Hardware was designed to fit specifically onto an iPhone 6s (5.44×2.64×0.27 inches) as seen in FIG. 10, panel b, but very simple changes can be made to the attachment to accommodate any smartphone with a camera. This would merely entail modulating the distance between the walls and the camera aperture. This design was 3D-printed (Form2, Formlabs) with acrylonitrile butadiene styrene (ABS) filament, a low-cost, optically opaque, lightweight, and durable plastic that allows robust sample testing in resource-limited settings. To optimize the attachment's imaging capabilities, optical components were added to the 3D printed framework. Optical components inserted include: an LED (RadioShack, 580 nm, 12 degree viewing angle), a diffuser (Digikey), and one plano-convex lens (Edmund Optics, 22 mm focal length). The optical pathway of the attachment is shown in FIG. 10, panel a, where the "PDMS sample" is simply the "Target Detection Component" from FIG. 9. In short, the LED is used to illuminate the PDMS sample, of which the transmitted light will be collected by the smartphone camera. A 580 nm LED was chosen because it is most strongly absorbed by red GNPs that will bind strongly to the PDMS scaffolds in the case of the negative sample and to a lesser extent for a positive sample, thus giving the most prominent colorimetric difference in transmitted light between a positive and negative sample. The diffuser is used to spread out the incident light and ensure that the entire gel's cross-section will receive constant incident light intensity. Transmitted light is collected by the built-in rectangular aperture and imaged onto the plano-convex lens. The plano-convex lens collects more light and focuses the image for a clearer picture of the transmitted light. The attachment is designed so an iPhone 6S camera (f/2.2 aperture, 12-megapixels, 29 mm focal length) can be positioned immediately behind the lens, so as to collect the transmitted light from a sample, and subsequently process the image with a custom-built iPhone application.

Smartphone Application User Interface

The application was developed to work specifically on iOS systems, but a similar workflow and algorithm can be implemented on Android smartphones. The application's user interface (FIG. 11, panels a-d) was built to be intuitive and simple to use. The user-interface opens with a general description and instructions page, as shown in FIG. 11, panel a. The user can import an image from their camera roll (FIG. 11, panel b), and the image will be displayed on the screen for the user to validate prior to processing (FIG. 11, panel c).

Smartphone Image Processing

In order to accurately process transmitted images of the test samples, users first image a control sample with the smartphone attachment to properly calibrate the application. The control sample can simply be a PDMS scaffold that is optically transparent due to no bound GNPs. This will adjust for differences in smartphone cameras and the fluctuation of LED signal over time.

Figure 13:
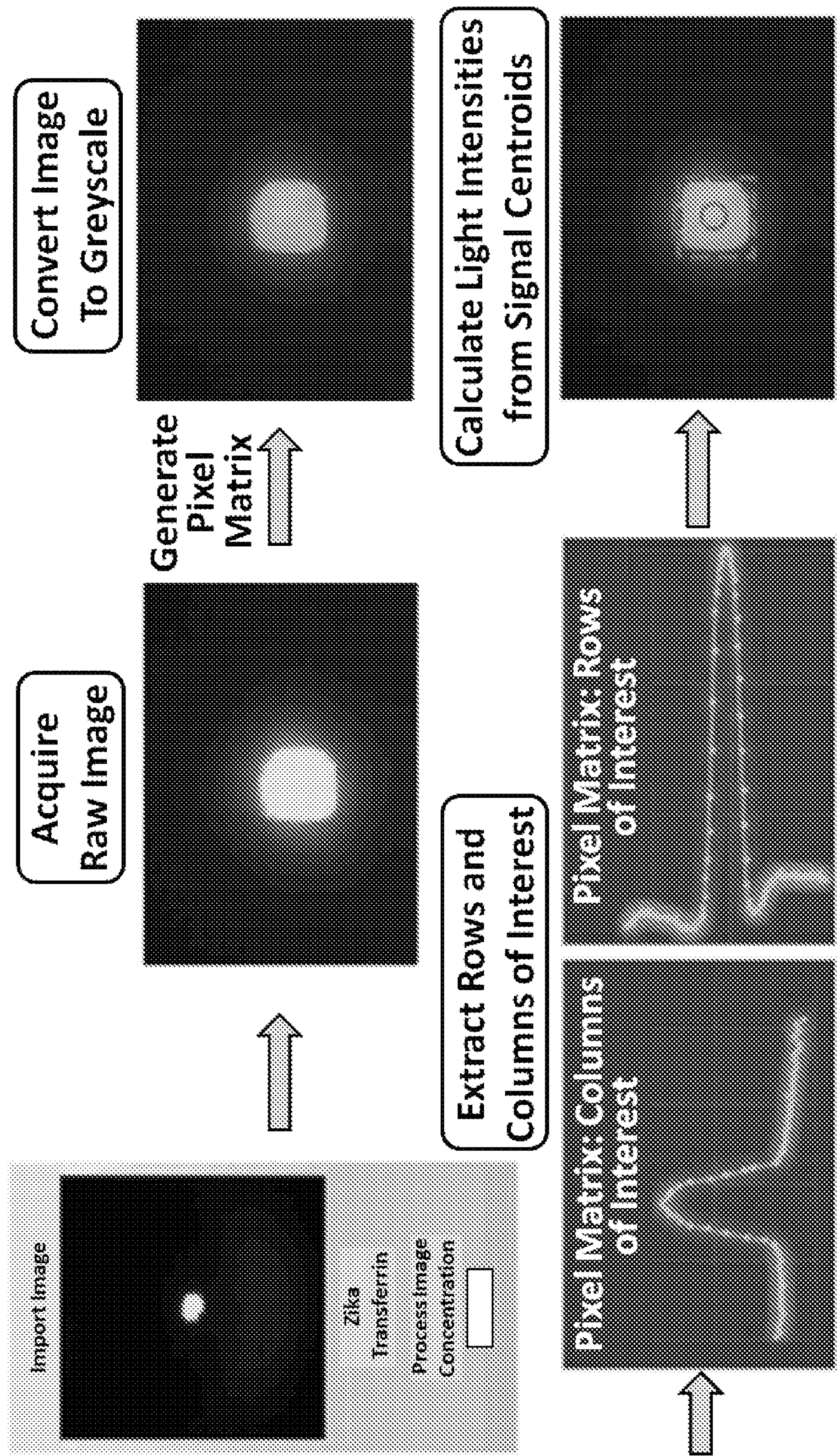
FIG. 13 illustrates a smartphone application image detection algorithm. Shown here is a flowchart of the steps taken on the back end of the application when the user chooses to process a transmitted image of their sample FIG. 14, panels a-d, illustrates phase separation phenomena for various ATPSs. The four aqueous two-phase systems (ATPSs) systems tested are shown here. All of these ATPSs are a 1:1 volume ratio, where the red phase represents the more hydrophilic phase and the blue phase represents the more hydrophobic phase. Panel a) Polyethylene glycol (PEG)/salt; Panel b) 1-Butyl-3-methylimidazolium tetrafluoroborate ([BMIM][BF4]) (Ionic Liquid)/salt; Panel c) Triton X-114/Sucrose; Panel d) Triton X-100/Dextran FIG. 15, panels a-d, illustrates phase separation of various ATPSs on hydrogels. The four mixed ATPSs are flowed down polyethylene glycol dimethacrylate (PEGDMA) hydrogels. Panel a) Polyethylene glycol (PEG)/salt; Panel b) Triton X-100/Dextran; Panel c) Triton X-114/sucrose; Panel d) Ionic liquid/salt. The black line indicates the interface of the two phases. All systems showed a leading gold phase flowing down the hydrogel scaffolds.
Figure 14:
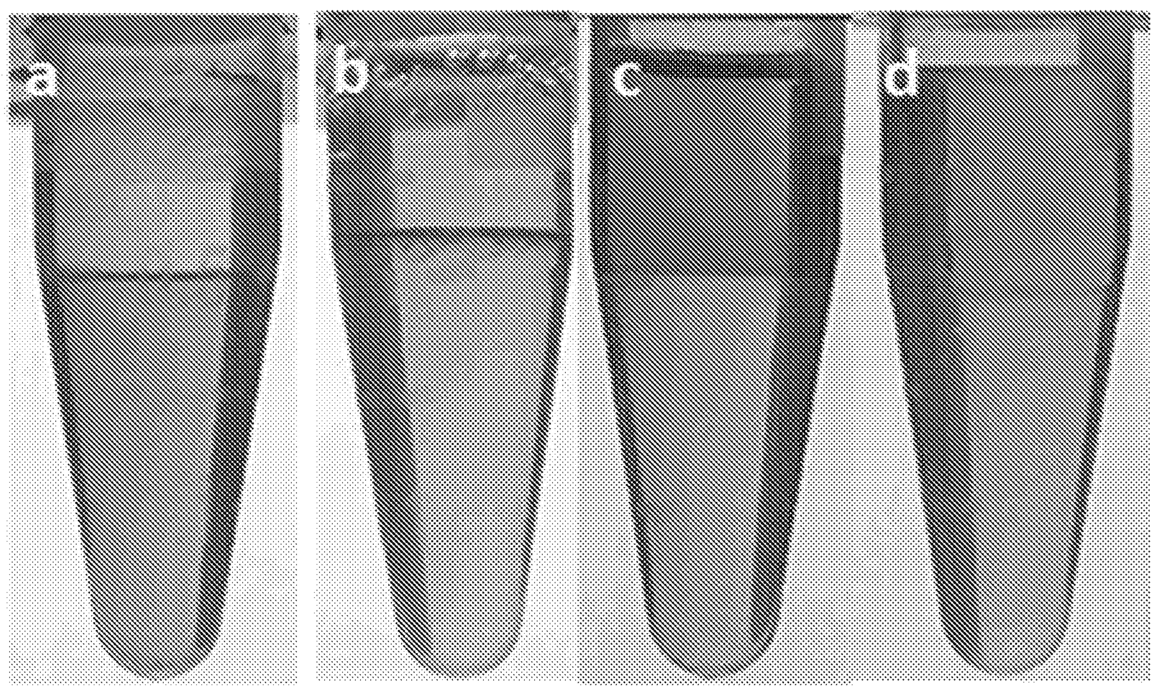

Once the transmitted image of a test sample is taken and uploaded into the application, the user will continue with the workflow by choosing to process the image. To detect the location of the signal, a fast image-detection algorithm is used to quickly detect the centroids of the two signals, as shown in FIG. 13. From there, pixel information is extracted from a 200×200 pixel box from the center of each of these centroids. The relative absorbance of Zika-bound GNPs in the sample is calculated as follows:

$$A_{zika} = \log\left(\frac{I_{control}}{I_{test}}\right) \tag{1}$$

where $A_{zika}$ is the relative absorbance of Zika-bound GNPs in the sample, $I_{control}$ is the transmitted signal intensity from the control sample, and $I_{test}$ is the transmitted signal intensity from the test sample. This relative absorbance value is then divided by a calibration factor (described in the section below) to return the concentration of Zika virus in the test sample.

Colorimetric Analysis Calibration

The calibration factor was determined by calculating the relative absorbance of Zika from 5 different known concentrations, and plotting these absorbance values against the known concentrations. Triplicate samples are made at each concentration. Then, a linear regression is performed, and the slope of the linear curve is the calibration factor relating the concentration of Zika to the resulting absorbance from colorimetric analysis. Thus, the concentration of Zika virus in an unknown sample is back-calculated accordingly:

$$A_{zika} = \varepsilon C_{zika} L \Rightarrow C_{zika} = \frac{A_{zika}}{\varepsilon L} \tag{2}$$

where εL is the calibration factor and $C_{zika}$ is the concentration of Zika in the sample.

Results and Discussion

Investigating ATPS Phase Separation on Hydrogels

Various ATPS solutions containing blue dye and red GNs were synthesized as described above and flowed down the PEGDMA hydrogel scaffolds. In investigating the ATPSs, we found component compositions for each for a volume ratio of 1:1, as shown in Table 3. In liquid form, the ionic liquid/salt ATPS exhibited the fastest phase separation time, phase separating within 30 seconds, while the TX-114/sucrose ATPS exhibited the slowest phase separation time, doing so within 40 minutes. Both the TX-114/sucrose and ionic liquid/salt ATPSs were top-partitioning systems, while PEG/salt and TX-100/Dextran were bottom-partitioning systems, as shown by the red phases. All exhibited clean partitioning, as seen by the apparent interface in each tube. When combining the ATPS and hydrogels, we compared the phase separation of each ATPS in each hydrogel system, as seen in FIG. 15. From this, we see that there was clear phase separation for all ATPSs, with a leading gold front and a lagging hydrophobic blue phase, as the liquid travels down the gel. A leading gold front will prevent any unfavorable interactions the lagging phase may have with the antibodies. This ensures the gold will be able to bind effectively to the antigen conjugated to the surface of the PDMS in the absence of the antigen in the sample. After achieving visible detection of the GNPs within the hydrogel, these PDMS gels were placed inside the smartphone attachment, as shown in FIG. 10. Once inside, the LEDs are turned on, an image is taken, and is subsequently processed with the custom-built smartphone application. Another iteration of the design can include the fluid wicking up the gel instead.

FITC Conjugation

Figure 17:
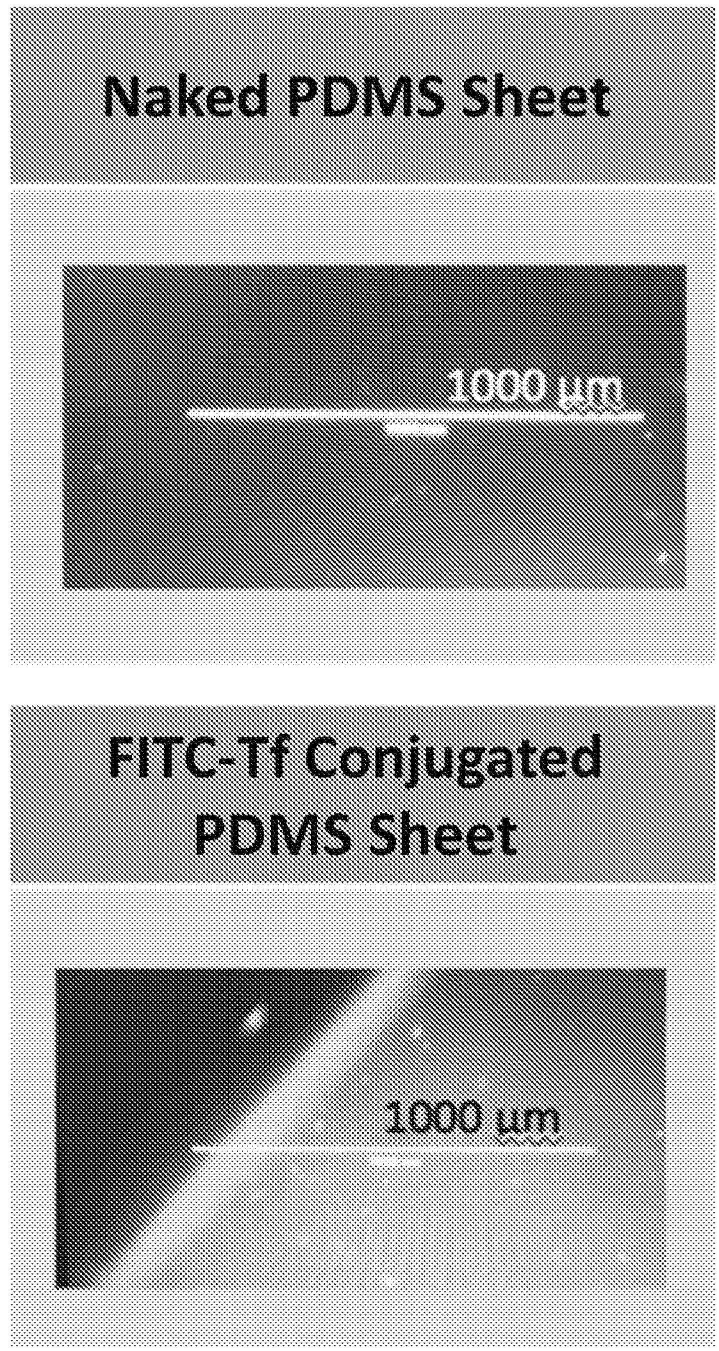
FIG. 17 illustrates conjugation of Fluorescein isothiocyanate (FITC)-labeled Tf to PDMS sheet. APTES-glutaraldehyde functionalized PDMS surfaces were incubated in Phosphate-Buffered Saline (PBS) (top) and FITC-labeled Tf (bottom) and then washed. The PDMS surfaces were then examined under a Green Fluorescent Protein (GFP) filter. The greater fluorescent intensity of the Tf (bottom) confirmed that Tf was covalently linked to the surface.

Here, APTES-glutaraldehyde functionalized PDMS scaffolds were soaked with PBS solution that does (or does not) contain FITC-labeled transferrin. As seen in FIG. 17, the functionalized scaffold in transferrin-containing solution glows under a GFP filter, which indicates that transferrin successfully binds to the surface of the scaffold. Additionally, the negative control does not glow. Therefore, this result displays the effectiveness of our conjugating scheme.

Conjugating Antigen on PDMS Surface

To test for successful conjugation of the target antigen to the PDMS scaffold, control tests were run with the conjugated surfaces by soaking the gels in GNP solutions both with (positive) and without (negative) the antigen. For our detection scheme, in a positive test, the antibodies on the GNPs will be saturated with the free-floating Tf in the solution, causing the GNPs to be unable to bind to the PDMS scaffolds, resulting in a clear surface. Meanwhile, in a negative test, the antibodies on the GNPs will bind to the transferrin on PDMS surface due to the lack of transferrin in solution, resulting in a red surface.

Figure 18:
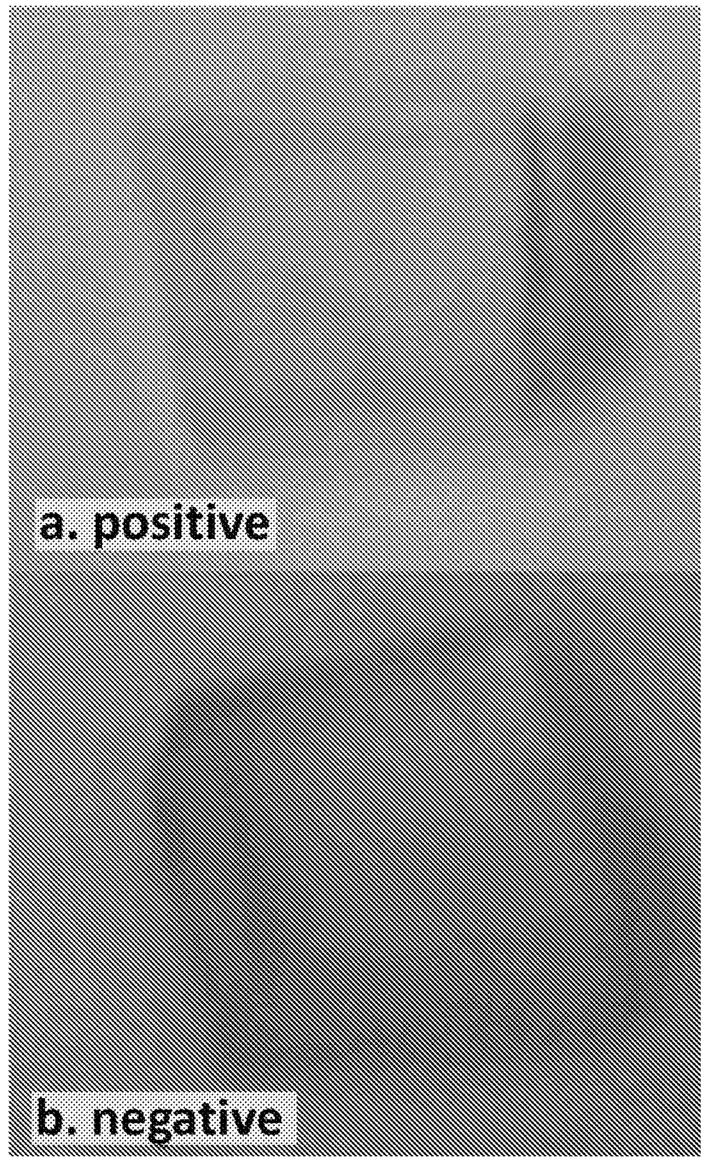
FIG. 18, panels a and b, illustrates detection on PDMS scaffolds (Competition Assay). Functionalized PDMS surfaces after being soaked in a GNP solution with or without a sample containing the target antigen. Panel a) The positive test is completely clear as all of the binding sites on the GNPs were occupied by the antigen from the sample and thus the GNPs were not able to bind to the antigen on the surface of the PDMS. Panel b) The negative test is red in color as the GNPs had free binding sites and were able to bind to the PDMS surface.

For the experiments, soaking the conjugated PDMS in GNP solutions has shown that positive tests (FIG. 18, panel a.) resulted in clear scaffolds, while the negative tests (FIG. 18, panel b) have a red color, suggesting that GNPs bind to the surface of the scaffolds in the negative tests, and not in the positive tests. Since the experimental results reflect our detection scheme, they demonstrate that we are able to conjugate antigen onto the PDMS surface.

Limit of Detection of Our Device

Figure 19:
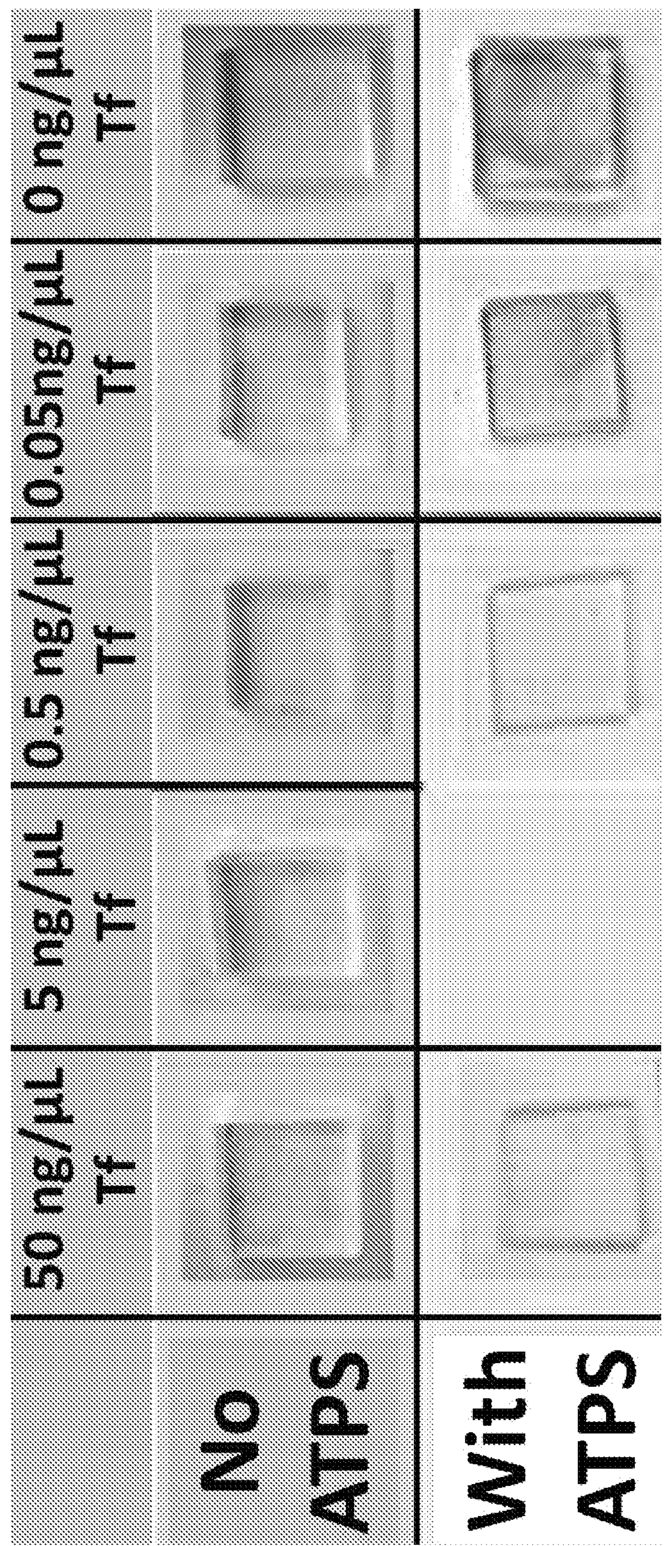
FIG. 19 illustrates the limit of detection of one embodiment of the device. We ran our device with solutions containing various concentrations of Tf to find the limit of detection of our device, defined as the lowest concentration at which our device can detect the presence of the protein. For the competition assay, the negative control appears pink as expected. Without ATPS, at 0.5 ng/μL, there is a slight pink signal on the PDMS surface, indicating a negative test. Meanwhile, the PDMS appears clear at 5 ng/μL. Therefore, the limit of detection without the use of ATPSs is 5 ng/μL. With ATPS, at 0.5 ng/μL, there is a clear signal on the PDMS surface, and at 0.05 ng/μL, there is a pink spot, indicating a negative result. Thus, we show a 10-fold improvement in the limit of detection to 0.5 ng/μL using ATPSs.

To determine the limit of detection of our device, we ran different solutions, containing various concentrations of Tf, down the gel and onto the PDMS surface. For our purpose, the limit of detection is defined as the concentration of Tf in solution, within the experimental sets, that first results in a completely transparent PDMS scaffold, which indicates a positive test. Based on visual analysis of the PDMS surfaces, the limit of detection without ATPS was 5 ng/μL for the model protein Tf. When performing tests utilizing 1:1 ATPSs, we found there was no signal at 0.5 ng/μL, dictated by the clear surface. At the next lowest concentration of 0.05 ng/μL, there was a signal, shown by the pink spot in FIG. 19. Thus the limit of detection with the ATPS incorporated was 0.5 ng/μL, and we show a 10-fold improvement in the limit of detection utilizing ATPSs in conjunction with PEGDMA hydrogels.

Conclusions

In this study, a novel approach to detect the Zika virus using a low-cost, rapid diagnostic platform was developed. Specifically, a PDMS-based immunoassay device was created that could concentrate target antigens using aqueous two-phase systems and hydrogel scaffolds, immobilize the antigens in a detection zone on the PDMS surface, and quantitatively analyze the results via a smartphone attachment. Using this setup, the detection of a model transferrin antigen was achieved at concentrations as low as 0.5 ng/μL. Furthermore, the assay only required less than 30 minutes to perform, and would cost only less than $5 to produce. The technical innovation described can be adopted to detect other disease biomarkers, potentially having a large impact on the field of point-of-care diagnostics.

REFERENCES FOR EXAMPLE 1

1. Scott C. Weaver, Federico Costa, Mariano A. Garcia-Blanco, Albert I. Ko, Guilherme S. Ribeiro, George Saade, Pei-Yong Shi, Nikos Vasilakis. Zika virus: History emergence, biology, and prospects for control. Antiviral Research 130, 69-80 (2016).
2. Lindsey R. Baden, Lyle R. Petersen, Denise J. Jamieson, Ann M. Powers, Margaret A. Honein. Zika Virus. New England Journal of Medicine 374, 1552-1563 (2016).
3. Sonja A. Rasmussen, Denise J. Jamieson, Margaret A. Honein, Lyle R. Petersen. Zika Virus and Birth Defects Reviewing the Evidence for Causality. New England Journal of Medicine 374, 1981-1987 (2016).
4. Jinzhao Song, Michael G. Mauk, Brent A. Hackett, Sara Cherry, Haim H. Bau, Changchun Liu. Instrument-Free Point-of-Care Molecular Detection of Zika Virus. Analytical Chemistry 88, 7289-7294 (2016).
5. David Y. Pereira, Ricky Y. T. Chiu, Samantha C. L. Zhang, Benjamin M. Wu, Daniel T. Kamei. Single-step paper-based concentration and detection of a malaria biomarker. Analytica Chimica Acta 882, 83-89 (2015).
6. Ricky Y. T. Chiu, Erik Jue, Allison T. Yip, Andrew R. Berg, Stephanie J. Wang, Alexandra R. Kivnick, Phuong T. Nguyen and Daniel T. Kamei. Simultaneous concentration and detection of biomarkers on paper. Lab on a Chip 14, 3021-3028 (2014).
7. H. Schütte. Protein Purification by Aqueous Two-Phase Systems. Springer Lab Manual, 31-48 (1997).
8. Yu-Chieh Chiu, Jeffery C. Larson, Anthony Isom, Eric M. Brey. Generation of Porous Poly(Ethylene Glycol) Hydrogels by Salt Leaching. Tissue Engineering Part C: Methods 16, 905-912 (2010).
9. G. Frens. Particle size and sol stability in metal colloids. Kolloid-Zeitschrift and Zeitschrift für Polymere 250, 736-741 (1972).

10. G. Frens. Controlled Nucleation for the Regulation of the Particle Size in Monodisperse Gold Suspensions. Nature Physical Science 241, 20-22 (1973).

11. Chunxiong Luo, Qiang Fu, Hao Li, Luping Xu, Manhui Sun, Qi Ouyang, Yong Chen, and Hang Ji. PDMS microfludic device for optical detection of protein immunoassay using gold nanoparticles. Lab on a Chip 5, 726-729 (2005).

12. Ling Yu, Chang Ming Li, Yingshuai Liu, Jie Gao, Wei Wang, and Ye Gan. Flow-through functionalized PDMS microfluidic channels with dextran derivative for ELISAs. Lab on a Chip 9, 1243-1247 (2009).

13. Jinwen Zhou, Amanda Vera Ellis, and Nicolas Hans Voelcker. Recent developments in PDMS surface modification for microfluidic devices. Electrophoresis 31, 2-16 (2009).

14. Dohyun Kim and Amy E. Herr. Protein immobilization techniques for microfluidic assays. Biomicrofluidics 7 (2013).

15. Carlos Brisola Marcondes and Maria de Fatima Freire de Melo Ximenes. Zika virus in Brazil and the danger of infestation by *Aedes* (*Stegomyia*) mosquitoes. Revista da Sociedade Brasileira de Medicina Tropical 49, 4-10 (2016).

16. Anthony S. Fauci and David M. Morens. Zika Virus in the Americas—Yet Another Arbovirus Threat. The New England Journal of Medicine 374, 601-604 (2016).

17. Ernest Tambo, Pascal D. Chuisseu, Jeanne Y. Ngogang, Emad I. M. Khater. Deciphering emerging Zika and dengue viral epidemics: Implications for global maternal-child health burden. Journal of Infection and Public Health 9, 240-250 (2016).

18. Center for Disease Control and Prevention. Diagnostic Tests for Zika Virus. Updated 18 Jan. 2017.

19. Foad Mashayekhi, Ricky Y. T. Chiu, Alexander M. Le, Felix C. Chao, Benjamin M. Wu, Daniel T. Kamei. Enhancing the lateral-flow immunoassay for viral detection using an aqueous two-phase micellar system. Analytical and Bioanalytical Chemistry 398, 2955-2961 (2010).

20. Foad Mashayekhi, Alexander M. Le, Parsa M. Nafisi, Benjamin M. Wu, Daniel T. Kamei. Enhancing the lateral-flow immunoassay for detection of proteins using an aqueous two-phase micellar system. Analytical and Bioanalytical Chemistry 404, 2057-2066 (2012).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An integrated assay device for the detection and/or quantification of an analyte in a sample, said device comprising:

a concentration component comprising a hydrogel configured to receive and/or contain an aqueous two-phase system (ATPS) where said hydrogel is configured to permit phase separation of said ATPS as said ATPS passes through and/or rehydrates said hydrogel thereby providing concentration of target analyte(s) into a leading front of said ATPS; and a detection component in fluid communication with said concentration component where said detection component comprises a lateral flow assay (LFA) or a flow-through (spot) assay and is configured to detect and/or quantify an analyte separated and/or concentrated by said concentration component.

2. The device of claim 1, wherein said hydrogel is hydrated prior to contact with an ATPS.

3. The device of claim 1, wherein said hydrogel is dried and configured to hydrate on contact with an ATPS.

4. The device of claim 1, wherein said detection component comprises a lateral-flow assay that comprises a porous matrix disposed in fluid communication with said hydrogel so that a fluid in said hydrogel can pass into said porous matrix.

5. The device of claim 1, wherein said device is configured to perform a competitive assay or a sandwich assay.

6. A method of separating and/or concentrating an analyte, said method comprising:

applying a sample comprising said analyte to a device comprising a hydrogel; and flowing an aqueous two-phase system (ATPS) through said hydrogel where said ATPS undergoes a phase separation thereby concentrating said analyte into a phase of said ATPS or concentrating said analyte into an interface between two phases of said ATPS.

7. A method of detecting and/or quantifying an analyte, said method comprising:

applying a sample comprising said analyte to a device of claim 1 where, in the presence of said analyte, said detection component produces a signal indicating the presence of said analyte; and detecting and/or quantifying said signal to indicate the presence and/or quantity of said analyte in said sample.

8. A kit for the detection and/or quantification of an analyte, said kit comprising:

a device of claim 1; and a collection device for collecting a sample.

9. An assay system for the detection and/or quantification of an analyte in a sample, said system comprising:

a concentration component comprising a hydrogel that contains an aqueous two-phase system (ATPS); and a detection component configured to detect and/or quantify an analyte separated and/or concentrated by said concentration component, where said detection component is in fluid communication with said concentration component.

10. A method of separating and/or concentrating an analyte, said method comprising:

applying a sample comprising said analyte to a system of claim 9;

permitting said ATPS to pass through said hydrogel thereby concentrating said analyte into a phase of said ATPS or concentrating said analyte into an interface between two phases of said ATPS;

disposing the ATPS phase or interface containing the analyte onto said detection component; and detecting and/or quantifying said analyte.

11. The device of claim 1, wherein said analyte comprises a moiety selected from the group consisting of a protein, a nucleic acid, a sugar or lectin, and a microorganism.

12. The method of claim 7, wherein said LFA or flow-through assay is one in which a binding moiety captures said analyte and in which a detection probe binds to said captured analyte.

13. The method of claim 7, wherein said analyte comprises a moiety selected from the group consisting of a protein, a nucleic acid, a sugar or lectin, and a microorganism.

14. The method of claim 13, wherein said analyte comprises a microorganism selected from the group consisting of a bacterium, a protozoan, a fungus, a virus, and an alga.

15. The method of claim 13, wherein said analyte comprises a biomarker for a microorganism.

16. The method of claim 15, wherein said target analyte comprises biomarker for a microorganism selected from the group consisting of a bacterium, a protozoan, a fungus, a virus, and an alga.

17. The method of claim 7, wherein said target analyte comprises a biomarker for a disease condition, a biomarker for food safety (or hazard), or a biomarker for a bioterror agent.

18. The system of claim 9, wherein said system further comprises a smartphone, wherein said smartphone comprises:

a smartphone comprising a camera; and a smartphone attachment said attachment comprising:

a region for receiving an assay detection component;

a light source that illuminates said detection component when said detection component is present in said attachment; and an optical path that transmits images of said detection component or regions thereof to said camera.

19. The method of claim 10, wherein said detecting and/or quantifying is performed using a smartphone, wherein said smartphone comprises:

a smartphone comprising a camera; and a smartphone attachment said attachment comprising:

a region for receiving an assay detection component;

a light source that illuminates said detection component when said detection component is present in said attachment; and an optical path that transmits images of said detection component or regions thereof to said camera.

20. The method of claim 10, wherein said analyte comprise Zika virus or a component thereof.

21. The device of claim 1, wherein said hydrogel comprises a polyethylene glycol dimethacrylate (PEGDMA) hydrogel.

22. The method of claim 9, wherein said ATPS comprises a polymer-salt ATPS selected from the group consisting of a polymer-polymer ATPS, a polymer-salt ATPS, and a micellar ATPS.

* * * * *